US007563594B2

(12) United States Patent
Yamasaki et al.

(10) Patent No.: US 7,563,594 B2
(45) Date of Patent: Jul. 21, 2009

(54) **CYTOLETHAL DISTENDING TOXINS AND DETECTION OF *CAMPYLOBACTER* BACTERIA USING THE SAME AS A TARGET**

(75) Inventors: Shinji Yamasaki, Osaka (JP); Masahiro Asakura, Osaka (JP)

(73) Assignee: Fuso Pharmaceutical Industries, Ltd., Osaka (JP)

(*) Notice: Subject to any disclaimer, the term of this patent is extended or adjusted under 35 U.S.C. 154(b) by 0 days.

(21) Appl. No.: 10/581,757

(22) PCT Filed: Dec. 3, 2004

(86) PCT No.: PCT/JP2004/018042

§ 371 (c)(1),
(2), (4) Date: Mar. 2, 2007

(87) PCT Pub. No.: WO2005/054472

PCT Pub. Date: Jun. 16, 2005

(65) Prior Publication Data

US 2007/0212691 A1    Sep. 13, 2007

(30) Foreign Application Priority Data

Dec. 5, 2003    (JP) .............................. 2003-408103

(51) Int. Cl.
*C12P 21/06*    (2006.01)
*C07H 17/00*    (2006.01)
(52) U.S. Cl. ................ 435/69.1; 435/320.1; 435/252.3; 435/325; 536/23.1
(58) Field of Classification Search ........................ None
See application file for complete search history.

(56) References Cited

U.S. PATENT DOCUMENTS

| 5,447,848 A | 9/1995 | Barns et al. |
| 5,691,138 A | 11/1997 | Guesdon et al. |
| 5,998,138 A | 12/1999 | Stonnet et al. |

FOREIGN PATENT DOCUMENTS

| EP | 0350205 B1 | 2/1995 |
| EP | 0711841 | 5/1996 |
| JP | 62228096 | 10/1987 |
| JP | 284200 | 3/1990 |
| JP | 2154700 | 6/1990 |
| JP | 3112498 | 5/1991 |
| JP | 5276999 | 10/1993 |
| JP | 690795 | 4/1994 |
| JP | 690796 | 4/1994 |
| JP | 7505535 | 6/1995 |
| JP | 10-508449 | 8/1998 |
| JP | 2000316590 | 11/2000 |
| JP | 2001524825 | 12/2001 |
| WO | WO 96/15261 | 5/1996 |
| WO | WO9842842 | 10/1998 |
| WO | 01/77372 | 10/2001 |

OTHER PUBLICATIONS

Bang et al. Jun. 2003b; PCT detection of seven virulence and toxin genes of *Campylobacter jejuni* and *Campylobacter coli* isolates from Danish pigs and cattle and cytolethal distending toxin production of the isolates. J. Applied Microbiology, 94(6): 1003-1014.*
Pickett et al. 1996; Prevalence of cytolethal distending toxin production in *Campylobacter jejuni* and relatedness of *Campylobacter* sp. cdtB genes. Infection and Immunity 64(6): 2070-1078.*
Bang et al. 2001a; Prevalence of cytolethal distinging toxin (CDT) genes and CDT production in *Campylobacter* spp. isolated from Danish broilers. J. Med. Microbiol. 50: 1087-1094.*
Eyigor et al. 1999a; Detection of cytolethal distending toxin activity and cdt genes in *Campylobacter* spp isolated from chicjken carcasses. Applied and Environmental microbiology. 65(4):1501-1505.*
Eyigor et al. 1999b; Cytolethal distending toxin genes in *Campylobacter jejuni* and *Campylobacter coli* isolates: Detection and analysis by PCR. J. Clinical Microbiology. 37(5): 1646-1650.*
Bang et al., "PCR detection of seven virulence and toxin genes of *Campylobacter jejuni* and *Campylobacter coli* isolates from Danish pigs and cattle and cytolethal distending toxin production of the isolates" Journal of Applied Microbiology, 94:1003-1014 (2003).
Bang et al., "Prevelence of cytolethal distending toxin (cdt) genes from CDT production in *Campylobacter* spp. isolated from Danish broilers" J. Med. Microbiol., 50L1087-1094 (2001).
Eyigor et al., "Cytolethal Distending Toxin Genes in *Campylobacter jejuni* and *Campylobacer coli* Isolates: Detection and Analysis by PCR" Journal of Clinical Microbiology, 37(5):1646-1650 (May 1999).
Eyigor et al., "Detection of Cytolethal Distending Toxin Activity and cdt Genes in *Campylobacter* spp. Isolated from Chicken Carcasses" Applied and Environmental Microbiology, 65(4):1501-1505 (Apr. 1999).
Pickett et al., "Prevalence of Cytolethal Distending Toxin Production in *Campylobacter jejuni* and Relatedness of *Campylobacter* sp. cdtB Genes" Infection and Immunity, 64(6):2070-2078 (Jun. 1996).

(Continued)

*Primary Examiner*—Karen Cochrane Carlson
(74) *Attorney, Agent, or Firm*—Karl Bozicevic; Bozicevic, Field & Francis LLP

(57) ABSTRACT

The present inventors succeeded in cloning the CDT genes of *C. coli* and *C. fetus*, which were previously unknown, and in determining their sequences. In addition, the inventors also developed specific primers and primers common to the two species by comparing the CDTs of *C. jejuni* and *C. fetus*. Furthermore, the inventors demonstrated that these primers were applicable to multiplex PCR that simultaneously allows for the rapid and convenient determination of the presence of *Campylobacter* CDT and identification of species, and that they can also be used in PCR-RFLP-based typing.

4 Claims, 19 Drawing Sheets

OTHER PUBLICATIONS

Volokhov et al., "Microarray-Based Identification of Thermophilic *Campylobacter jejuni, C. coli, C. lari,* and *C. upsaliensis*" Journal of Clinical Microbiology, 41(9):4071-4080 (Sep. 2003).

Gene Bank accession No. U51121.

Blaser et al., "*Campylobacter enteritis*: Clinical and Epidemiologic Features" Ann. Intern. Med. (Aug. 1979) 91(2):179-85.

Cortes-Bratti et al., "The *Haemophilus ducreyi* Cytolethal Distending Toxin Induces Cell Cycle Arrest and Apoptosis via the DNA Damage Checkpoint Pathways" J. Biol. Chem. (Feb. 16, 2001) 276(7):5296-302.

Kopecko et al., "*Campylobacter jejuni*-microtubule-dependent invasion" Trends Microbiol. (Aug. 2001) 9(8):389-96.

Kudoh et al., Syouni naika. (1997)29(9):1219-22.

Lara-Tejero et al., "A Bacterial Toxin That Controls Cell Cycle Progression as a Deoxyribonuclease I-Like Protein" Science (Oct. 13, 2000) 290(5490):354-7.

Lara-Tejero et al., "Cytolethal distending toxin: limited damage as a strategy to modulate cellular functions" Trends Microbiol., (Mar. 2002) 10(3):147-52.

Mizuno et al., "Characteristics of cytotoxin produced by *Campylobacter jejuni* strains" Microbios. (1994) 78 (317):215-28.

Okuda et al., "Examination of Diarrheagenicity of Cytolethal Distending Toxin: Suckling Mouse Response of the Products of the cdtABC Genes of *Shigella dysenteriae*" Infect Immun. (Feb. 1997) 65(2):428-33.

Oyofo et al., "Specific Detection of *Campylobacter jejuni* and *Campylobacter coli* by Using Polymerase Chain Reaction" J Clin Microbiol. (Oct. 1992) 30(10):2613-9.

Pickett et al., "The cytolethal distending toxin family" Trends Microbiol. (Jul. 1999) 7(7):292-7.

Romaniuk et al., "*Campylobacter pylori*, the Spiral Bacterium Associated with Human Gastritis, Is Not a True *Campylobacter* sp." J Bacteriol. (May 1987) 169(5):2137-41.

Shane et al., Diseases of Poultry, (2003) 615-30.

Suzuki et al., "Immunological properties and ganglioside recognitions by *Campylobacter jejuni*-enterotoxin and cholera toxin" FEMS Immunol Med Microbiol. (Mar. 1994) 8(3):207-11.

Takahashi et al., Infectious Diseases Weekly Report Japan (2001) 3(6):10-2.

Totten et al., "Prevalence and Characterization of Hippurate-Negative *Campylobacter jejuni* in King County, Washington" J Clin Microbiol. (Sep. 1987) 25(9):1747-52.

Asakura et al., "Development of a Multiplex PCR Assay for the Detection of the Cytolethal Ditending Toxin Genes in *Campylobacter jejuni, C. coli* and *C. fetus*" Abstracts of the General Meeting of the American Society for Microbiology. May 24, 2004; 104th:209 (#D-091).

Tauxe, Robert V., "Epidemiology of *Campylobacter jejuni* Infections in the United States and Other Industrialized Nations" *Campylobacter jejuni*: Current Status and Future Trends. 1991:9-19, American Society for Microbiology.

Asakura, et al., "Comparative analysis of cytolethal distending toxin (cdt) genes among *Campylobacter jejuni, C. coli* and *C. fetus* strains" Microbial Pathogenesis, 42:174-183 (2007).

* cited by examiner

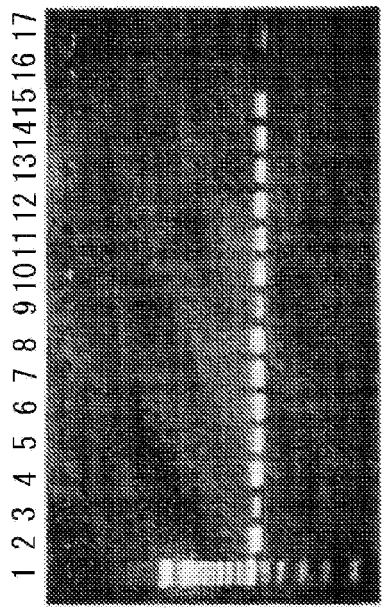
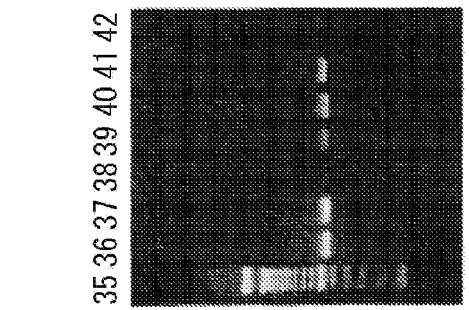

LANES 1,34,35: MOLECULAR WEIGHT MARKER
LANE 2: C.jejuni Co2-037
LANE 3: C.jejuni Co2-127
LANE 4: C.jejuni Co2-128
LANE 5: C.jejuni Co2-130
LANE 6: C.jejuni Co2-132
LANE 7: C.jejuni Co2-146
LANE 8: C.jejuni Co2-150
LANE 9: C.jejuni Co2-193
LANE 10: C.jejuni Co2-200
LANE 11: C.jejuni Co2-214
LANE 12: C.jejuni Co2-217
LANE 13: C.jejuni Co3-007
LANE 14: C.jejuni Co3-008
LANE 15: C.jejuni Co3-011
LANE 16: C.jejuni Co3-012
LANE 17: C.jejuni Co3-024
LANE 18: C.jejuni Co3-036
LANE 19: C.jejuni Co3-072
LANE 20: C.jejuni Co3-078
LANE 21: C.jejuni Co3-082
LANE 22: C.coli Co1-017
LANE 23: C.coli Co1-071
LANE 24: C.coli Co1-106
LANE 25: C.coli Co1-124
LANE 26: C.coli Co1-130
LANE 27: C.coli Co1-194
LANE 28: C.coli Co1-245
LANE 29: C.coli Co1-247
LANE 30: C.coli Co2-060
LANE 31: C.coli Co2-082
LANE 32: C.coli Co2-147
LANE 33: C.coli Co2-173
LANE 36: C.coli Co2-215
LANE 37: C.coli Co2-218
LANE 38: C.coli Co3-134
LANE 39: C.jejuni Col-8
LANE 40: C.coli Col-192
LANE 41: C.fetus Col-187
LANE 42: E.coli JM109

FIG. 12

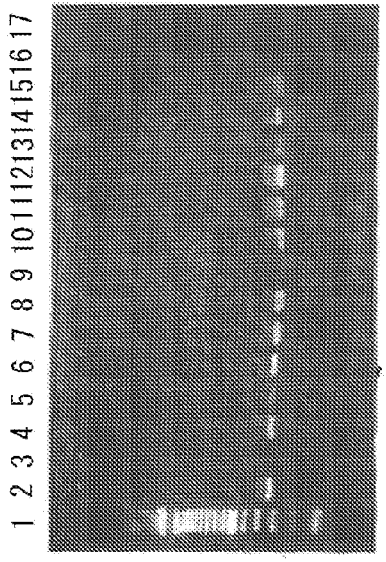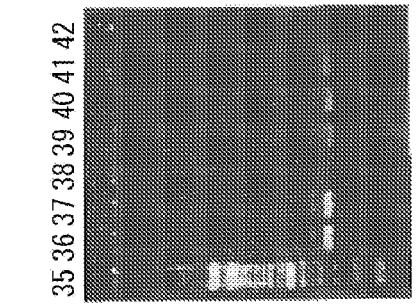
FIG. 13

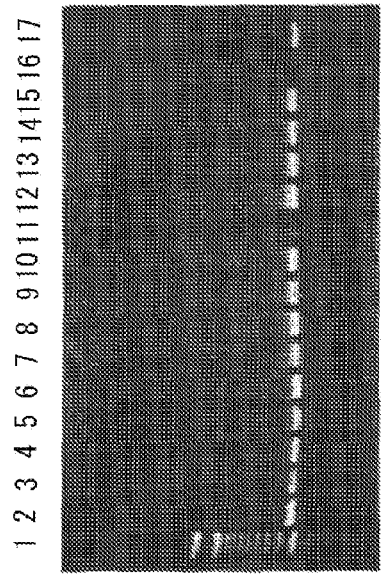
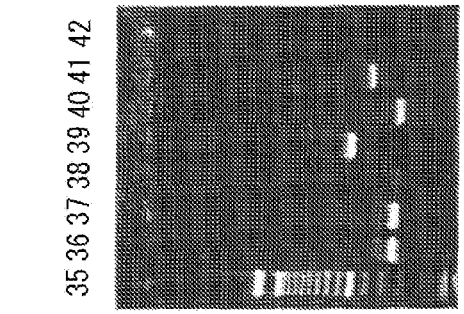

LANES 1, 34, 35: MOLECULAR WEIGHT MARKER
LANE 2: C.jejuni Co2-037
LANE 3: C.jejuni Co2-127
LANE 4: C.jejuni Co2-128
LANE 5: C.jejuni Co2-130
LANE 6: C.jejuni Co2-132
LANE 7: C.jejuni Co2-146
LANE 8: C.jejuni Co2-150
LANE 9: C.jejuni Co2-193
LANE 10: C.jejuni Co2-200
LANE 11: C.jejuni Co2-214
LANE 12: C.jejuni Co2-217
LANE 13: C.jejuni Co3-007
LANE 14: C.jejuni Co3-008
LANE 15: C.jejuni Co3-011
LANE 16: C.jejuni Co3-012
LANE 17: C.jejuni Co3-024
LANE 18: C.jejuni Co3-036
LANE 19: C.jejuni Co3-072
LANE 20: C.jejuni Co3-078

LANE 21: C.jejuni Co3-082
LANE 22: C.coli Co1-017
LANE 23: C.coli Co1-071
LANE 24: C.coli Co1-106
LANE 25: C.coli Co1-124
LANE 26: C.coli Co1-130
LANE 27: C.coli Co1-194
LANE 28: C.coli Co1-245
LANE 29: C.coli Co1-247
LANE 30: C.coli Co2-060
LANE 31: C.coli Co2-082
LANE 32: C.coli Co2-147
LANE 33: C.coli Co2-173
LANE 36: C.coli Co2-215
LANE 37: C.coli Co2-218
LANE 38: C.coli Co3-134
LANE 39: C.jejuni Col-8
LANE 40: C.coli Col-192
LANE 41: C.fetus Col-187
LANE 42: E.coli JM109

FIG. 15

C. jejuni cdt ORF
ATGCAAAAAATTATAGTTTTTATTTTATGTTGTTTTATGACTTTTTTTCTTTATGCATGTTCTTCTAAATTTGAAAATGT
AAATCCTTTGGGGCGTTCATTTGGAGAATTT$_{64}$GAAGATACTGATCCTTTAAAAC$T_7$AGGACTTGAACCTACTTTTC$_{68}$CT
ACCAATCAAGAAATTCCAAGTTTAATTAGCGGTGCTGATTTAGTACCTATTACTCCTATTACCCCACCTTTAACTAGAAC
AAGCAATAGTGCCAACAATAATGCAGCAAATGGGATCAATCCTCGCTTTAAAGACGAAGCTTTTAATGATGTTTTAATTT
TTGAAAATCGCCCTGCGGTTTCTGATTTTTTAACCATTTTAGGCCCTAGCGGAGCAGCTTTAACGGTTTGGGCTTTAGCA
CAAGGAAATTGGATTTGGGGCTATACTTTAATCGATAGCAAAGGATTTGGCCGATGCTAGAGTTTGGCAACTTTTGCTTTA
TCCTAATGATTTTGCAATGATTAAAAATGCCAAAACCAATACTTGTCTTAATGCTTATGGTAATGGAATTGTCCATTATC
CTTGTGATGCAAGCAATCACGCACAAATGTGGAAACTTATCCCTATGAGCAATACAGCGGTTCAAATTAAAAATTTAGGA
AATGGAAAA$_{65}$TGCATACAAGCACCTATTAC AAATCTTTATGGTGATTTTCACAAGGTTTTTAAAATTTTTACCGTAGAG
TGTGCAAAAAAAGATAATTTTGATCAACAAT$_{69}$GGTTTTTAACTACTCCGCCTTTTACCGCA$_{11}$AAACCTTTATATCGCCA
AGGAGAGGTACGATGAAAAAAATTATATGTTTATTTTTATC$_{17}$TTTTAACCTTGCTTTTGCAAATTTAGAAAATTTTAAT
GTTGGCACTTGGAATTTGCAAGGC$_9$TCATCCGCAGCCACAGAAAGCAAATGGA$_{18}$GTGTTAGTGTAAGACAACTTGTAAGT
GGAGCAAACCCCTTAGATATCTTAATGATAC$_{26}$AAGAAGCAGGAACTTTACCAAGAAC$_{29}$AGCCACTCCAACAGGACGCC$_{19}$
ATGTGCAACAAGGTGGAACACC$_{27}$TATTGATGAATATGAGTGGAATTTAGG$_{20}$AACTCTTTCAAGGCCTGATAGGGTTTTT
ATTTATTATTCTCGCGTTGATGTAGGAG$_{48}$CTAATCGTGTAAATTTAGCTATAGTT$_T$TCAAGAATGCAAGCTGAA$_{21}$GAAGT
GATTGTTTTACCTCCACCTACTACAGTTTCAAGACCCATTATAGGAATTCGCAATGGAAATGATGCTTTTTTCAATATCC
ATGCTTTAGC$_{49}$TAATGGAGGAACAGATGTAGGAGCAATTATCACAGCTGTAGATGCACA$_{22}$TTTTGCAAATATGCCTCAA
GTTAACTGGATGATAGCAGGGGATTTTAA$_{50}$CCGTGATCCTTCTACTATAACAAGT$_{23}$ACAGTGGATAGAGAATTAGCAAA
TAGAATTAGAGTGGTTTTTCCAACTAGCGCAACTCAAGCAAGCGGAGGGACTCTTGATTATGCAATTACAGGAAATTCAA
ATA$_{24}$GACAACAAACCTATACTC$_{12}$CACCGCTTTTAGCTGCGATTTTAATGCTTGCAAGTTTAAGATCTCATAT$_{25}$AGTTTC
AGATCATTTTCCAGTAAATTTTAGA$_{10}$AAATTTTAGGACATTTAATATGAAAAAAATTATTACTTTGTTTTTTATGTTTA
TAACTTTAGCCTTTGCAACTCCTA$_{74}$CTGGAGATTTGAAAGATTTTACCGAAATGGTTTCTATAAGAAGCTTAGAAACGG
GAATTTTTTTAAGCGCCTTTAGGGATACCTCAAAA$_{66}$GATCCTATTGATCAAAATTGG AATATTAAAGAAATTGTTTTAA
GCGATGAGTTAAAACAAAAAGATAAATTAGCTGATGAACTTCCTTTTGGTTATGTGCAATTTACAAATCCAAAAGAAAGC
GATCTTTGTTTAGCCATCTTAGAAGATGGAACCTTTGGAGCAAAATCTTGTCAAGATGATCTAAAAGATGGTAAATTAGA
AACTGTATTTTCTATAATGCCAACAACAACTTCAGCTGTGCAAATTCGTTCTTTAGTTTTGGAATCTGATGAATGTATAG
TAACTTTTTTTAATCCAAATATTCCTATACAAAAACGCTTTGGAA$_8$TAGC$_{67}$CCCTTGCACCCTAGATCCTATTTTTTTT
GCTGAAGTAAATGAACTAATGATTATAACCCCACCTTTAACAGCTGCTACCCCTT$_{75}$TAGAATAA

FIG. 17

C. coli cdt ORF
ATGCAAAAAATAAAATTAAGCCTAATGTTTTTGATTGTAACAATCATTTTTTTAGCTTGTTCTTCAAAAGAACAACAAAT
CAATCCTTTAGGAAGATCTTACGGTAAATTT$_{64}$AACGATAACGATCCTTTAAAACT$_7$TGGTTCAAAACCTACACCCCCTG
TCAAACAAAAAACACCAAGCTTGGTAGAAGGTAAAAAATTTCCCGCCATACCACTTGTCCCACCTGTAATCACTCCTAAT
ACCTTTAAAGGAGATAATGCCGTCAAAGGCCCATTGCCAAGGCTAAAATCTC$_{70}$CAAACGAATTTGCTTCAAATGCTTTA
TACGAAAACACAGGTATGGTAAGTGATTTTGTCACTATTATGAATCCTAATGGAGCATCTTTAACAATCTGGGCTTTAAA
TCCTGGCAATTGGATATGGGGATATAGTTTATTTGCTAGTAGACCTTTTGGAGATGCAAGAGCTTGGCAGCTTATTGAAT
TTCCAAACAATACAGTAATGATTAAAAATGCAAAAACATTTACTTGCTTAAACGCCTATAGAAATGGCATCGTTCATTAT
CCTTGTGATCAAACAAATTTTGCGCAGTTTTGGAGACTTTATC$_{71}$CGATGACTAATGGAGCTTATCAAATTCAAAATTTT
GCCACCCAACA$_{65}$ATGTATACAAACACCTGTTTCAAATGTAATGGAAGAATTTAATTTGAGCTTTTATAATATTTATTTA
ACCGATTGTTTGAAAGAAAAAGAAAAGAATTTGGATAGACAGTGGTATATAGGCGCTCCTATTTAATTTTTTCGCTATGA
AAGGAAGATAATGAAAAAAAATAGTATTTTTGATTTTAAGTTTTAATGTATTATTTGCCGC$_{13}$TTTAGAAAATTACAACAC
CGGAACTTGGAATTTGCAAGGC$_9$TCATCAGCTGCAACTGAAAGCAAATGGAATGTTAGTATAAGACAACTCATAACCGGT
GCAAATCCTATGGATGTTTTAGCTGTTCAAGAAGCGGGGGTTTTACCTAGTACAGCTATGATGACTCCTAGACAGGTACA
ACCCGTGGGCGTGGGTATTCCTATACATGAATACATATGGAATTTAGGCTCTGTATCAAGACCTAGCTCTG$_{30}$TTTATAT
ATATTATTCTAGAGTGGATGTAGGAGCAAATCGTGTGAATTTAGCTATCGTTAGCAGAGTGCAAGCGGATGAAGTTTTTG
TTTTACCCCCTCCAACAGTTGCTTCAAGACCTATTATAGG$_{31}$CATACGCATAGGCAATGA$_{14}$TGCTTTTTTCAATATACAC
GCTCTAGCAAGTGGGGGAAATGACGCAGGAGCCATTGTCGCTGCT$_{32}$GTGGATATGTTTTTTAGAAATAGACCTGATATT
AATTGGATGATTTTAGGCGATTTTAATAGAGAATCAGGCGCCTTAGTAACCTTGCTAGATCCTGACTTAAGAGCACGCAC
TCG$_{33}$CGTAGTTGTTCCGCCTTCTT$_{36}$CTACGCAAACAAGTGGAAGAACGATTGATTATGCTATCACTGGAAATTCCAACA
CTGCAGCTTTATACAACCCACCACCGATAGTT$_{28}$GCGATTTTAGCTTTAGAAGGATTAAGAACCTTTTTGG$_{34}$CTTCAGAT
CATTTTCCTGTAAATTTTAGA$_{10}$AGACCTTAGGAGCTTAATATG$_{35}$AAAAAATTTTTTATTTTATTTTTTGCCCTTTTGAG
CTTTTTGAAAGCAGAGCCTAGCTTGGATGAATTAGCAGACTTTACTCCTATGTTTGCTATAAGATCTTTAGAAACAGGAA
TTTCTTTAAGTCCTTTTAGAAAAACTTCAAAA$_{66}$AGGTTAGAAGATCAAAATTGGTTTTTAAAAGAGATTGTAGCAAATG
ATGAGCTAAAAGCTAGGGATATGCACGCAAAAGA$_{76}$TTTGCCTTTTGGCTATGTTCAGTTTATAAGCCCTAGGGGCGATG
ATATATGCCTAGCTGTTTTAAGTGAAAAAAGTTTTGGCACCAAATCTTGCAAACAAGATTTGCAAGATGGAACAATGCAG
ACTATTTTTCTATCATACCAATGACAAATGGTTCTATACAAATTAGATCTTTAACCAATGGTGGCAATCAATGCATGAG
CACTTTTCCTGACTCTAGTATCGCCATAGAAAATCGCTT$_8$TGGTTTAGG$_{67}$AGAATGCCTTTTGGATCGTTCTATCGTAA
CTGTATTAAGC$_{77}$AAACTTTTCTTTTTCTCCCCTGCTATAATCGAAGCAAGCGCAATTTACTAA

FIG. 18

```
C. fetus cdt ORF
ATGACTAAAATTATTTTCAAGCATATTAAAAATAGTCTTATTTTACTATTTTGTATCGCTCTTTTTAGTGCTTGCTCATC
AAAAACGACAAATGTAAGCACTC₇₂AAAAAATAAATCCATTAGGAAGCATTTTTGGCAAAACG₆₄GATGATCCAGATCCAC
TAAATTTAGGCGATTTTCCAACTCTTCTAACATCAAATTTTACAAATCCTATGCCGACTAGAACGCCATCGCCACTTAA
AAAAGTGGATTTGCCTGTAATGAACTCATTAACACATGGTCCGATGTTTTCAAGTGCTTTTAGTAAACCGGACTTGAATT
TCAAACAACCTACTATCAGTCTACAAGGTATCCCGCCTGATCTATTTGATAGAACAAGCGATTTTATGGTGATAATGGGT
GCAAACGGCGTTGTGATCACTATTTGGTACACATCTCCTGGAAACTGGTTATGGGGCTACTCGCTCTATGAAAGCGGCAA
TTTAGGAGGATATCGTGTTTGGCGTCTAATTTTACTACCAAATAATGAAGTCATGATAGTAAATTTCAACACTCGCACGA
CTTGCATAAATA₇₃CTTATAAAAACGGAGTAATTCACTCACCTTGCAATAAAGATAATCCTTTTCAGAAATTTACGTTTC
GTCCAATGACAAACGGAGCCGTACAAATTTATAACAAAGCTACTAATTGCG₆₅TGCTTGCAAACGCCTGTTAATAATCTA
TTCGGTTTTGACGTTTTTGGGGCGATAAATCTTACGACAAAATGCACTGATACTATCGATCAACAATGGTATTTGCTCCC
GCCGCCGCAAGTTGGAAGACTAT₁₅TTTATTAGGAGTAAAAATGCGAAATGTTATTATGATTATATTTATAGCAACTTTA
GGC₃₈TTTGCAAAACCAGAAGATTATAAAATTGCTACTTGGAATTTGCAAGGC₉AGTTCGGCTATAACCGAAAGCAAATGG
A₄₇ATATAAGCGTACGTCAAATAATTAGCGGTGAAAATCCAGCAGATATATTAGCCGTTCAAGAAGCAGGAAATTTACCT
CAAACCGCTCTTC₃₉CTACAGGTAGAAGCATAAATCAAGGCGGCACGATC₄₀GTAACTGAGCATTTATGGCAGCTAGGCAG
TATATCTAGACCGTTCCAA₄₁GTCTATATATATTATGCTCAAATCGACACAGGGGCAAATAGAGTAAATTTAGCAATCGT
TTCACGCATAAAAGCTGATGAAATCATCATCTTGCCGCCTCCT₄₂ACGGTAGCTTCTCGTCCGCTCATAGGTATAAGAAT
AGGAAACGACGTATTTTTCAACATACACGCTCTAGCAAATGGCGGAGTCGATGCTCCGGCGATAATAAA₁₆TTCAATATT
TGACAGATTTAGAAAATATGCCAAATATCACTTGGATGATTTTAGGCGATTTTAACCGCTCACCTGAGAGTTTAAGA₄₃GG
AACTCTTGGATTAGAAACTC₄₄GCGTCAGAGTAACGTTTTTAACA₃₇CCTCCGGCGCCTACTCAAAGAAGCGGCGGAACGC
TTGACTGGGCTATAGTTGGAAACTCAGCCGGCGATCTTGTCCGAAC₄₅TACGCTTGTAGCAGTATTGATGCTAGCAAACC
TGCGGACTCACCTA₄₆GTTTCGGACCATTTTCCGGTAAATTTTAGA₁₀AAATTTGGAGATAACTAATGAAAGCTTTAGCAA
TAATATTTTTATTTGTAAGCATAAGTTTTGCAAACG₇₈AAAACATAACCGACGCTTTTCAAATACGCAATGCAAACACCG
GAATTCCTATAAATATAAAGCGATTTTCAGGG₆₆CAGTTTAATTACCAAAACTGGTTTTTAAATGATTTAGGAGTAGATC
CTAAGATAAAAAAAGTAGATAAATTTTCAAATTC

CYTOLETHAL DISTENDING TOXINS AND DETECTION OF *CAMPYLOBACTER* BACTERIA USING THE SAME AS A TARGET

CROSS REFERENCES

This application is a 371 National Phase application of International Patent Application Serial No. PCT/JP2004/018042, filed Dec. 3, 2004, which claims priority to Japanese Patent Application No. 2003-408103, filed Dec. 5, 2003, which are incorporated herein by reference in their entirety noting that the current application controls to the extent there is any contradiction with any earlier applications and to which applications we claim priority under 35 USC § 120 and 119.

TECHNICAL FIELD

The present invention relates to the cytolethal distending toxins of *Campylobacter coli* and polynucleotides encoding the same. The present invention also relates to methods for determining the presence of *Campylobacter* bacteria in test samples (such as clinical specimens and foods) by targeting cytolethal distending toxins of *Campylobacter* bacteria, including *Campylobacter coli*.

BACKGROUND ART

*Campylobacter* bacteria are microorganisms that are pathogenic to humans as well as wild and domestic animals and that cause abortion and enteritis in animals and enteritis in humans. *Campylobacter jejuni* and *Campylobacter coli* are known to be causative bacteria of *Campylobacter* infection in humans. These bacteria are often referred to as food poisoning bacteria (Blaser, et al, Ann. Intern. Med., 91:179 (1979); Tauxe, R., American Society for Microbiology, Washington D.C. pg. 9 (1992)).

As of 2000, *Campylobacter* has been classified into 15 species and 9 subspecies. *C. jejuni* constitutes 95 to 99% of the bacteria that are isolated in human diarrhea cases, while other bacterial species, such as *C. coli*, constitutes only a few percent (Takahashi, M. et al, Infectious Diseases Weekly Report Japan, 3(6): 10 (2001)). However, the carriage rate of *C. coli* is extremely high in pigs. In recent years, *Campylobacter* infection has been on an increasing trend with increasing meat imports mainly from Southeast Asia. In particular, the infection from chicken-related food, whose consumption has been growing as a result of problems with beef such as BSE and O-157, has rapidly increased.

In addition, while *Campylobacter fetus* has been known as an abortion-causing bacteria in sheep and bovine, it has only recently been reported to be involved in abortion and premature delivery in humans as well. *C. fetus* infection, resulting from eating raw liver or beef contaminated with *C. fetus*, is associated with symptoms such as sepsis and meningitis. The primary source of *Campylobacter* infection in humans is chicken, which carries the bacteria at high densities in the intestinal tract (Simon, M. S. et al., 2003. *Campylobacter* infection. Diseases of Poultry, Iowa State Press, 615-630).

*Campylobacter* bacteria are generally distributed at a high density in the digestive tract of animals, such as bovine, sheep, pig, and chicken, and thus recognized as causative bacteria of zoonosis. Most campylobacteriosis is thought to be caused by chicken. Infection may arise through direct contact with the above animals or their excrement, or through intake of or during processing of food, drinking water, milk, and such contaminated with the excrement. Furthermore, infection cases in facilities such as newborn nurseries have also been reported (Japanese Journal of Pediatric Medicine, 29:1219-1222 (1997)).

Campylobacteriosis has a long incubation period, ranging 3 to 7 days. It is characterized by gastroenteritis symptoms, such as diarrhea (sometimes, bloody mucous diarrhea), abdominal pain, fever, nausea, vomiting, headache, chills, and feebleness. Although the lethality is low, newborn babies may develop systemic infection, such as sepsis and meningitis. In most cases, recovery takes several days to about one week. The general prognosis has a favorable course except in some immunodeficiency patients. However, it has been reported in recent years that patients may develop Guillain-Barre syndrome or Fischer syndrome, which are autoimmune diseases, after campylobacteriosis. The cases developed following campylobacteriosis generally tend to become severe, and the remission rate after one year of the onset is only about 60%.

Chemotherapy using antibiotics is performed for severe conditions or cases complicated by sepsis. The first choice drug is a macrolide, such as erythromycin. Due to natural resistance, cephem antibiotics are not expected to have therapeutic effects. Meanwhile, the increase in the number of bacteria resistant to new quinolone antibiotics has become a problem in recent years. Rapid identification of causative microorganisms after infection is important to conduct an appropriate treatment for campylobacteriosis and to prevent the expansion of infection by revealing the infection route. However, it is difficult to diagnose campylobacteriosis based on clinical symptoms alone, much less to identify *Campylobacter* and its species.

*Campylobacter* bacteria are microaerophiles. A culture of the bacteria requires a special medium such as Skirrow's medium, and a special apparatus (anaerobic jar or the like) to maintain the oxygen concentration at 3 to 10% for the absolute microaerophilic condition. In addition, the culture is time-consuming (2 to 3 days) as compared with other bacteria. Thus, it is difficult to achieve and maintain an isolation culture of *Campylobacter* bacteria. Furthermore, since *Campylobacter* bacteria easily die in the air, they must be tested within 2 to 3 hours after sample collection. Furthermore, since the incubation period of campylobacteriosis is long (3 to 7 days), the bacteria often cannot be isolated when bacterial identification in any foods concerned is carried out after the onset of the symptoms. Furthermore, *Campylobacter* bacteria have very strong infectivity, and have been reported to establish infection with only several hundreds of cells. Thus, it is extremely difficult to identify the source of infection.

One method of discriminative diagnosis between *C. jejuni* and *C. coli* involves testing hippurate hydrolysis. Specifically, the method is based on the fact that *C. jejuni* has the ability to hydrolyze hippurate while *C. coli* does not. However, this method is not exact because there some hippurate-negative *C. jejuni* species are known in the art (Totten, et al, J. Clin. Microbiol., 25: 1747 (1987)). Thus, the presence of *Campylobacter* bacteria can be confirmed only by estimating the presence of the bacteria from food intake history and symptoms, and by examining morphological and biological features of bacteria from colonies obtained by feces culture, which requires several days.

Thus, attempts have been made to identify *Campylobacter* bacteria and detect its toxin genes using, as rapid diagnostic methods that don't require cultivation, genetic diagnostic methods which utilize a DNA probe method or a PCR method using oligonucleotides. For example, the gene encoding rRNA has been generally used as a probe for *Campylobacter* bacteria (Japanese Patent Application Kokai Publication No. (JP-A) S62-228096 (unexamined, published Japanese patent application)). The sequences of *Campylobacter* rRNA genes have already been published (Romaniuk, P. J. et al, *J. Bacteriol.*, 169: 2173 (1987)). In addition, nucleic acid fragments for detecting *Campylobacter* bacteria are also known (JP-A H2-84200; JP-A H2-154700; JP-A H3-112498; JP-A H6-90795; JP-A H6-90796). However, while these sequences may be used to detect *C. jejuni* and/or *C. coli*, they are not adequate to detect other *Campylobacter* bacteria. Furthermore, the current level of specificity is not sufficient.

A method for identifying *C. jejuni* by PCR, using oligonucleotides selected from the flaA gene of *C. coli* VC167, has also been reported (Oyofo, et al, J. Clin. Microbiol., 30: 2613 (1992)). Furthermore, the use of oligonucleotide primers to amplify a target sequence of superoxide dismutases of *C. jejuni* and *C. coli* has been reported in the literature (Romaniuk, P. J. et al, J. Bacteriol., 169: 2173 (1987)). However, these methods are incapable of discriminating between *C. jejuni* and *C. coli*.

Meanwhile, pathogenic factors of *Campylobacter* are being studied actively. Various factors, such as cell invasiveness, flagellin, and cholera toxin-like enterotoxin, have been reported as pathogenic factors of *Campylobacter* bacteria (Mizuno, K. et al, Microbios., 78: 215 (1994); Suzuki, S. et al, FEMS Immunol. Med. Microbiol., 8: 207 (1994)). Recently, cytolethal distending toxin (CDT) was discovered as a toxic factor from *C. jejuni* (Pickett, C. et al. Infect. Immun., 64: 2070 (1996)), and its relevance to the pathogenicity has attracted attention. For example, diarrheagenicity of the toxin has been reported in an animal model using recombinant *E. coli* that produces CDT of Shiga's *bacillus* (*Shigella dysenteriae*) (Infect. Immun., 65: 428-433 (1997)).

CDT is a holotoxin composed of three subunits, called cdtA, cdtB, and cdtC, which are encoded by genes arranged in tandem. The active center of the toxin is in the cdtB subunit having type I deoxyribonuclease-like activity, while the cdtA and cdtC subunits are thought to be involved in the adhesion to target cells. When the holotoxin acts on cells, the cells are distended, i.e. swollen, and finally killed. The toxin is thus named "cytolethal distending toxin".

The molecular mechanism is believed to be as follows. The cdtB subunit that constitutes the active center of the toxin translocates into a cell nucleus, and introduces nicks into chromosomal DNA by its type I deoxyribonuclease activity, thereby inducing DNA-damage response. The cell then arrests the cell cycle at G2/M phase to activate the gene repair system, and is then distended and killed (Science, 290: 354-357 (2000)). Furthermore, CDT has been found to act on a broad range of cells, including epithelial cells and immune cells. In particular, CDT is believed to act on human lymphocytes and induce apoptosis in them, which allows easy escape from immunity (J. Biol. Chem., 276: 5296-5302 (2001)).

As described above, CDT has a unique molecular mechanism that is not found in the other toxins previously known. To date, the complete nucleotide sequence of CDT among *Campylobacter* bacteria has been determined for only *C. jejuni* (Pickett, C. et al. Infect. Immun., 64: 2070 (1996)).

DISCLOSURE OF THE INVENTION

Problems to Be Solved by the Invention

As described in detail above, there is a need in the art for the rapid diagnosis of *Campylobacter* infection, despite the fact that the pathogenic factors of *Campylobacter* bacteria have not been fully elucidated. Conventionally, PCR primers for identifying bacterial species based on the serotype thereof, common primers for testing CDT production, and such have been used (J. Applied Microbiol., 94: 1003-1014 (2003)). However, such methods require the step of an enrichment culture, making the rapid detection of *Campylobacter* bacteria impossible.

Thus, an objective of the present invention is to provide CDT of *C. coli*, a *Campylobacter* species whose CDT nucleotide sequence has yet to be elucidated, and provide the polynucleotide encoding the CDT, in order to enable the rapid detection of *Campylobacter* bacteria through genetic diagnosis. Another objective of the present invention is to provide CDT of *C. fetus*, whose CDT nucleotide sequence has also yet to be elucidated, and provide the polynucleotide encoding the CDT.

Furthermore, another objective of the present invention is to provide methods that enable the rapid detection of *Campylobacter* bacteria, which target CDTs of *Campylobacter* bacteria, including *C. coli* and *C. fetus*, based on the findings obtained from the nucleotide sequences of *C. coli* and *C. fetus*.

Means to Solve the Problems

When cloning of the CDT genes is carried out using the restriction enzyme HindIII, its full length cannot be isolated because its coding region contains HindIII sites. Meanwhile, common restriction enzymes, such as EcoRI, PstI, KpnI, XbaI, BamHI, SalI, and XhoI, do not yield fragments with an adequate length (3 to 5 kb) for cloning of the cdt genes. As a result of various studies, the present inventors finally succeeded in cloning the complete cdt genes without any cleavage in their internal sequences by selecting a partial digestion condition wherein the cdt gene is not completely digested with HindIII.

The present inventors also compared the *C. coli* CDT with CDTs of *C. jejuni* and *C. fetus* and developed primers common to the three *Campylobacter* bacteria and primers specific to each of the bacteria. The inventors then demonstrated that these primers were applicable to multiplex PCR that simultaneously allows for rapid and convenient determination of the presence of *Campylobacter* CDT and identification of species, and that they can also be used in PCR-RFLP-based typing.

Specifically, the present invention encompasses the following technical embodiments:

(1) a polynucleotide encoding a cytolethal distending toxin, which is any one of:

(a) a polynucleotide encoding a polypeptide comprising the amino acid sequence of any one of SEQ ID NOs: 2 to 4;

(b) a polynucleotide comprising the coding region in the nucleotide sequence of SEQ ID NO: 1;

(c) a polynucleotide encoding a polypeptide comprising an amino acid sequence with a substitution, deletion, addition, and/or insertion of one or more amino acids in any one of the amino acid sequences of SEQ ID NOs: 2 to 4; and (d) a polynucleotide that hybridizes to DNA comprising the nucleotide sequence of SEQ ID NO: 1 under a stringent condition;

(2) a vector comprising the polynucleotide of (1);

(3) a host cell carrying the polynucleotide of (1) or the vector of (2);

(4) a polypeptide encoded by the polynucleotide of (1);

(5) a method for producing the polypeptide of (4), which comprises the step of culturing the host cell of (3) and collecting the produced polypeptide from the host cell or the culture supernatant;

(6) an antibody that binds to the polypeptide of (4);

(7) a method for detecting the presence of *Campylobacter coli, Campylobacter jejuni*, and *Campylobacter fetus* in a test sample, wherein the method comprises the steps of:

(a) conducting a polymerase chain reaction on the test sample using a mixture of primer pairs specific to each of genomic DNAs encoding the cytolethal distending toxins of these bacteria; and (b) determining the presence of these bacteria based on the presence or molecular weight of amplified fragments from the genomic DNAs encoding the cytolethal distending toxins of the bacteria;

(8) a method for detecting the presence of *Campylobacter coli, Campylobacter jejuni*, and *Campylobacter fetus* in a test sample, wherein the method comprises the steps of:

(a) conducting a polymerase chain reaction on the test sample using a common primer pair which can amplify genomic DNAs encoding the cytolethal distending toxins of these bacteria;

(b) conducting a polymerase chain reaction using the genomic DNA amplified in step (a) as a template and a mixture of primer pairs specific to each of the genomic DNAs encoding cytolethal distending toxins of the bacteria; and (c) determining the presence of the bacteria based on the presence or molecular weight of amplified fragments from the genomic DNAs encoding the cytolethal distending toxins of the bacteria;

(9) the method of (8), wherein the common primer pair is a primer pair selected from SEQ ID NOs: 7 to 10 and 47 to 50, or a primer pair which can amplify the same genomic DNA region as amplified with said primer pair;

(10) the method of (7) or (8), wherein the method uses (a) to (c) as the mixture of specific primer pairs:

(a) a primer pair selected from SEQ ID NOs: 13, 14, and 28 to 36 to amplify the genomic DNA encoding the cytolethal distending toxin of *Campylobacter coli*, or a primer pair which can amplify the same genomic DNA region as amplified with said primer pair;

(b) a primer pair selected from SEQ ID NOs: 11, 12, and 17 to 27 to amplify the genomic DNA encoding the cytolethal distending toxin of *Campylobacter jejuni*, or a primer pair which can amplify the same genomic DNA region as amplified with said primer pair; and (c) a primer pair selected from SEQ ID NOs: 15, 16, and 37 to 46 to amplify the genomic DNA encoding the cytolethal distending toxin of *Campylobacter fetus*, or a primer pair which can amplify the same genomic DNA region as amplified with said primer pair;

(11) a method for detecting the presence of *Campylobacter coli, Campylobacter jejuni*, and *Campylobacter fetus* in a test sample, wherein the method comprises the steps of:

(a) conducting a polymerase chain reaction on the test sample using a common primer pair which can amplify genomic DNAs encoding the cytolethal distending toxins of these bacteria;

(b) digesting the genomic DNAs amplified in step (a) with a restriction enzyme; and (c) determining the presence of the bacteria based on the molecular weight of a DNA fragment resulting from the digestion;

(12) the method of (11), wherein the restriction enzyme is selected from the group consisting of: Sau3AI, Dsa I, Mbo I, Rsa I, EcoRI, Hinf I, Nde I, Pst I, Xba I, and Xho II;

(13) the method of (11), wherein the common primer pair is a primer pair selected from SEQ ID NOs: 7 to 10 and 47 to 50, or a primer pair which can amplify the same genomic DNA region as amplified with said primer pair;

(14) a kit used in the method of (7), which comprises an instruction manual and a mixture of primer pairs specific to each of genomic DNAs encoding the cytolethal distending toxins of *Campylobacter coli, Campylobacter jejuni*, and *Campylobacter fetus*;

(15) the kit of (14) wherein the mixture of specific primer pairs is as follows:

(a) a primer pair selected from SEQ ID NOs: 13, 14, and 28 to 36 to amplify the genomic DNA encoding the cytolethal distending toxin of *Campylobacter coli*, or a primer pair which can amplify the same genomic DNA region as amplified with said primer pair;

(b) a primer pair selected from SEQ ID NOs: 11, 12, and 17 to 27 to amplify the genomic DNA encoding the cytolethal distending toxin of *Campylobacter jejuni*, or a primer pair which can amplify the same genomic DNA region as amplified with said primer pair; and (c) a primer pair selected from SEQ ID NOs: 15, 16, and 37 to 46 to amplify the genomic DNA encoding the cytolethal distending toxin of *Campylobacter fetus*, or a primer pair which can amplify the same genomic DNA region as amplified with said primer pair;

(16) a kit used in the method which comprises an instruction manual and:

(a) a mixture of primer pairs specific to each of genomic DNAs encoding cytolethal distending toxins of *Campylobacter coli, Campylobacter jejuni*, and *Campylobacter fetus*; or (b) a common primer pair which can amplify the genomic DNAs encoding the cytolethal distending toxins of *Campylobacter coli, Campylobacter jejuni*, and *Campylobacter fetus*;

(17) the kit of (16), wherein the mixture of specific primer pairs is as follows:

(a) a primer pair selected from SEQ ID NOs: 13, 14, and 28 to 36 to amplify the genomic DNA encoding the cytolethal distending toxin of *Campylobacter coli*, or a primer pair which can amplify the same genomic DNA region as amplified with said primer pair;

(b) a primer pair selected from SEQ ID NOs: 11, 12, and 17 to 27 to amplify the genomic DNA encoding the cytolethal distending toxin of *Campylobacter jejuni*, or a primer pair which can amplify the same genomic DNA region as amplified with the primer pair; and (c) a primer pair selected from SEQ ID NOs: 15, 16, and 37 to 46 to amplify the genomic DNA encoding the cytolethal distending toxin of *Campylobacter fetus*, or a primer pair which can amplify the same genomic DNA region as amplified with the primer pair;

(18) the kit of (16), wherein the common primer pair is a primer pair selected from SEQ ID NOs: 7 to 10 and 47 to 50, or a primer pair which can amplify the same genomic DNA region as amplified with said primer pair;

(19) a kit used in the method of (11), which comprises an instruction manual and a common primer pair which can amplify genomic DNAs encoding the cytolethal distending toxins of *Campylobacter coli, Campylobacter jejuni,* and *Campylobacter fetus*; and

(20) the kit of (19), wherein the common primer pair is a primer pair selected from SEQ ID NOs: 7 to 10 and 47 to 50, or a primer pair which can amplify the same genomic DNA region as amplified with said primer pair.

Herein, the phrase "cytolethal distending toxins" (CDTs or CLDTs) refers to toxic factors belonging to the group of proteinaceous type A-B holotoxins. The cytolethal distending toxin has a subunit structure consisting of three subunits A, B, and C. It is believed that subunit B is the active site unit of the toxin and subunits A and B are involved in cell adhesion. When the toxin acts on cells, it causes cell deformation such as cell swelling, and finally leads to cell death. Cell deformation such as cell swelling is also observed when heat-labile enterotoxin (LT), which is produced by toxigenic *E. coli*, or the like is experimentally allowed to act on cells. When the toxin is removed, however, the cells recover and survive. In contrast, cells do not recover but instead are killed, even when CDT is removed.

The term "polynucleotide" as used herein refers to a ribonucleotide or deoxyribonucleotide, or a polymer made up of a number of bases or base pairs. Polynucleotides include single-stranded DNAs as well as double-stranded DNAs. Polynucleotides herein may include both unmodified, naturally-occurring polynucleotides and modified polynucleotides. Tritylated bases and special bases, such as inosine, are examples of modified bases.

The term "polypeptide" as used herein refers to a polymer made up of a number of amino acids. Therefore, oligopeptides and proteins are also included within the concept of polypeptides. Polypeptides include both unmodified, naturally-occurring polypeptides and modified polypeptides. Examples of polypeptide modifications include acetylation; acylation; ADP-ribosylation; amidation; covalent binding with flavin; covalent binding with heme moieties; covalent binding with nucleotides or nucleotide derivatives; covalent binding with lipids or lipid derivatives; covalent binding with phosphatidylinositols; cross-linkage; cyclization; disulfide bond formation; demethylation; covalent cross linkage formation; cystine formation pyroglutamate formation; formylation; g-carboxylation; glycosylation; GPI-anchor formation; hydroxylation; iodination; methylation; myristoylation; oxidation; proteolytic treatment; phosphorylation; prenylation; racemization; selenoylation; sulfation; transfer RNA-mediated amino acid addition to a protein such as arginylation; ubiquitination; and the like.

The term "isolate" as used herein refers to a substance (for example, a polynucleotide or polypeptide) removed from its original environment (for example, the natural environment for a naturally-occurring substance) and "artificially" changed from its natural state. "Isolated" compounds refer to compounds including those present in samples that are substantially abundant with a subject compound, and/or those present in samples wherein the subject compound is partly or substantially purified. Herein, the term "substantially purified" refers to compounds (for example, polynucleotides or polypeptides) that are isolated from the natural environment and in which at least 60%, preferably 75%, and most preferably 90% of the other components associated with the compound in nature are absent.

The term "mutation" as used herein refers to changes to the amino acids of an amino acid sequence, or changes to the bases in a nucleotide sequence (that is, substitution, deletion, addition, or insertion of one or more amino acids or nucleotides). Therefore, the term "mutant" as used herein refers to amino acid sequences wherein one or more amino acids are changed, or nucleotide sequences wherein one or more nucleotides are changed. Nucleotide sequence changes in the mutant may change the amino acid sequence of the polypeptide encoded by the standard polynucleotide, or not. The mutant may be one that exists in nature, such as an allelic mutant, or one not yet identified in nature. The mutant may be conservatively altered, wherein substituted amino acids retain structural or chemical characteristics similar to those of the original amino acid. Rarely, mutants may be substituted non-conservatively. Computer programs known in the art, such as DNA STAR software, can be used to decide which or how many amino acid residues to substitute, insert, or delete without inhibiting biological or immunological activities.

"Deletion" is a change to either an amino acid sequence or nucleotide sequence, wherein one or more amino acid residues or nucleotide residues are missing as compared with the amino acid sequence of a naturally occurring cytolethal distending toxin polypeptide, or a nucleotide sequence encoding the same.

"Insertion" or "addition" is a change to either an amino acid sequence or nucleotide sequence, wherein one or more amino acid residues or nucleotide residues are added as compared with the amino acid sequence of a naturally-occurring cytolethal distending toxin polypeptide, or a nucleotide sequence encoding the same.

"Substitution" is a change to either an amino acid sequence or nucleotide sequence, wherein one or more amino acid residues or nucleotide residues are changed to different amino acid residues or nucleotide residues, as compared to the amino acid sequence of a naturally-occurring cytolethal distending toxin polypeptide, or a nucleotide sequence encoding the same.

The term "hybridize" as used herein refers to a process wherein a nucleic acid chain binds to its complementary chain through the formation of base pairs.

BRIEF DESCRIPTION OF THE DRAWINGS

FIG. 1 is a photograph showing a result of PCR with GNW and LPF-D primers using *C. coli* Co 1-192 cell extract as a template. Arrow I indicates the bands resulting from amplification of the cdt region (about 1.5 Kb); the bands (800 bp) of arrow 2 are secondary bands derived from cdtB, which were amplified since the GNW primers were mixed primers.

FIG. 2 is a photograph showing a result of hybridization after digestion of genomes from *C. coli* Co 1-192 cells with the restriction enzyme HindIII.

FIG. 3 is a photograph showing a result of PCR using common primer pair 1. CDT-derived bands are seen at about 1.9 kbp in lanes 2 to 6.

FIG. 4 is a photograph showing a result of PCR for various *C. jejuni* strains using common primer pair 2. CDT-derived bands are seen at about 720 bp.

FIG. 5 is a photograph showing a result of PCR for various *C. jejuni* and *C. coli* strains using common primer pair 2.

FIG. 6 is a photograph showing a result of PCR for *C. jejuni, C. coli* and *C. fetus* strains using common primer pair 2.

FIG. 7 is a photograph showing a result of multiplex PCR for *C. jejuni, C. coli*, and *C. fetus* strains using specific primers. CDT-specific amplified fragments unique to each species were detected (*C. jejuni,* 750 bp; *C. coli,* 400 bp; *C. fetus,* 530 bp).

Figure 11:
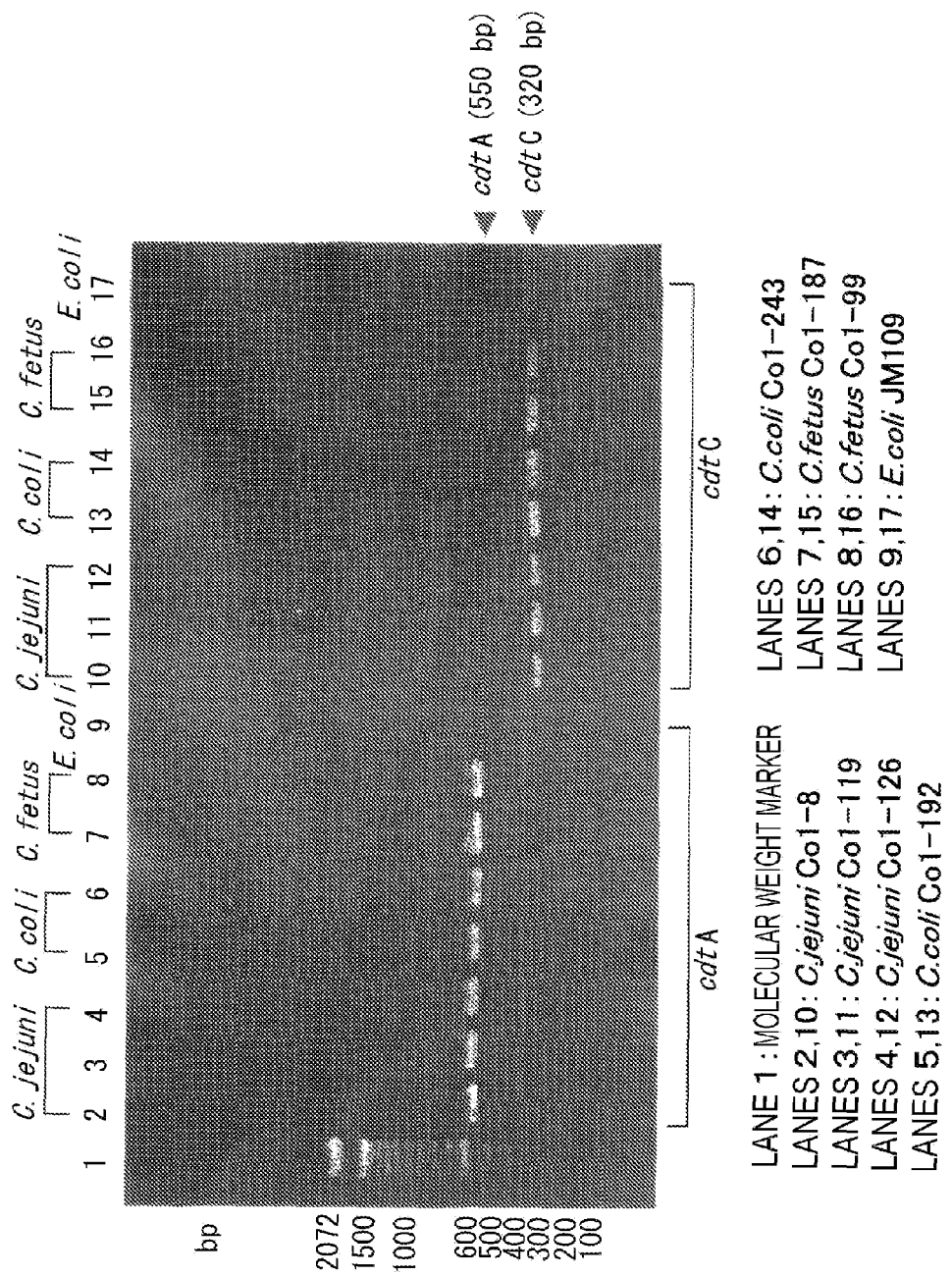

FIG. 11 is a photograph showing a result of PCR using common primers for cdtA and cdtC. Bands derived from cdtA are seen at about 550 bp in lanes 2 to 8; and bands derived from cdtC are seen at about 320 bp in lanes 10 to 16.

FIG. 12 is a set of photographs showing a result of PCR for various strains of *Campylobacter* species using common primers for cdtA. Bands derived from cdtA are seen at about 550 bp.

FIG. 13 is a set of photographs showing a result of PCR for various strains of *Campylobacter* species using common primers for cdtC. Bands derived from cdtC are seen at about 320 bp.

Figure 14:
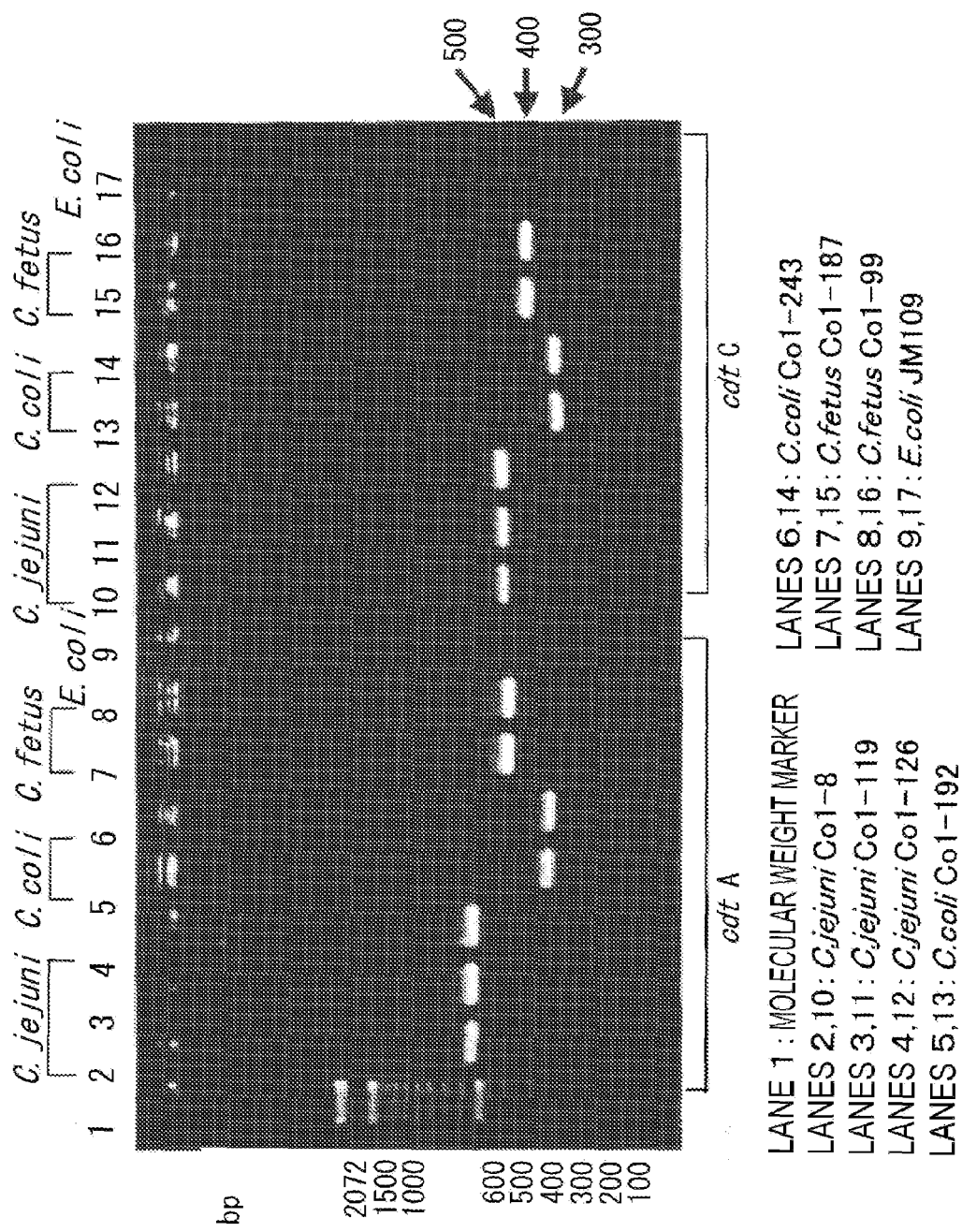

FIG. 14 is a photograph showing a result of multiplex PCR for *C. jejuni*, *C. coli*, and *C. fetus* strains using primers specific to cdtA and cdtC. Amplified fragments specific to cdtA (*C. jejuni*, 630 bp; *C. coli*, 330 bp; *C. fetus*, 490 bp) and to cdtC (*C. jejuni*, 500 bp; *C. coli*, 400 bp; *C. fetus*, 300 bp) unique to each species are detected.

FIG. 15 is a set of photographs showing a result of multiplex PCR for *C. jejuni*, *C. coli*, and *C. fetus* strains using cdtA-specific primers. CdtA-specific amplified fragments unique to each species were detected.

Figure 16:
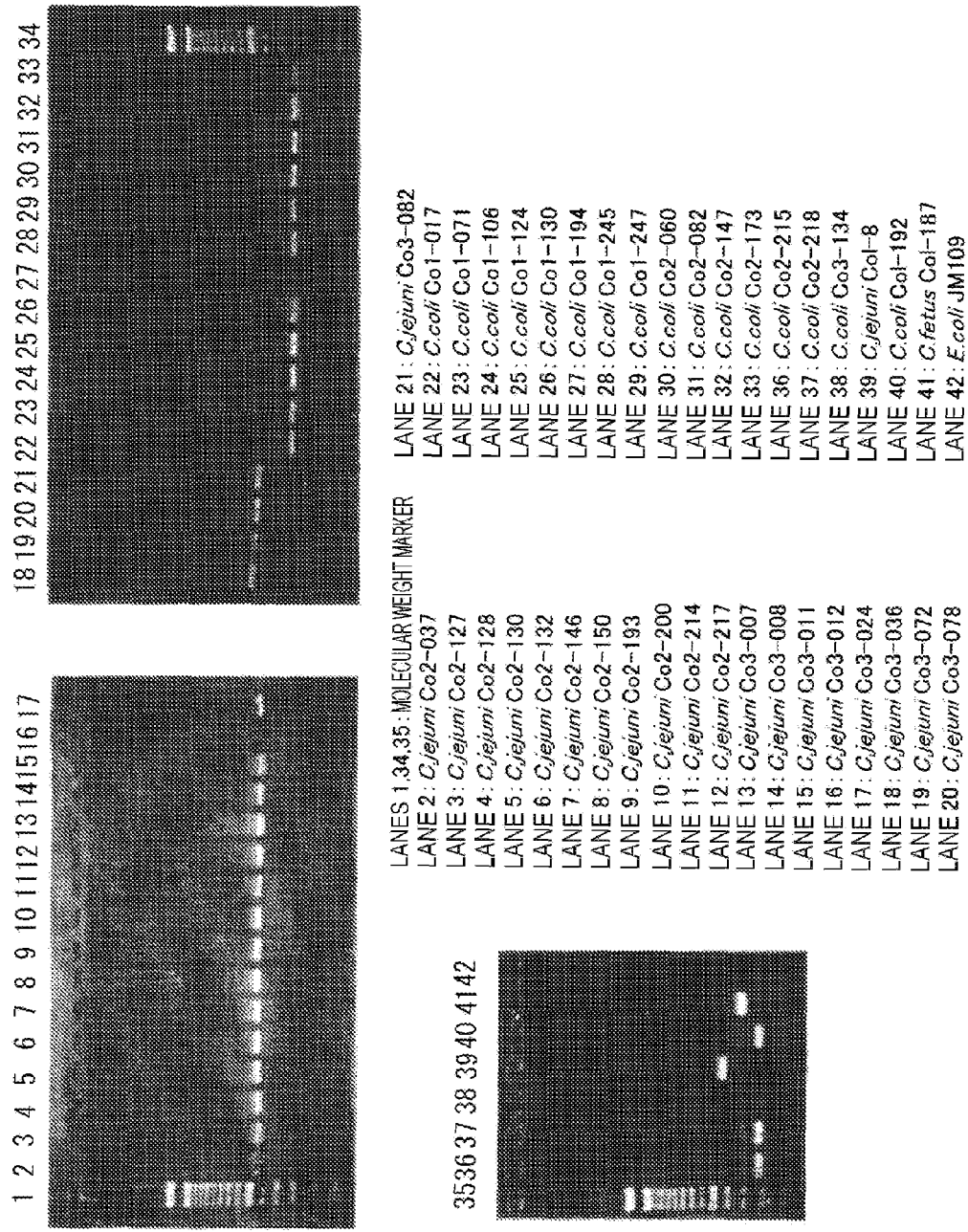

FIG. 16 is a set of photographs showing a result of multiplex PCR for *C. jejuni*, *C. coli*, and *C. fetus* strains using cdtC-specific primers. CdtC-specific amplified fragments unique to each species were detected.

FIG. 17 shows the ORF of *C. jejuni* CDT and the primer annealing regions.

FIG. 18 shows the ORF of *C. coli* CDT and the primer annealing regions.

FIG. 19 shows the ORF of *C. fetus* CDT and the primer annealing regions.

BEST MODE FOR CARRYING OUT THE INVENTION

Polynucleotide

The present invention provides a polynucleotide encoding the cytolethal distending toxin of *Campylobacter coli*. The polynucleotide sequence encoding the cytolethal distending toxin of *C. coli*, which was identified by the present inventors and is encompassed by the present invention, is set forth in SEQ ID NO: 1. The amino acid sequences of the three polypeptides encoded by the polynucleotide are set forth in SEQ ID NOs: 2 to 4. SEQ ID NOs: 2, 3, and 4 correspond to the amino acid sequences of cdtA, cdtB, and cdtC, respectively.

The present invention also provides a polynucleotide encoding the cytolethal distending toxin of *Campylobacter fetus*. The polynucleotide sequence encoding the cytolethal distending toxin of *C. fetus*, which was identified by the present inventors and is encompassed by the present invention, is set forth in SEQ ID NO: 51. The amino acid sequences of the three polypeptides encoded by the polynucleotide are set forth in SEQ ID NOs: 52 to 54; SEQ ID NOs: 52, 53, and 54 correspond to the amino acid sequences of cdtA, cdtB, and cdtC, respectively.

The polynucleotides of the present invention include polynucleotides encoding the polypeptides having the amino acid sequences of SEQ ID NOs: 2 to 4; polynucleotides including the coding region in the nucleotide sequence of SEQ ID NO: 1, i.e. any one of the nucleotide sequences of position 1 to 777, 802 to 1605, and 1615 to 2187 in SEQ ID NO: 1; and polynucleotides that have a nucleotide sequence different from the nucleotide sequence of SEQ ID NO: 1 but yet encode the polypeptides having the amino acid sequences of SEQ ID NOs: 2 to 4 due to the degeneracy of the genetic code.

The polynucleotides of the present invention also include polynucleotides encoding the polypeptides having the amino acid sequences of SEQ ID NOs: 52 to 54; polynucleotides including the coding region in the nucleotide sequence of SEQ ID NO: 51, i.e. any one of the nucleotide sequences of position 1 to 702, 778 to 1629, and 1615 to 2187 in SEQ ID NO: 51; and polynucleotides that have a nucleotide sequence different from the nucleotide sequence of SEQ ID NO: 51 but yet encode the polypeptides having the amino acid sequences of SEQ ID NOs: 52 to 54 due to the degeneracy of the genetic code.

The polynucleotides of the present invention further include polynucleotides that encode polypeptides functionally equivalent to polypeptides encoded by the above polynucleotides and have a nucleotide sequence with an identity of at least 40% or higher, preferably 60% or higher, more preferably 80% or higher, even more preferably 90% or higher, still more preferably 95% or higher, yet more preferably 97% or higher (for example, 98 to 99%) to the entire sequence of the polynucleotide. The nucleotide sequence identity can be determined, for example, using the algorithm BLAST by Karlin and Altschul (Proc. Natl. Acad. Sci. USA 87:2264-2268, 1990; Proc. Natl. Acad. Sci. USA 90:5873-5877, 1993). A program called BLASTN has been developed based on this algorithm (Altschul et al. J. Mol. Bio1.215:403-410, 1990). When nucleotide sequences are analyzed by BLASTN, the parameters are set, for example, as follows: score=100; wordlength=12. When BLAST and Gapped BLAST programs are used, default parameters are used for each program. The specific techniques for these analytical methods are known (http://www.ncbi.nlm.nih.gov.). The polynucleotides of the present invention include polynucleotides having nucleotide sequences complementary to the above polynucleotide sequences.

The polynucleotides of the present invention can be obtained through standard cloning and screening methods from natural sources, such as genomic DNA in bacterial cells. Alternatively, the polynucleotides can be obtained from cDNA libraries derived from mRNA in bacterial cells. The polynucleotides can also be synthesized using known techniques that are commercially available.

Polynucleotides having nucleotide sequences with significant homology to the polynucleotide sequences identified by the present inventors (e.g., SEQ ID NOs: 1 and 51) can be prepared, for example, using hybridization techniques (Current Protocols in Molecular Biology edit. Ausubel et al. (1987) Publish. John Wiley & Sons Section 6.3-6.4) and gene amplification techniques (PCR) (Current protocols in Molecular Biology edit. Ausubel et al. (1987) Publish. John Wiley & Sons Section 6.1-6.4). Specifically, based on the polynucleotide sequences identified by the present inventors (e.g., SEQ ID NOs: 1 and 51) or portions thereof, DNA highly homologous to the sequences can be isolated using known hybridization techniques. Alternatively, polynucleotides highly homologous to the polynucleotide sequences can be isolated by gene amplification techniques, using primers designed based on portions of the polynucleotide sequences identified by the present inventors (e.g., SEQ ID NOs: 1 and 51). Thus, the present invention includes polynucleotides that hybridize to the polynucleotide having the nucleotide sequence of SEQ ID NO: 1 under a stringent condition. A stringent hybridization condition is typically the condition of 1×SSC, 0.1% SDS, and 37° C. A more stringent condition is the condition of 0.5×SSC, 0.1% SDS, and 42° C. A still more stringent condition is the condition of 0.2×SSC, 0.1% SDS, and 65° C. As the hybridization condition is more stringent as described above, DNA having higher homology to the probe sequence is expected to be isolated. However, the above combinations of SSC, SDS, and temperature condition are only exemplary. Those skilled in the art can achieve the same stringency as described above by appropriately combining the above or other factors (for example, probe concentration and length, and reaction time for hybridization) which determines the degree of hybridization stringency.

Polynucleotides including the nucleotide sequences with significant homology to the polynucleotide sequences identified by the present inventors can also be prepared by methods for introducing mutations into the nucleotide sequences of SEQ ID NOs: 1 and 51 (for example, site directed mutagenesis (Current Protocols in Molecular Biology edit. Ausubel et al. (1987) Publish. John Wiley & Sons Section 8.1-8.5)). Such polynucleotides may also be generated by naturally-occurring mutations. The present invention includes polynucleotides encoding the polypeptides having an amino acid sequence wherein one or more amino acids is substituted, deleted, inserted and/or added in the amino acid sequences of SEQ ID NOs: 2 to 4 or 52 to 54 due to such nucleotide sequence mutations.

When the polynucleotides of the present invention are used to produce the polypeptides of the present invention, the polynucleotides include coding sequences for the mature polypeptides or fragments thereof alone, or coding sequences for the mature polypeptides or fragments thereof which are located in the same reading frame as other coding sequences (for example, leader or secretory sequence, pre-, pro-, or prepro-protein sequence, or sequences encoding other fusion peptide portions). For example, marker sequences that facilitate purification of fusion polypeptides may be encoded. In this embodiment of the present invention, preferred examples of marker sequences include, for example, hexa-histidine peptide or Myc tag which is provided by pcDNA3.1/Myc-His vector (Invitrogen) and described in Gentz et al., Proc. Natl. Acad. Sci. USA (1989) 86:821-824. The polynucleotide may also include 5' and 3' non-coding sequences, for example, transcribed but untranslated sequences, splicing and polyadenylation signals, ribosome-binding site, and mRNA-stabilizing sequence.

<Polypeptide>

The present invention provides the polypeptide of the cytolethal distending toxin of *Campylobacter coli* identified by the present inventors. The present invention also provides polypeptides functionally equivalent to the polypeptide identified by the present inventors. Herein, "functionally equivalent" means that a polypeptide of interest has characteristics of cytolethal distending toxin equivalent to that of the polypeptide identified by the present inventors.

The present invention also provides the polypeptide of the cytolethal distending toxin of *Campylobacter fetus* identified by the present inventors. The present invention further provides polypeptides functionally equivalent to the polypeptide identified by the present inventors. Herein, "functionally equivalent" means that a polypeptide of interest has characteristics of cytolethal distending toxin equivalent to that of the polypeptide identified by the present inventors.

Introducing mutations into the amino acid sequence of proteins is one means for preparing polypeptides functionally equivalent to the polypeptides identified by the inventors. Such methods include, for example, site-directed mutagenesis (Current Protocols in Molecular Biology, edit. Ausubel et al. (1987) Publish. John Wiley & Sons Section 8.1-8.5). Amino acid mutation in polypeptides may also occur in nature. The present invention includes mutant proteins, regardless of whether artificially or naturally produced, that include the amino acid sequence identified by the inventors (e.g., SEQ ID NO: 2 to 4 and 52 to 54), wherein one or more amino acid residues are altered by substitution, deletion, insertion, and/or addition, yet which are functionally equivalent to the polypeptides identified by the present inventors.

From the viewpoint of conserving the protein's functions, an amino acid residue used for substitution preferably has properties similar to the substituted amino acid residue (conservative substitution). For example, Ala, Val, Leu, Ile, Pro, Met, Phe, and Trp are all classified as non-polar amino acids, and are considered to have similar properties. Further, examples of uncharged amino acids are Gly, Ser, Thr, Cys, Tyr, Asn, and Gln. Moreover, examples of acidic amino acids are Asp and Glu, and those of basic amino acids are Lys, Arg, and His.

There are no limitations as to the number and site of the amino acid mutations of these polypeptides, so long as the mutated polypeptides retain a function of the original polypeptide. The number of mutations may be typically less than 10%, preferably less than 5%, and more preferably less than 1% of the total amino acid residues.

Other means for preparing polypeptides functionally equivalent to the polypeptides identified by the inventors include methods that utilize hybridization techniques or gene amplification techniques. More specifically, those skilled in the art can obtain polypeptides functionally equivalent to the polypeptides determined by the present inventors by isolating highly homologous DNAs from DNA samples derived from organisms of the same or different species using hybridization techniques (Current Protocols in Molecular Biology, edit. Ausubel et al. (1987) Publish. John Wiley & Sons Section 6.3-6.4) based on the DNA sequence encoding the polypeptides identified by the inventors (SEQ ID NO: 1 and 51). Thus, such polypeptides, encoded by DNAs hybridizing to the DNAs encoding the polypeptides identified by the inventors, which are functionally equivalent to the polypeptides identified by the inventors, are also included in the polypeptides of this invention.

Hybridization stringencies required to isolate a DNA encoding a polypeptide functionally equivalent to the polypeptides identified by the inventors are normally "1×SSC, 0.1% SDS, 37° C." or such, with more stringent conditions being "0.5×SSC, 0.1% SDS, 42° C." or such, and even more stringent conditions being "0.2×SSC, 0.1% SDS, 65° C." or such. DNAs with higher homology to the probe sequence are expected to be isolated at higher stringencies. However, the above-mentioned combinations of SSC, SDS, and temperature conditions are only examples, and those skilled in the art can achieve the same stringencies as described above by appropriately combining the above-mentioned factors or other parameters which determine hybridization stringency (for example, probe concentration, probe length, reaction time of hybridization, etc.).

The polypeptides encoded by DNAs isolated using such hybridization techniques normally have amino acid sequences highly homologous to the polypeptides identified by the present inventors. Herein, high homology indicates sequence identity of at least 40% or more, preferably 60% or more, more preferably 80% or more, still more preferably 90% or more, further still more preferably at least 95% or more, and yet more preferably at least 97% or more (for example, 98% to 99%). Homology of amino acid sequences can be determined, for example, using the algorithm BLAST of Karlin and Altschul (Proc. Natl. Acad. Sci. USA 87: 2264-2268 (1990); Proc. Natl. Acad. Sci. USA 90: 5873-5877 (1993)). Based on this algorithm, a program referred to as BLASTX has been developed (Altschul et al., J. Mol. Biol. 215: 403-410 (1990)). When amino acid sequences are analyzed using BLASTX, parameters are set, for example, at score=50 and wordlength=3, while when using BLAST and Gapped BLAST programs, default parameters of each program are used. Specific techniques for these analytical methods are well known in the field.

Gene amplification techniques (PCR) (Current Protocols in Molecular Biology, edit. Ausubel et al. (1987) Publish. John Wiley & Sons Section 6.1-6.4) can be utilized to obtain polypeptides functionally equivalent to the polypeptides isolated by the present inventors, based on DNA fragments isolated as DNAs highly homologous to the DNA sequences encoding the polypeptides isolated by the present inventors. This can be achieved by designing primers based on a part of the DNA sequence encoding the polypeptides identified by the inventors (SEQ ID NO: 1 and 51).

<Polypeptide Fragments>

The present invention also provides fragments of the polypeptides of this invention. These fragments are polypeptides having amino acid sequences that are partly, but not entirely, identical to the above polypeptides of this invention. The polypeptide fragments of this invention usually include eight amino acid residues or more, and preferably twelve amino acid residues or more (for example, 15 amino acid residues or more). Examples of preferred fragments include truncation polypeptides, such as amino acid sequences that lack a series of amino acid residues including either the amino terminus or carboxyl terminus, or two series of amino acid residues, one including the amino terminus and the other including the carboxyl terminus. Furthermore, fragments featuring structural or functional characteristics are also preferable, and include those having α-helix and α-helix forming regions, β-sheet and β-sheet forming regions, turn and turn-forming regions, coil and coil-forming regions, hydrophilic regions, hydrophobic regions, α-amphipathic regions, β-amphipathic regions, variable regions, surface forming regions, substrate-binding regions, and high antigenicity index regions. Biologically active fragments are also preferred. Biologically active fragments mediate the activities of the polypeptides of this invention, and include those that have a similar or improved activity, or a reduced undesirable activity. For example, fragments that are antigenic or immunogenic in animals, especially humans, are included. These polypeptide fragments preferably retain a biological activity, such as antigenicity, of the polypeptides of this invention. Mutants of specific sequences or fragments also constitute an aspect of this invention. Preferred mutants are those that differ from the subject polypeptide due to replacement with conservative amino acids, namely, those in which a residue is substituted with another residue of similar properties. Typical substitutions are those between Ala, Val, Leu, and Ile; Ser and Thr; acidic residues Asp and Glu, Asn, and Gln; basic residues Lys and Arg; or aromatic residues Phe and Tyr.

<Production of Polypeptides>

Polypeptides of this invention may be produced by any appropriate method. Such polypeptides include isolated naturally-occurring polypeptides, and polypeptides which are produced by gene recombination, synthesis, or by a combination thereof. Procedures for producing these polypeptides are well known in the art. Recombinant polypeptides may be prepared, for example, by transferring a vector, inserted with a polynucleotide of the present invention, into an appropriate host cell, and purifying the polypeptide expressed within the resulting transformant. On the other hand, naturally occurring polypeptides can be prepared, for example, using affinity columns wherein antibodies against a polypeptide of this invention (described below) are immobilized (Current Protocols in Molecular Biology, edit. Ausubel et al. (1987) Publish. John Wiley & Sons, Section 16.1-16.19). Antibodies for affinity purification may be either polyclonal or monoclonal antibodies. The polypeptides of this invention may be also prepared by in vitro translation methods (for example, see "On the fidelity of mRNA translation in the nuclease-treated rabbit reticulocyte lysate system." Dasso, M. C. and Jackson, R. J. (1989) NAR 17: 3129-3144), and such. The polypeptide fragments of this invention can be produced, for example, by cleaving the polypeptides of the present invention with appropriate peptidases.

<Probes, Primers>

The present invention provides nucleotides with a chain length of at least 15 nucleotides, which are complementary to a polynucleotide identified by the present inventors (e.g., a polynucleotide having the nucleotide sequence of SEQ ID NO: 1 or a complementary strand thereof, and a polynucleotide having the nucleotide sequence of SEQ ID NO:51 or a complementary strand thereof). Herein, the term "complementary strand" is defined as the other strand of a double-stranded nucleic acid composed of A:T (A:U in case of RNA) and G:C base pairs. In addition, the term "complementary" encompasses not only complete matching within a continuous region of at least 15 sequential nucleotides, but also homology of at least 70%, preferably at least 80%, more preferably 90%, and most preferably 95% or higher within that region. Homology may be determined using an algorithm described herein. Probes and primers for detection or amplification of the polynucleotides of the present invention are included in these polynucleotides. Typical polynucleotides used as primers are 15 to 100 nucleotides long, and preferably 15 to 35 nucleotides long. Alternatively, polynucleotides used as probes are nucleotides at least 15 nucleotides in length, and preferably at least 30 nucleotides. They include at least a portion or an entire sequence of a DNA of the present invention. When using the nucleotides of the present invention as primers, the nucleic acid amplification reaction is not particularly limited, so long as a desired amplification product can be obtained. For example, the reaction may be selected from DNA amplification reactions such as polymerase chain reaction (PCR), ICAN, LAMP, SDA, and LCR, and RNA amplification reactions such as NASBA. A preferred method is PCR.

In one embodiment, such nucleotides are those specific to a DNA encoding a polypeptide of the present invention. The term "specific" refers to hybridizing under normal hybridization conditions, preferably stringent conditions, with DNA encoding a certain polypeptide, but not with DNAs encoding other polypeptides. Preferred embodiments are polynucleotides that hybridize to the genomic DNA encoding the cytolethal distending toxin of *Campylobacter coli* (SEQ ID NO: 1) but not to genomic DNAs encoding the cytolethal distending toxins of *Campylobacter jejuni* and *Campylobacter fetus*. Such polynucleotides include, for example, primer pairs selected from SEQ ID NOs: 13, 14, 28 to 36, 70, 71, 76, and 77. Alternatively, preferred embodiments are polynucleotides that hybridize to the genomic DNA encoding the cytolethal distending toxin of *Campylobacter fetus* (SEQ ID NO: 51) but not to genomic DNAs encoding the cytolethal distending toxins of *Campylobacter jejuni* and *Campylobacter coli*. Such polynucleotides include, for example, primer pairs selected from SEQ ID NOs: 15, 16, 37 to 46, 72, 73, 78, and 79.

In addition, with the identification of the genomic DNA encoding the cytolethal distending toxin of *Campylobacter coli* (SEQ ID NO: 1) in the Examples, the present inventors found nucleotide sequences specific to genomic DNAs encoding the cytolethal distending toxins of *Campylobacter jejuni* and *Campylobacter fetus*. Thus, the present invention also provides primer pairs specific to the genomic DNA encoding the cytolethal distending toxin of *Campylobacter jejuni* and those specific to the genomic DNA encoding the cytolethal distending toxin of *Campylobacter fetus*. The primers specific to the genomic DNA encoding the cytolethal distending toxin of *Campylobacter jejuni* include, but not limited to, for example, the primers of SEQ ID NOs: 11, 12, and 17 to 27. The primers specific to the genomic DNA encoding the cytolethal distending toxin of *Campylobacter fetus* include, but not limited to, for example, the primers of SEQ ID NOs: 15, 16, and 37 to 46.

In addition, with the identification of the genomic DNAs encoding the cytolethal distending toxins of *Campylobacter coli* (SEQ ID NO: 1) and *Campylobacter fetus* (SEQ ID NO: 51) in the Examples, the present inventors found common primers for the genomic DNAs encoding the cytolethal distending toxins of *Campylobacter coli*, *Campylobacter jejuni*, and *Campylobacter fetus* (primers that can amplify all genomic DNAs encoding the cytolethal distending toxins of these bacteria). The present invention also provides such common primers. Preferred common primers include, for example, primers of SEQ ID NOs: 64 and 65 (to amplify cdtA DNA), primers of SEQ ID NOs: 7 to 10 and 47 to 50 (to amplify cdtB DNA), and primers of SEQ ID NOs: 66 and 67 (to amplify cdtC DNA).

Those skilled in the art can appropriately prepare primers that include one or more nucleotides different from the above primers but can amplify the same genomic DNA regions as amplified with the above primers. Genomic DNA regions to which the above primers anneal are shown in FIGS. 17 to 19. The present invention also provides such mutant primers. As described above, nucleic acid amplification reactions to which the primers of the present invention are applicable are not particularly limited, so long as it yields desired amplification products. For example, the reaction can be selected from DNA amplification reactions such as PCR (polymerase chain reaction), ICAN, LAMP, SDA, and LCR, and RNA amplification reactions such as NASBA. A preferred method is PCR. Based on the above primers, those skilled in the art can design mutant primers adequate for nucleic acid amplification methods to be performed. Such mutant primers can be synthetically prepared. It can be readily assessed whether mutant primers can amplify the same genomic DNA region as amplified with the original primers, by conducting a nucleic acid amplification reaction using the mutant primers and analyzing the amplification products.

These primers can be preferably used to detect *Campylobacter* bacteria in test samples.

<Production of Vectors, Host Cells, and Polypeptides>

The present invention also provides methods for producing vectors carrying polynucleotides of the present invention, host cells retaining the polynucleotides or said vectors of the present invention, and polypeptides of the present invention utilizing said host cells.

The vectors of the present invention are not limited, so long as the DNAs inserted in the vectors are stably retained. For example, pBluescript vector (Stratagene) is a preferable cloning vector when using *E. coli* as a host. When using vectors to produce the polypeptides of the present invention, expression vectors are particularly useful. These expression vectors are not specifically limited, so long as they express polypeptides in vitro, in *E. coli*, in cultured cells, or in vivo. However, preferred examples include the pBEST vector (ProMega) for in vitro expression, the pET vector (Invitrogen) for expression in *E. coli*, the pME18S-FL3 vector (GenBank Accession No. AB009864) for expression in cultured cells, and the pME18S vector (Mol. Cell. Biol. 8:466-472 (1988)) for in vitro expression, and such. A DNA of the present invention can be inserted into a vector by conventional methods, for example, by a ligase reaction using restriction enzyme sites (Current Protocols in Molecular Biology, edit. Ausubel, et al., (1987) Publish. John Wiley & Sons, Section 11.4-11.11).

Host cells to which the vectors of the present invention are introduced are not specifically limited, and various host cells can be used according to the objectives of the present invention. For example, bacterial cells (e.g. *Streptococcus*, *Staphylococcus*, *E. coli*, *Streptomyces*, *Bacillus subtilis*), fungal cells (e.g. yeast, *Aspergillus*), insect cells (e.g. *Drosophila* S2, *Spodoptera* SF9), animal cells (e.g. CHO, COS, HeLa, C127, 3T3, BHK, HEK293, Bowes melanoma cell), and plant cells are examples of cells for expressing polypeptides. The transfection of a vector to a host cell can be carried out by conventional methods, such as calcium phosphate precipitation methods, electroporation methods (Current protocols in Molecular Biology, edit., Ausubel et al., (1987) Publish. John Wiley & Sons, Section 9.1-9.9), Lipofectamine methods (GIBCO-BRL), microinjection methods, and such.

In host cells, appropriate secretion signals can be incorporated into a polypeptide of interest in order to facilitate the secretion of an expressed polypeptide into the lumen of the endoplasmic reticulum, into the cavity around a cell, or into the extracellular environment. These signals may be endogenous signals or signals from a species different to the target polypeptide.

When a polypeptide of the present invention is secreted into culture media, this culture media is collected to collect the polypeptide of the present invention. When a polypeptide of the present invention is produced intracellularly, the cells are first lysed, and the polypeptide is then collected.

In order to collect and purify a polypeptide of the present invention from a recombinant cell culture, methods known in the art can be used, including ammonium sulfate or ethanol precipitation, acid extraction, anionic or cationic exchange chromatography, phosphocellulose chromatography, hydrophobic interaction chromatography, affinity chromatography, hydroxylapatite chromatography, and lectin chromatography.

<Antibodies>

The present invention provides antibodies that bind to a polypeptide of the present invention. Herein, the term "antibodies" refers to polyclonal antibodies, monoclonal antibodies, chimeric antibodies, single-stranded antibodies, humanized antibodies, and Fab fragments including Fab or other products of an immunoglobulin expression library.

A polypeptide of the present invention or its fragment, or analogs thereof, or a cell that expresses the same, can be used as an immunogen for producing antibodies that bind to a polypeptide of the present invention. The antibodies are preferably immunospecific to a polypeptide of the present invention. The term "immunospecific" means that an antibody has substantially higher affinity to polypeptides of the present invention compared to other polypeptides.

The antibodies binding to a polypeptide of the present invention can be prepared by methods known to those skilled in the art. For example, a polyclonal antibody can be obtained as follows: A polypeptide of the present invention, or a GST-fusion protein thereof, is administered to small animals, such as rabbits, to obtain serum. Polyclonal antibodies are prepared by purifying the serum by ammonium sulfate precipitation; a protein A or protein G column; DEAE ion exchange chromatography; an affinity column in which the polypeptide of the present invention is coupled; and such. On the other hand, monoclonal antibodies, for example, can be prepared as follows: A polypeptide of the present invention is administered to small animals such as mice, and their spleens are subsequently extirpated and ground down to separate the cells. The cells are then fused with mouse myeloma cells using reagents such as polyethylene glycol, and clones that produce antibodies binding to the polypeptide of the present invention are selected from these fused cells (hybridomas). The obtained hybridomas are then transplanted into mice peritoneal cavities, and ascites are collected from the mice. The monoclonal antibodies can be prepared by purifying the ascites using, for example, ammonium sulfate precipitation; a protein A or protein G column; DEAE ion exchange chromatography; an affinity column in which the polypeptides of the present invention are coupled; and such.

The antibodies of the present invention can also be used to detect and purify the polypeptides of the present invention in test samples.

<Detection of *Campylobacter* Bacteria in Test Samples>

The present invention provides methods for detecting *Campylobacter* bacteria in test samples. Detecting *Campylobacter* bacteria in test samples is useful for various purposes, for example, in the diagnosis for Campylobacteriosis, rapid examination of foods contaminated with *Campylobacter* bacteria, validation of food processing processes, and identification of causative bacteria at the time of food poisoning outbreak.

In one embodiment, the detection method of the present invention is a method for detecting the presence of *Campylobacter coli*, *Campylobacter jejuni*, and *Campylobacter fetus* in test samples, which includes the steps of:

(a) conducting a polymerase chain reaction on the test samples using a mixture of primer pairs specific to each of genomic DNAs encoding the cytolethal distending toxins of these bacteria; and (b) determining the presence of these bacteria based on the presence or molecular weight of amplified fragments from the genomic DNAs encoding the cytolethal distending toxins of the bacteria.

In an alternative embodiment, the detection method of the present invention is a method for detecting the presence of *Campylobacter coli*, *Campylobacter jejuni*, and *Campylobacter fetus* in test samples, which includes the steps of:

(a) conducting a nucleic acid amplification reaction on test samples using a common primer pair that can amplify genomic DNAs encoding the cytolethal distending toxins of these bacteria;

(b) conducting a polymerase chain reaction using the genomic DNAs amplified in step (a) as a template and a mixture of primer pairs specific to each of genomic DNAs encoding the cytolethal distending toxins of the bacteria; and (c) determining the presence of these bacteria based on the presence or molecular weight of amplified fragments from genomic DNAs encoding the cytolethal distending toxins of the bacteria.

PCR using multiple PCR primers in a single reaction system, as used in Examples, is called "multiplex PCR". Multiple bacterial species can be identified simultaneously by electrophoresing the PCR products and examining the sizes of their bands. The present invention provides methods for detecting *Campylobacter* bacteria by nucleic acid amplification methods, which include multiplex PCR as a typical example, using primers or combinations thereof that are suitably used to amplify multiple nucleic acid regions. There is no limitation on the type of nucleic acid amplification method in the present invention, as long as desired amplification products can be obtained. A preferred method is PCR.

Mixtures of specific primer pairs used in such methods include, for example, mixtures of the following primer pairs:

(a) a primer pair selected from SEQ ID NOs: 13, 14, and 28 to 36 to amplify genomic DNA encoding the cytolethal distending toxin of *Campylobacter coli*, or a primer pair that can amplify the same genomic DNA region as amplified with the primer pair;

(b) a primer pair selected from SEQ ID NOs: 11, 12, and 17 to 27 to amplify genomic DNA encoding the cytolethal distending toxin of *Campylobacter jejuni*, or a primer pair that can amplify the same genomic DNA region as amplified with the primer pair; and (c) a primer pair selected from SEQ ID NOs: 15, 16, and 37 to 46 to amplify genomic DNA encoding the cytolethal distending toxin of *Campylobacter fetus*, or a primer pair that can amplify the same genomic DNA region as amplified with the primer pair. In addition, a primer pair selected from, for example, SEQ ID NOs: 7 to 10 and 47 to 50, or a primer pair that can amplify the same genomic DNA region as amplified with the primer pair, can be used as a common primer pair.

In a further embodiment of the present invention, the detection method is a method for detecting the presence of *Campylobacter coli*, *Campylobacter jejuni*, and *Campylobacter fetus* in test samples, which includes the steps of:

(a) conducting a nucleic acid amplification reaction on test samples using a common primer pair that can amplify genomic DNAs encoding the cytolethal distending toxins of these bacteria;

(b) digesting the genomic DNAs amplified in step (a) with a restriction enzyme; and (c) determining the presence of these bacteria based on the molecular weight of DNA fragments resulting from the digestion. Restriction enzymes that can be used in this method are not particularly limited as long as it allows identification of genomic DNAs encoding the cytolethal distending toxins of *C. coli*, *C. jejuni*, and *C. fetus*, and include, for example, Sau3AI, DsaI, MboI, RsaI, EcoRI, HinfI, NdeI, PstI, XbaI, and XhoII. Meanwhile, examples of common primer pairs include primer pairs selected from SEQ ID NOs: 7 to 10 and 47 to 50, and primer pairs that can amplify the same genomic DNA region as amplified with the primer pairs.

A method for detecting polymorphisms based on lengths of fragments generated by digesting PCR-amplified DNA with various restriction enzymes, as described in the Example below, is called PCR-RFLP (PCR-Restriction Fragment Length Polymorphism). The present invention also provides primers that are suitably used in methods for detecting polymorphisms, which includes PCR-RFLP as a typical example, based on lengths of fragments generated by treating DNA amplified by nucleic acid amplification methods with various restriction enzymes.

In another embodiment of the present invention, the detection method is a method for detecting the presence of *Campylobacter* bacteria in test samples, which includes the steps of:

(a) conducting a nucleic acid amplification reaction on test samples using a common primer pair that can amplify genomic DNA encoding the cytolethal distending toxin of *Campylobacter* bacteria; and (b) determining the presence of *Campylobacter* based on the presence or molecular weight of amplified fragments from genomic DNA encoding the cytolethal distending toxin of *Campylobacter* bacteria. Primer pairs used in this method are those that can amplify genomic DNAs encoding the cytolethal distending toxins of *Campylobacter* bacteria regardless of *Campylobacter* species. Such common primer pairs include, for example, primer pairs selected from SEQ ID NOs: 7 to 10, 47 to 50, and 64 to 67. As described above, the above primer pairs are common primer pairs that amplify all of genomic DNAs encoding the cytolethal distending toxins of the three species, *Campylobacter coli, Campylobacter jejuni,* and *Campylobacter fetus*. The primer pairs described above are expected to amplify genomic DNAs encoding the cytolethal distending toxins of not only the above-described three species but also other *Campylobacter* bacteria. Likewise, primer pairs that can amplify the same genomic DNA region as amplified with the primer pairs described above may be amplify genomic regions of all the three bacterial species described above and other *Campylobacter* bacteria.

The present invention also provides kits used in the above detection methods of the present invention. These kits include an instruction manual in addition to the primer pairs described above. The kits may also include other components.

The detection of *Campylobacter* bacteria can be achieved at the protein level as well as at the DNA level as described above. The presence of these bacteria can be assessed in test samples by, for example, detecting the cytolethal distending toxins of the bacteria by Western blotting, dot blotting, immunoprecipitation, enzyme-linked immunosorbent assay (ELISA), immunofluorescence, or such using antibodies specific to the cytolethal distending toxins of the bacteria.

All prior art documents cited herein are incorporated herein by reference.

EXAMPLES

Example 1

*Campylobacter* Strains

*C. jejuni, C. coli,* and *C. fetus* collected from various clinical materials during 2001 to 2003 were used. Each strain was cultured in blood agar plates (Blood Agar Base No. 2: OXOID) containing 5% defibrinated horse blood (Japan Biological Material Center) and *Campylobacter* Selective Supplement SR69 (OXOID). *C. jejuni* and *C. coli* were cultured under 5% $O_2$, 10% $CO_2$, and 85% $N_2$ gases at 42° C., while *C. fetus* was cultured at 25° C. in a low-temperature $O_2/CO_2$ gas incubator (MODEL9200: Wakenyaku Co., Ltd).

Example 2

Preparation of PCR Template

Five clones of each bacterial species were scraped off and suspended in 500 µl of sterile PBS. The harvested bacteria were washed by centrifugation at 10,000 rpm for 5 min (MRX-150: TOMY SEIKO Co., Ltd.), and then resuspended in 300 µl of sterile PBS. Then, the suspensions were boiled in boiling water bath for 10 minutes, and cooled on ice. The suspensions were centrifuged at 15,000 rpm for 10 min and the resulting supernatants were collected. The amount of DNA in the collected supernatants were quantified using a spectrophotometer (Ultrospec 3100pro: Amersham Biosciences). Each quantified cell extract was diluted to 20 ng/µl and subjected to PCR.

Example 3

Preparation of *C. coli* cdtB Probe and Southern Hybridization

A *C. coli* cdtB probe was prepared by PCR labeling using the primers GNW and LPF-D, DIG Labeling Mix (Roche), and cell extract of *C. coli* Co1-192 as a template.

Figure 1:
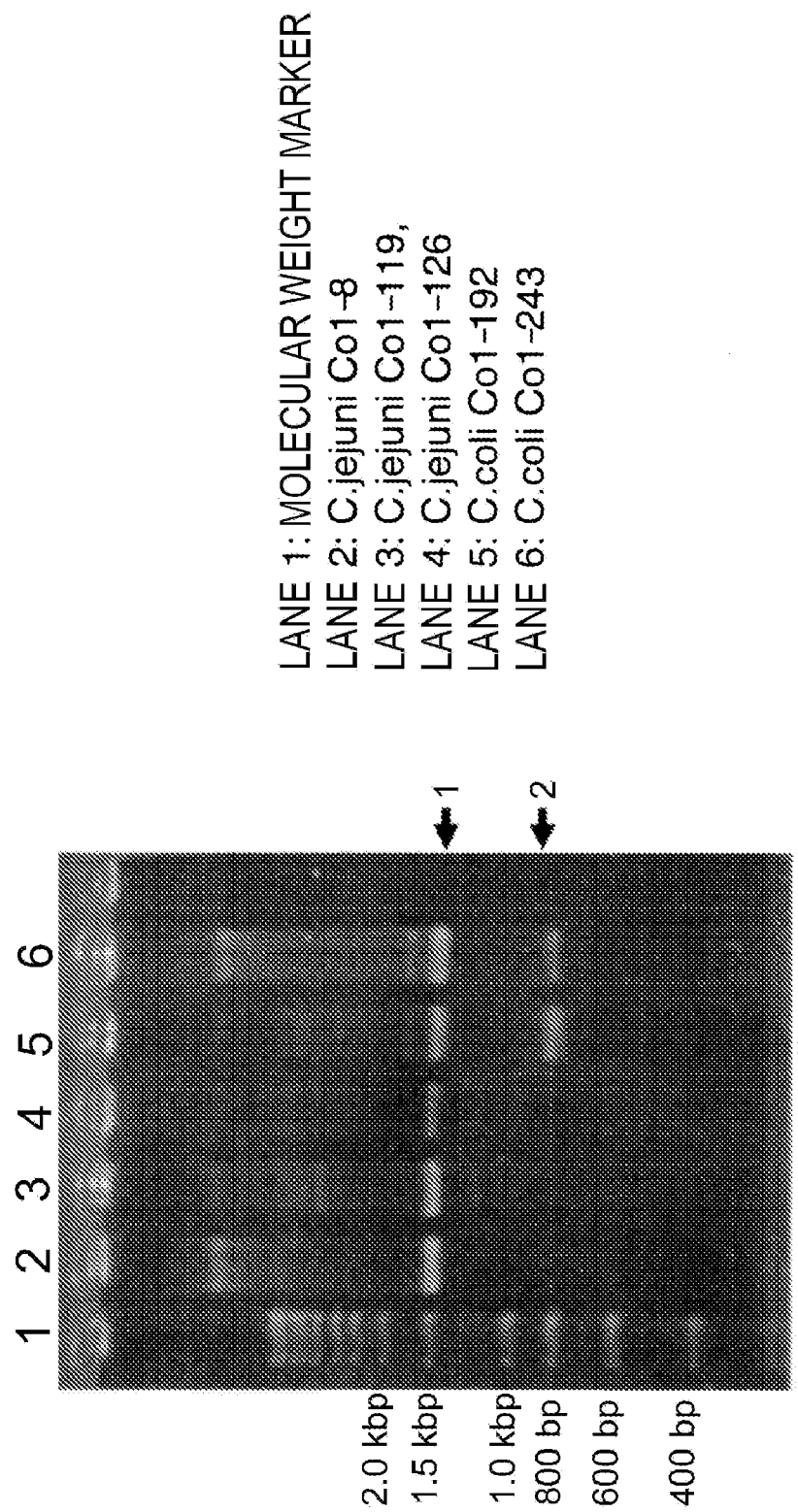

Specifically, to test the existence of the *C. coli* CDT gene, three *C. jejuni* strains and two *C. coli* strains were analyzed by PCR using the degenerate primers GNW [SEQ ID NO: 5: 5'-GG(ACGT)AA(CT)TGGAT(ACT)TGGGG(ACGT)TA-3'] and LPF-D [SEQ ID NO: 6: 5'-(AGT)AA(CT)TG(ACGT)AC(AGT)TA(ACGT)CC(AGT)AA (ACGT)GG-3'] described in a reference (Pickett, C. et al. Infect. Immun., 64: 2070 (1996)) under the condition of: 94° C. for 3 minutes, 30 cycles of [94° C. for 30 seconds, 42° C. for 30 seconds, and 72° C. for 2 minutes], and 72° C. for 5 minutes. All three *C. jejuni* strains and two *C. coli* strains gave bands of the amplified cdt region at about 1.5 Kb (arrow 1 in FIG. 1).

The amplified bands were ligated into pT7 vector (Novagen), and *E. coli* (*E. coli* JM109) cells were transformed with the ligates. Sequencing of the resulting clones using a sequencer (ABI PRISM 377 DNA sequencer; Applied Biosystems) showed similar sequences to cdtB. BigDye terminator Cycle Sequencing Kits (Applied Biosystems) were used in the sequence reaction. In addition, 800 bp bands (arrow 2 in FIG. 1) were found to be cdtB-derived secondary bands, which were amplified because GNW primer was a mixed primer.

20 µg of *C. coli* Co1-192 genomic DNA was digested with 60 U of restriction enzyme HindIII at 37° C. for 12 hours. Then, Southern blotting and DNA-DNA hybridization were performed using the prepared probe according to a conventional method (Molecular cloning: a laboratory manual, Cold Spring Harbor Laboratory, Cold Spring Harbor, (2001)).

The hybridization was carried out under a stringent condition at 42° C. After blotting, the blot was washed twice with a 2×SSC/0.1% SDS solution at room temperature for five minutes, and then twice with a 0.2×SSC/0.1% SDS solution at 60° C. for 15 minutes.

Figure 2:
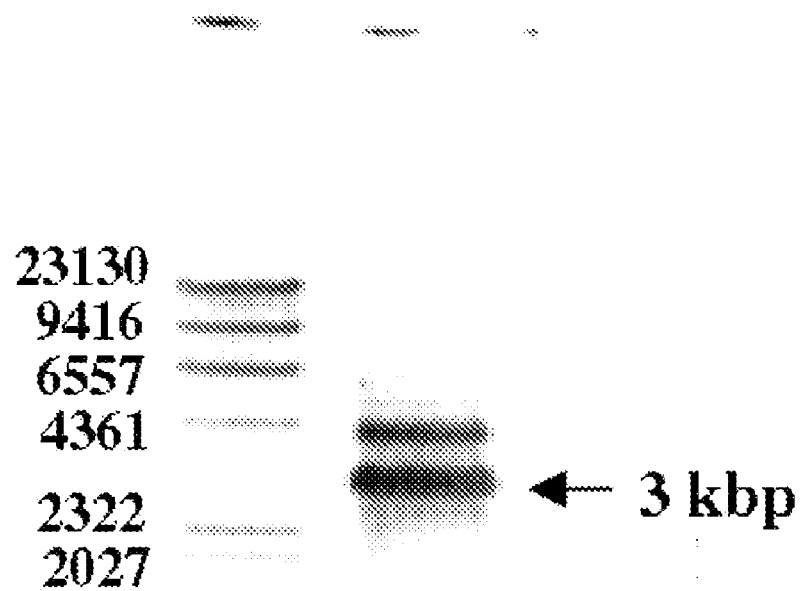

As a result, probe-positive bands were found at about 3 and 4 kbp (FIG. 2). The 3-kbp band was ligated into pUC18 vector. *E. coli* JM109 was transformed with the ligate, yielding a clone containing the cdtB region (3k44).

Example 4

Sequencing of *C. coli* cdtB Gene

The clone 3k44 containing the cdtB region of *C. coli* obtained in Example 3 was sequenced by a conventional method. The sequence of entire *C. coli* CDT region was determined as shown in SEQ ID NO: 1.

Example 5

Design of Common Primer Pair 1 and PCR

Figure 3:
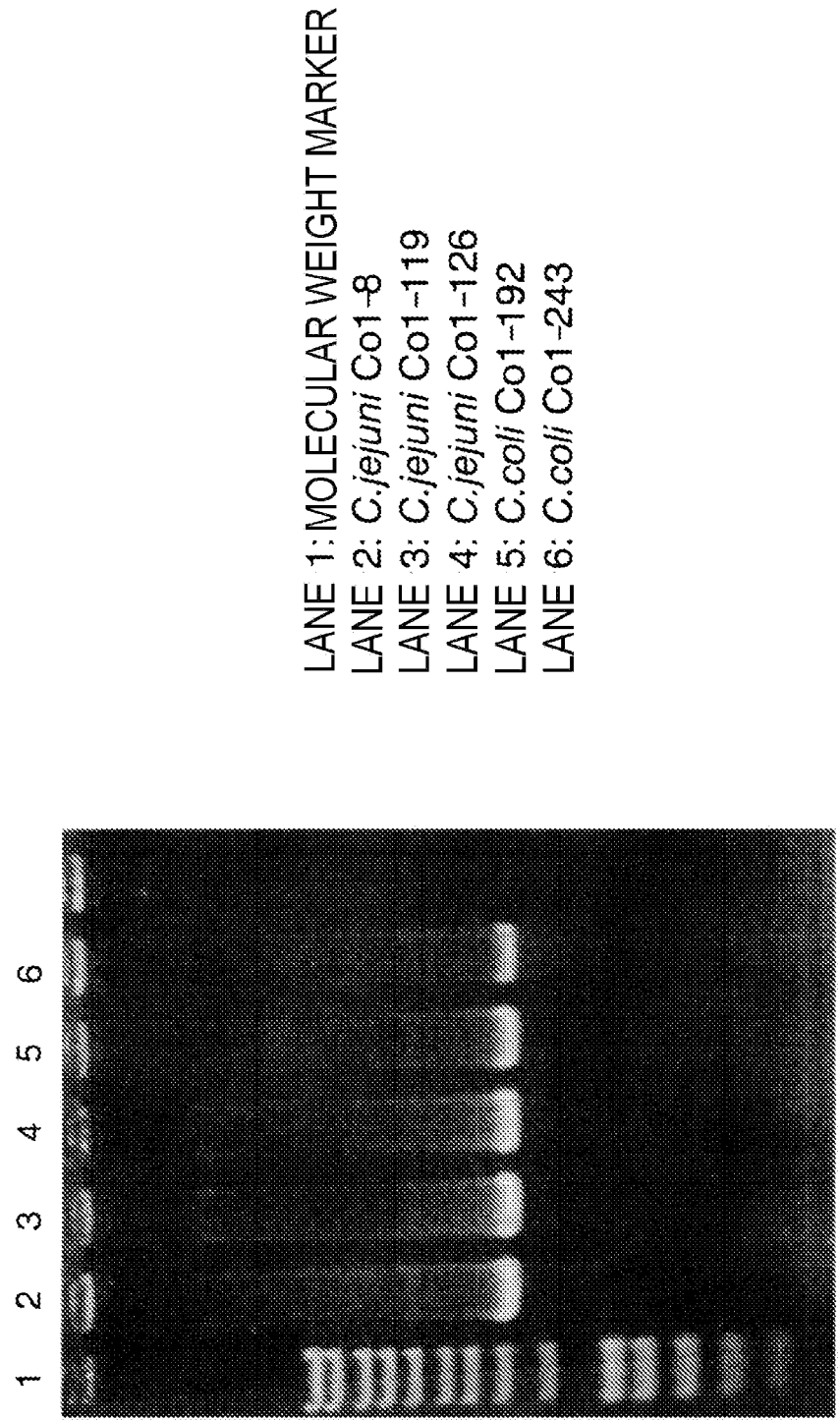

The *C. coli* CDT sequence of the present invention was compared with the CDT gene of *C. jejuni* from known databases to design common primers U and R described below. The primers were mixed and added to 1 µl of 20 ng/µl cell extract to give each primer concentration of 0.5 mM. The final volume was adjusted to 20 µl with PCR buffer (TaKaRa Ex Taq kit: Takara Bio). The reaction mixture was subjected to PCR under the condition of: 94° C. for 3 minutes, 30 cycles of [94° C. for 30 seconds, 55° C. for 30 seconds, 72° C. for 1 minute], and 72° C. for 3 minutes. The result is shown in FIG. 3. Amplified fragments of about 1900 bp were found, and thus CDT-derived bands were detected from both *C. jejuni* (lanes 2 to 4) and *C. coli* (lanes 5 and 6).

```
Common primer U
[SEQ ID NO: 7: GATAA(CT)GATCCTTTAAAACT]

Common primer R
[SEQ ID NO: 8: (AT)(AT)CCAAAGCG(AT)TTTT(CG)TATGG]
```

Example 6

Design of Common Primer Pair 2 and PCR

Figure 4:
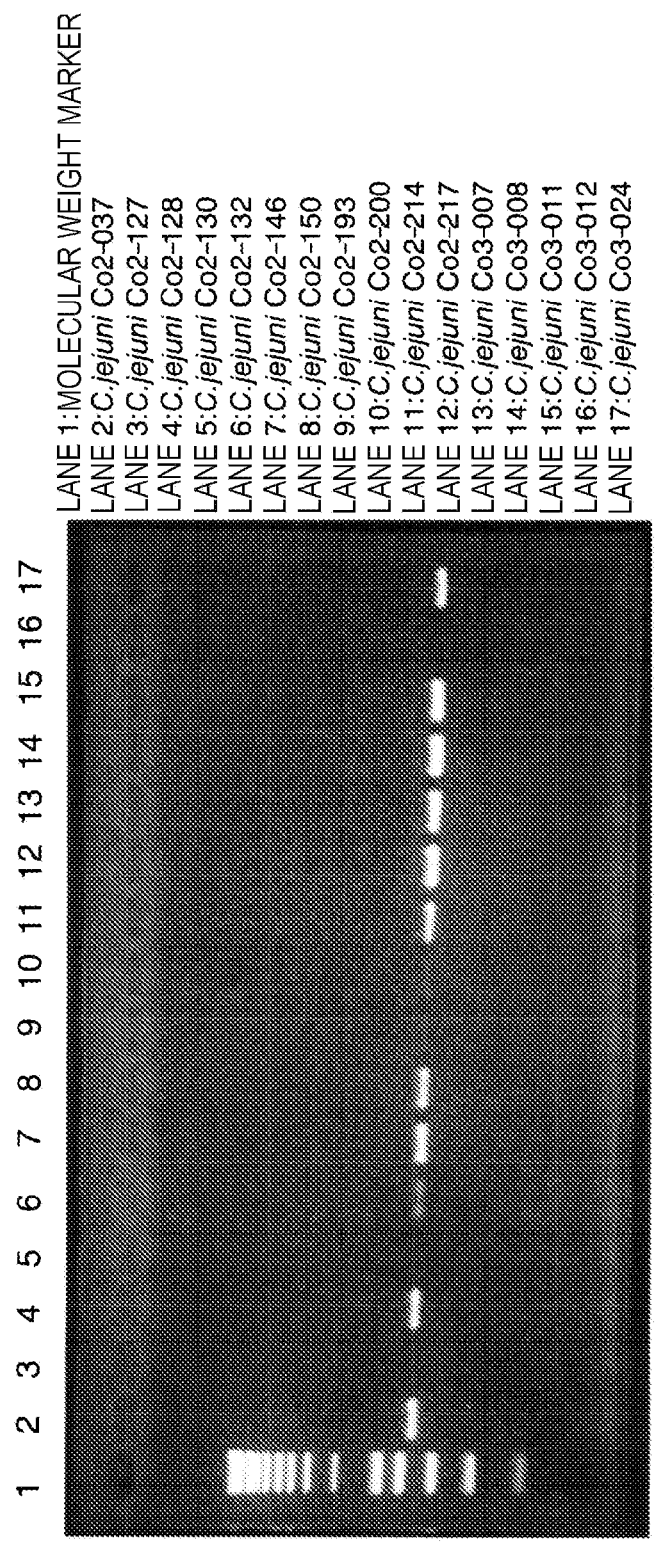
Figure 5:
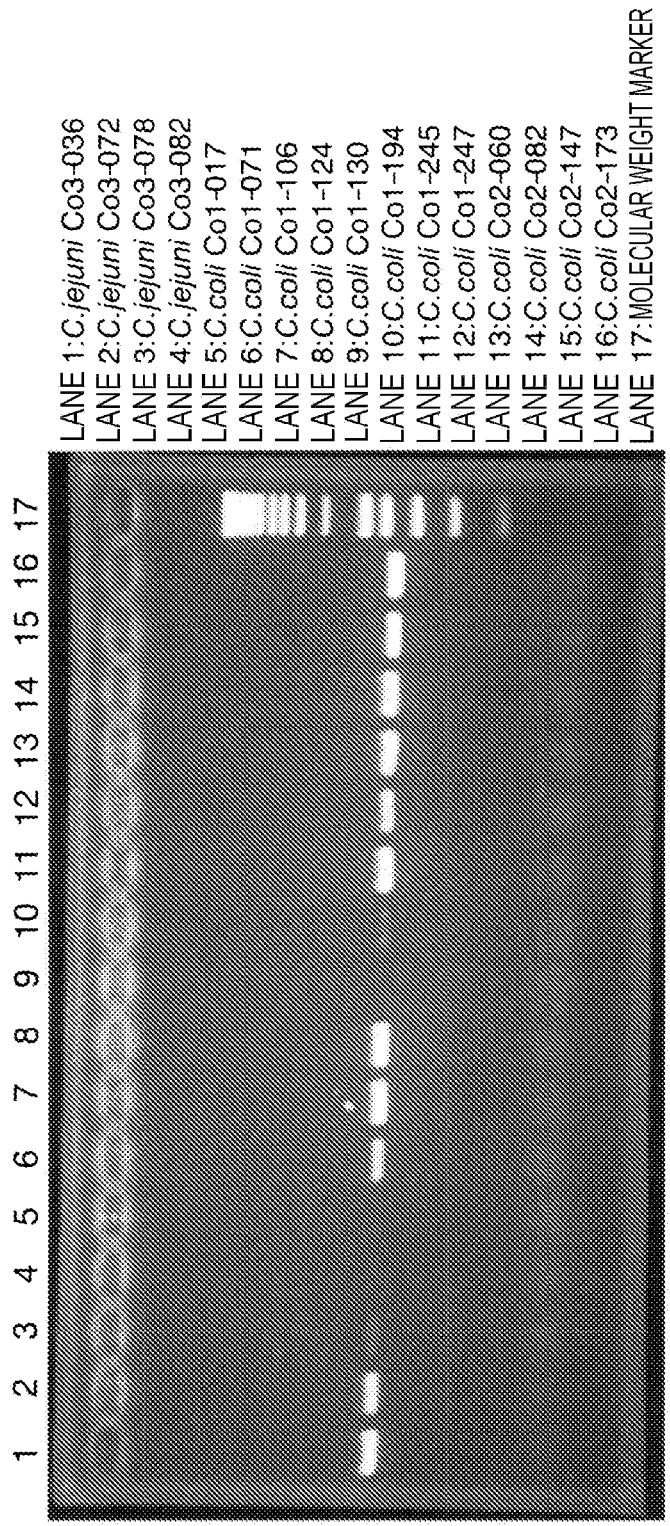
Figure 6:
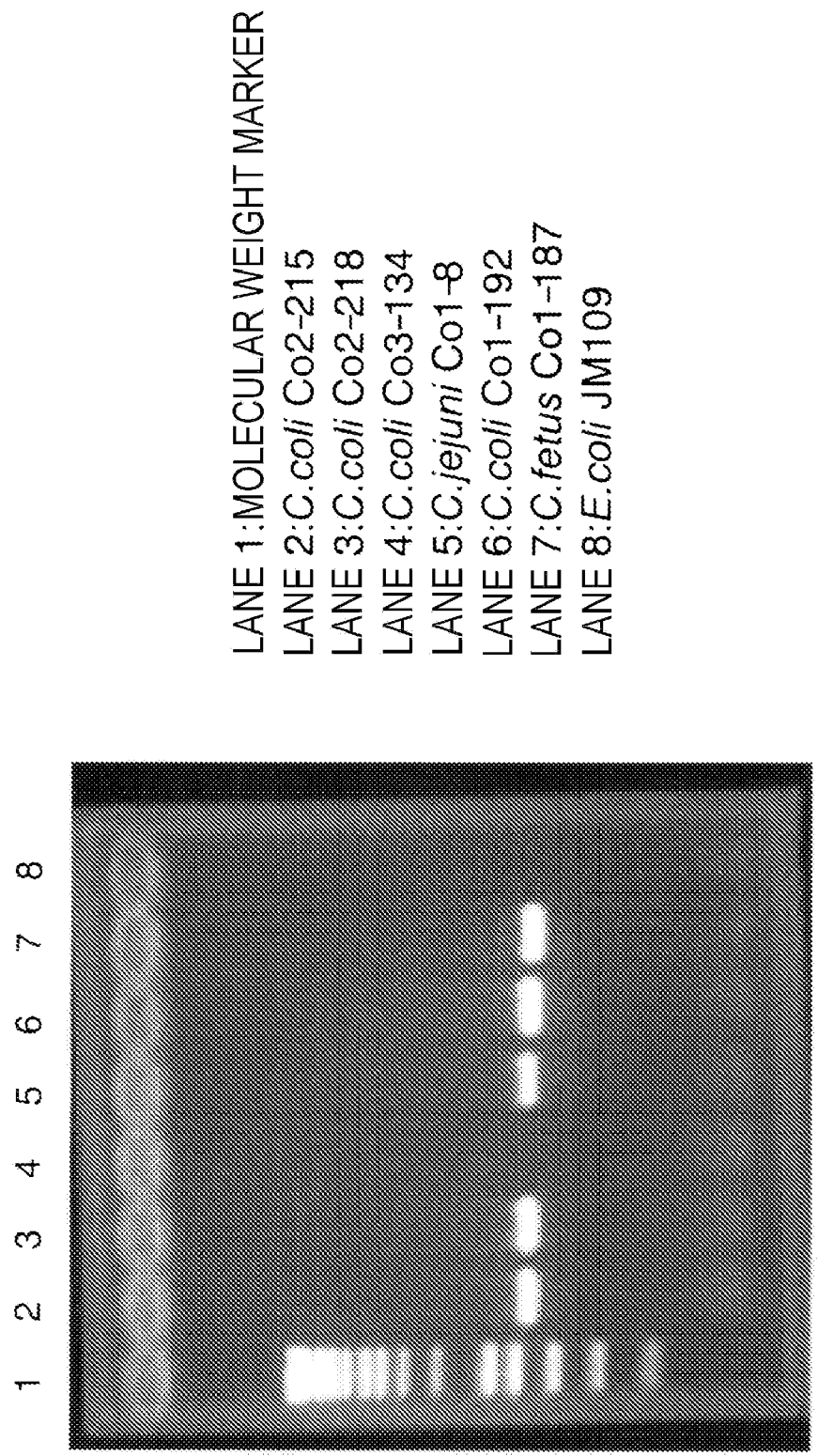

Likewise, common primers Up and Do indicated below were designed, and PCR was carried out under the condition of: 94° C. for 3 minutes, 30 cycles of [94° C. for 30 seconds, 50° C. for 30 seconds, and 72° C. for 45 seconds], and 72° C. for 3 minutes. The results are shown in FIGS. 4 to 6. Amplified fragments of about 720 bp were found.

```
Common primer Up
[SEQ ID NO: 9: ACTTGGAATTTGCAAGGC]

Common primer Do
[SEQ ID NO: 10: TCTAAAATTTAC(ACT)GGAAAATG]
```

Example 7

Design of Specific Primers and Detection of cdtB Gene by Multiplex PCR

The *C. coli* CDT sequence of the present invention was compared with the CDT gene of *C. jejuni* from known databases to design *C. jejuni*-specific primers CjSPBU3 and CjSPBR3 described below. Likewise, *C. coli*-specific primers CcSPBU5 and CcSPBR5, and *C. fetus*-specific primers CfSPBU1 and CfSPBR1 were designed.

Figure 7:
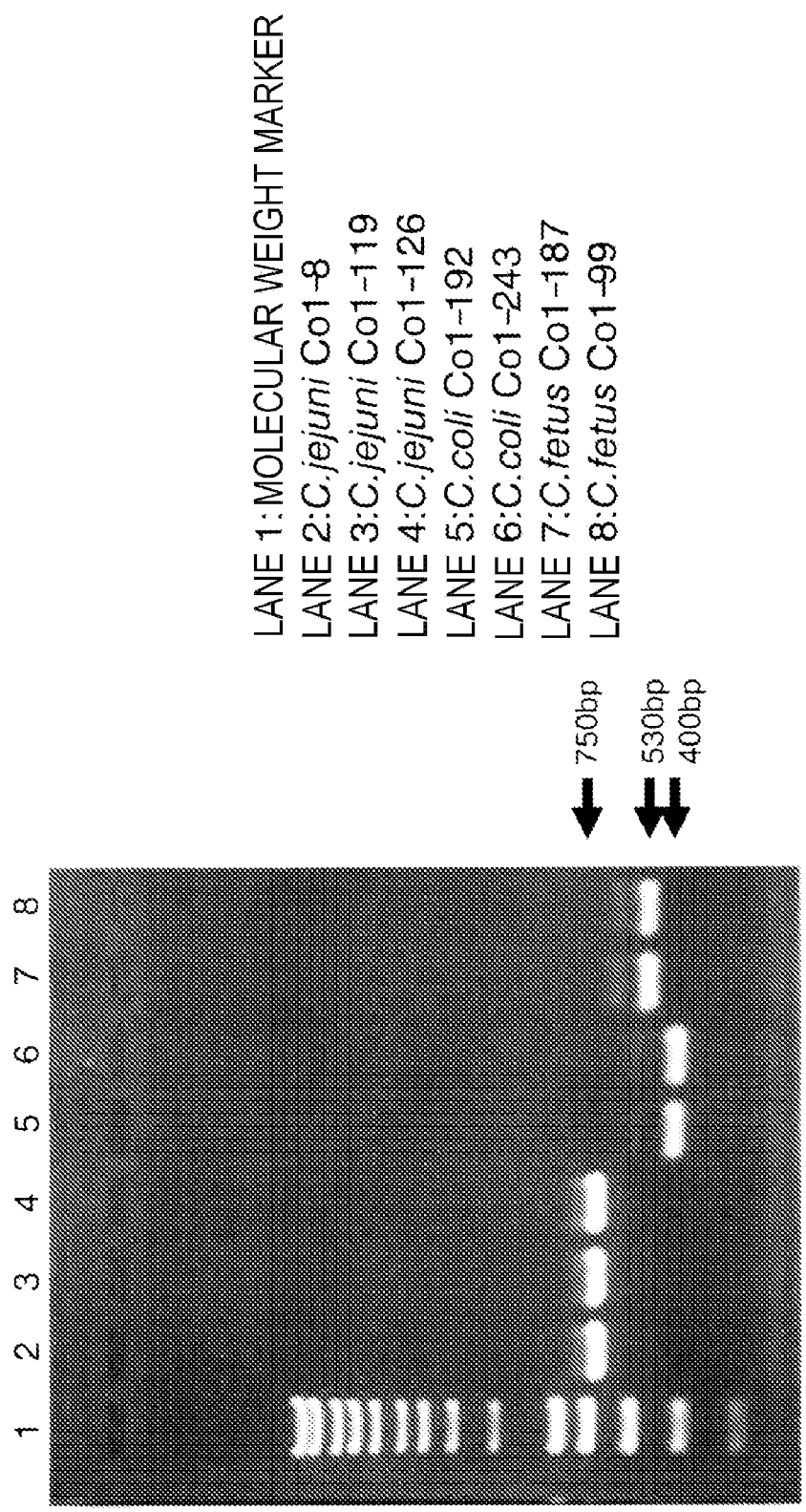

The primers were combined and added to 1 µl of 20 ng/µl cell extract to give each primer concentration of 0.5 mM. The final volume was adjusted to 20 µl with PCR buffer (TaKaRa Ex Taq kit: Takara Bio). The reaction mixture was subjected to multiplex PCR under the condition of: 94° C. for 3 minutes, 30 cycles of [94° C. for 56 seconds, 55° C. for 30 seconds, and 72° C. for 45 seconds], and 72° C. for 3 minutes (GeneAmp PCR system 9700; Applied Biosystems). The result is shown in FIG. 7. Amplified CDT fragments specific to *C. jejuni* (about 750 bp), *C. coli* (about 400 bp), and *C. fetus* (about 530 bp) were found, allowing the discrimination of *C. jejuni* (lanes 2 to 4), *C. coli* (lanes 5 and 6), and *C. fetus* (lanes 7 and 8).

```
Specific primer CjSPBU3
[SEQ ID NO: 11: TACTCCGCCTTTTACCGCA]

Specific primer CjSPBR3
[SEQ ID NO: 12: GAGTATAGGTTTGTTGTC]

Specific primer CcSPBU5
[SEQ ID NO: 13: TTTAATGTATTATTTGCCGC]

Specific primer CcSPBR5
[SEQ ID NO: 14: TCATTGCCTATGCGTATG]

Specific primer CfSPBU1
[SEQ ID NO: 15: CGCAAGTTGGAAGACTAT]

Specific primer CfSPBR1
[SEQ ID NO: 16: TTTATTATCGCCGGAGCA]
```

Example 8

Identification of Bacterial Species by PCR-RFLP Using Common Primer Pair 1

Figure 8:
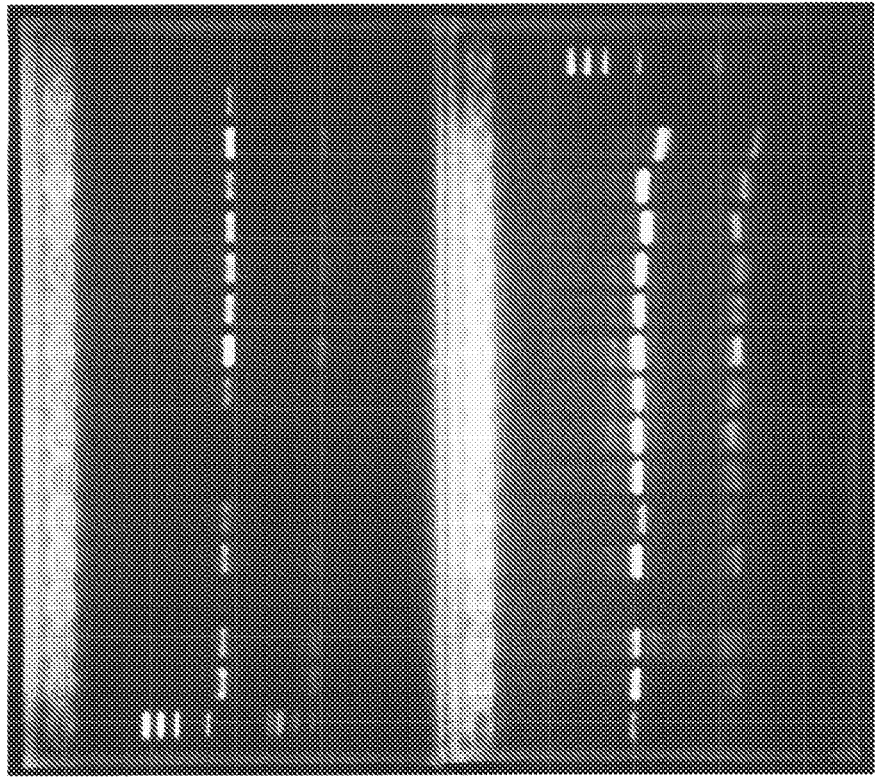
FIG. 8 is a photograph showing a result of PCR-RFLP for *C. jejuni*, *C. coli*, and *C. fetus* strains using common primer pair 1.

After PCR using common primer pair 1 obtained in Example 6, 5 U of the restriction enzyme Sau3AI (NEB) was added to 8.5 µl of the reaction solution. The resulting mixture was reacted at 37° C. for 3 hours and then electrophoresed. The result is shown in FIG. 8.

Example 9

Detection of cdtB Gene by Multiplex PCR Using Specific Primers

Figure 9:
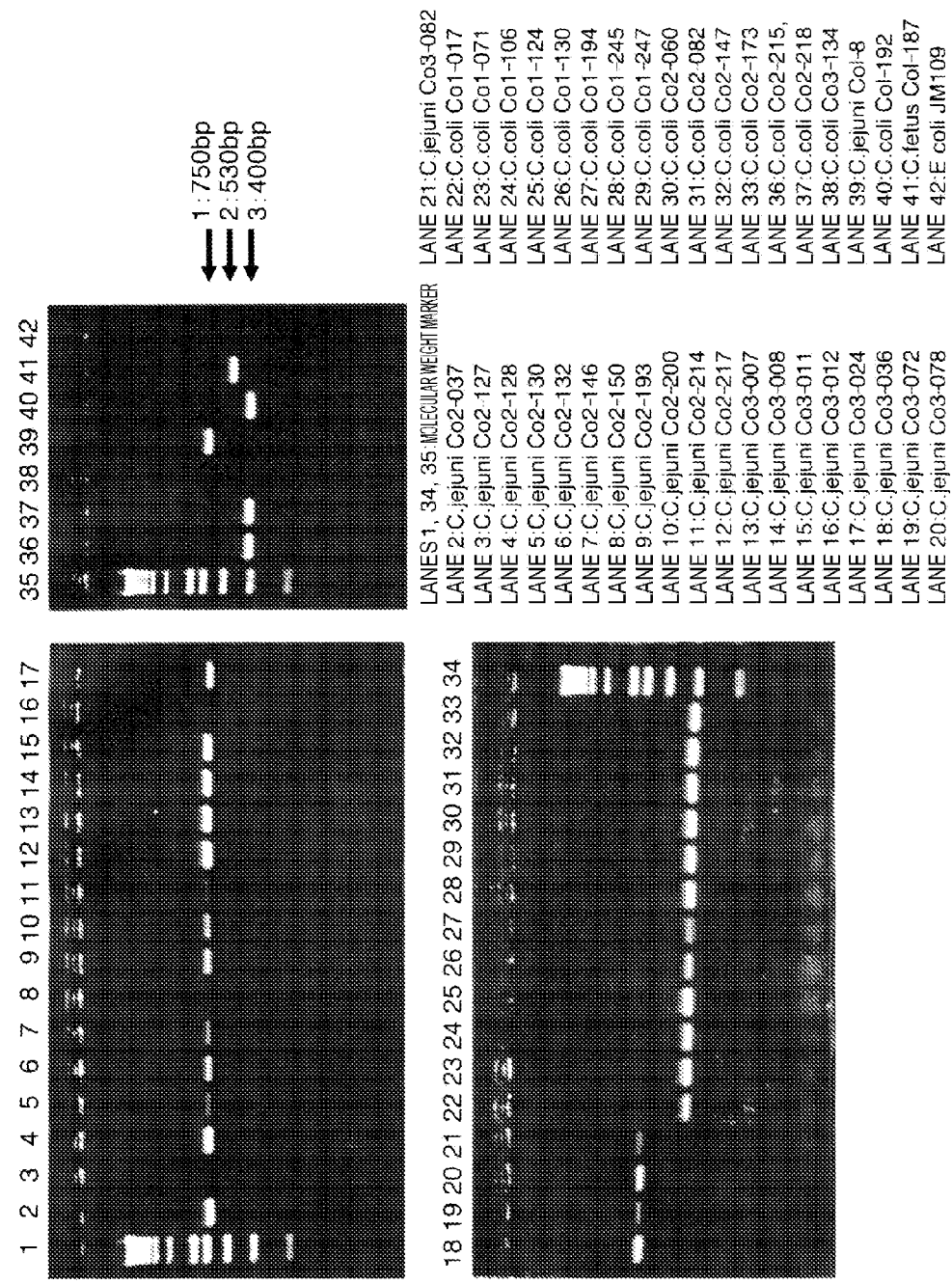
FIG. 9 is a set of photographs showing a result of multiplex PCR for various strains of *C. jejuni*, *C. coli*, and *C. fetus* using specific primers. CDT-specific amplified fragments unique to each species were detected (*C. jejuni*, 750 bp; *C. coli*, 400 bp; *C. fetus*, 530 bp).

Multiplex PCR was performed on other various clinical strains of *Campylobacter* bacteria by using specific primers obtained in Example 7 and the experimental condition in Example 7. The result is shown in FIG. 9. As in the case of Example 7, amplified CDT fragments specific to *C. jejuni* (about 750 bp), *C. coli* (about 400 bp), and *C. fetus* (about 530 bp) were found, allowing the discrimination of each species.

Example 10

Preparation of *C. fetus* cdtB Probe and Southern Hybridization

A *C. fetus* cdtB probe was prepared by PCR labelling using common primer pair 2 (common primers Up and Do), DIG Labeling Mix (Roche), and cell extract of *C. fetus* Co1-187 as a template.

20 µg of genomic DNA of *C. fetus* Co1-187 was digested with 60 U of the restriction enzyme HindIII at 37° C. for 12 hours. Then, Southern blotting and DNA-DNA hybridization were carried out according to a conventional method (Molecular cloning: a laboratory manual, Cold Spring Harbor Laboratory, Cold Spring Harbor, (2001)) using the obtained probe. The hybridization was carried out under a stringent condition at 42° C. After blotting, the blot was washed twice with a 2×SSC/0.1% SDS solution at room temperature for five minutes, and then twice with a 0.2×SSC/0.1% SDS solution at 60° C. for 15 minutes.

Figure 10:
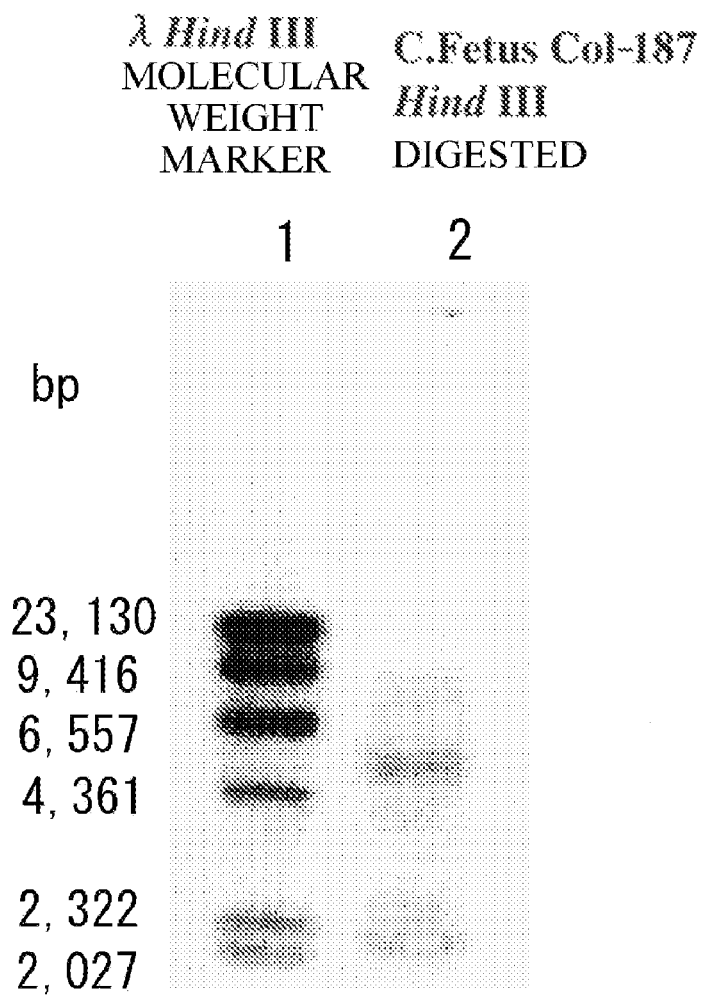
FIG. 10 is a photograph showing a result of hybridization after digestion of genomes from *C. fetus* Col-187 cells with the restriction enzyme HindIII.

As a result, probe-positive bands were found at about 2 and 5 kbp (FIG. 10). The 2-kbp bands was ligated into pUC18 vector. *E. coli* JM109 was transformed with the ligate, yielding a clone containing the cdtB region (Cf78).

Example 11

Sequencing of *C. fetus* CDT Gene

The clone Cf78 containing the cdtB region of *C. fetus* obtained in Example 10 was sequenced by a conventional method to determine the sequences of the cdtA and cdtB regions of *C. fetus*. Since the clone Cf78 did not contain cdtC region, the sequence of cdtC region was determined by performing gene walking under the condition described below using random primers designed based on the determined cdtB gene sequence. Thus, the sequence of the entire *C. fetus* CDT region was determined as shown in SEQ ID NO: 51.

[Gene Walking Using Random Primer]

The primer sets consisting of a random primer, target amplification primer, and sequencing primer described below were designed based on the gene sequence determined in Example 11. The targets were amplified using the *C. fetus* Co1-187 gene as a template. For the target amplification, 10 pmol of the random primer was added to 20 ng of the template gene, and the final volume was adjusted to 100 μl using KOD Dash PCR Kit (TOYOBO). The reaction mixture was subjected to PCR under the condition of: 94° C. for 2 minutes and 35 cycles of [94° C. for 20 seconds, 65° C. for 5 seconds, and 74° C. for 30 seconds].

The resulting PCR products were sequenced according to a conventional method using the sequencing primers.

```
Primer set 1
Random primer
[SEQ ID NO: 55: GCTTGTAGCAGTATTGATGCNNNNNNNNNN]
Target amplification primer
[SEQ ID NO: 56: GCTTGTAGCAGTATTGATGC]
Sequencing primer
[SEQ ID NO: 57: CTAGTTTCGGACCATTTTCC]

Primer set 2
Random primer
[SEQ ID NO: 58: ATACGCAATGCAAACACCGGNNNNNNNNNN]
Target amplification primer
[SEQ ID NO: 59: ATACGCAATGAAACACCGG]
Sequencing primer
[SEQ ID NO: 60: TAAAAGCGATTTTCAGGGCAG]

Primer set 3
Random primer
[SEQ ID NO: 61: TGTCGACATAGAGCCTAAACNNNNNNNNNN]
Target amplification primer
[SEQ ID NO: 62: TGTCGACATAGAGCCTAAAC]
Sequencing primer
[SEQ ID NO: 63: ATTTTCACCGCCGCTTAGTG]
```

Example 12

Design of cdtA Common Primers and PCR

The cdtA sequences of *C. coli* and *C. fetus* of the present invention were compared with the cdtA gene of *C. jejuni* from known databases to design cdtA common primers U and R described below. The primers were combined and added to 1 μl of 20 ng/μl cell extract to give each primer concentration of 0.25 mM. The final volume was adjusted to 20 μl with PCR buffer (TaKaRa Ex Taq kit: Takara Bio). The reaction mixture was subjected to PCR under the condition of: 94° C. for 3 minutes, 30 cycles of [94° C. for 30 seconds, 55° C. for 30 seconds, and 72° C. for 30 seconds], and 72° C. for 3 minutes. The result is shown in FIG. 11 (left). Amplified fragments of about 550 bp were found. Thus, cdtA-derived bands were detected for all of *C. jejuni* (lanes 2 to 4), *C. coli* (lanes 5 and 6), and *C. fetus* (lanes 7 and 8).

```
CdtA common primer U
[SEQ ID NO: 64: (GA)A(ACT)GAT(AC)(AC)(TAG)GAT(AC)G
ATCC(AT)(TC)CAAA]

CdtA common primer R
[SEQ ID NO: 65: (GA)(AT)AA(TC)AGG(TC)G(CT)TTG(CT)A
(AT)(GA)CA]
```

Example 13

Detection of cdtA Gene by PCR Using cdtA Common Primers

PCR was performed on other various clinical strains of *Campylobacter* bacteria using the common primers obtained in Example 12 and the experimental condition in Example 12. The result is shown in FIG. 12. As in the case of Example 12, amplified fragments specific to cdtA (about 550 bp) were found.

Example 14

Design of cdtC Common Primers and PCR

The cdtC sequences of *C. coli* and *C. fetus* of the present invention were compared with the cdtC gene of *C. jejuni* from the known database (BLAST) to design cdtC common primers U and R described below.

1 μl of 20 ng/μl cell extract and the primers were combined to give each primer concentration of 0.25 mM. The final volume was adjusted to 20 μl with PCR buffer (TaKaRa Ex Taq kit: Takara Bio). The reaction mixture was subjected to PCR under the condition of: 94° C. for 3 minutes, 30 cycles of [94° C. for 30 seconds, 55° C. for 30 seconds, and 72° C. for 30 minutes], and 72° C. for 3 minutes. The result is shown in FIG. 3. Amplified fragments of about 320 bp were found. Thus, cdtC-derived bands were detected for all of *C. jejuni* (lanes 10-12), *C. coli* (lanes 13 and 14), and *C. fetus* (lanes 15 and 16) (FIG. 11; right).

```
CdtC common primer U
[SEQ ID NO: 66:(AGC)A(TG)(TC)(TC)(AT)(AG)(AT)(AT)
(GT)A(CT)CAAAA(CT)TGG]

CdtC common primer R
[SEQ ID NO: 67:(AGC)CTA(AGT)(AT)CC(AT)A(AC)(GT)C
(GT)
(AT)T(CT)TT(GC)]
```

Example 15

Detection of cdtC Gene by PCR Using cdtC Common Primers

PCR was performed on other various clinical strains of *Campylobacter* bacteria using the common primers obtained in the Examples and the experimental condition in Example 14. The result is shown in FIG. 13. As in the case of Example 14, amplified fragments specific to cdtC (about 320 bp) were found.

Example 16

Design of cdtA Specific Primers and Detection of cdtA Gene by Multiplex PCR

The CDT sequence of C. fetus of the present invention was compared with the CDT genes of C. jejuni and C. coli from the known database (BLAST) to design C. jejuni-specific primers CjASPU2 and CjASPR2 described below. Likewise, the C. coli-specific primers CcASPUl and CcASPR1 and C. fetus-specific primers CfASPU1 and CfASPR1 were designed.

The primers were combined and added to 1 µl of 20 ng/µl cell extract to give each primer concentration of 0.125 mM. The final volume was adjusted to 20 p with PCR buffer (TaKaRa Ex Taq kit: Takara Bio). The reaction mixture was subjected to multiplex PCR under the condition of: 94° C. for 3 minutes, 30 cycles of [94° C. for 30 seconds, 55° C. for 30 seconds, and 72° C. for 30 seconds], and 72° C. for 3 minutes (GeneAmp PCR System 9700; Applied Biosystems). The result is shown in FIG. 14 (left). Amplified CDT fragments specific to C. jejuni (about 630 bp), C. coli (about 330 bp), and C. fetus (about 490 bp) were found, allowing the discrimination of C. jejuni (lanes 2 to 4), C. coli (lanes 5 and 6), and C. fetus (lanes 7 and 8).

```
Specific primer CjASPU2
[SEQ ID NO: 68: AGGACTTGAACCTACTTTTC]

Specific primer CjASPR2
[SEQ ID NO: 69: AGGTGGAGTAGTTAAAAACC]

Specific primer CcASPU1
[SEQ ID NO: 70: ATTGCCAAGGCTAAAATCTC]

Specific primer CcASPR1
[SEQ ID NO: 71: GATAAAGTCTAAAACTGC]

Specific primer CfASPU1
[SEQ ID NO: 72: AACGACAAATGTAAGCACTC]

Specific primer CfASPR1
[SEQ ID NO: 73: TATTTATGCAAGTCGTGCGA]
```

Example 17

Detection of cdtA Gene by Multiplex PCR Using cdtA-Specific Primers

Multiplex PCR was performed on other various clinical strains of Campylobacter bacteria using the specific primers obtained in the Examples and the experimental condition in Example 14. The result is shown in FIG. 15. As in the case of Example 14, amplified cdtAs fragments specific to C. jejuni (about 630 bp), C. coli (about 330 bp), and C. fetus (about 490 bp) were found, allowing the discrimination of each species.

Example 18

Design of cdtC Specific Primers and Detection of cdtC Gene by Multiplex PCR

The CDT sequence of C. fetus of the present invention was compared with the CDT genes of C. jejuni and C. coli from known databases to design C. jejuni-specific primers CjCSPU1 and CjCSPR2 described below. Likewise, C. coli-specific primers CcCSPU1 and CcCSPR1, and C. fetus-specific primers CfCSPU2 and CfCSPR1 were designed.

The primers were combined and added to 1 µl of 20 ng/µl cell extract to give each primer concentration of 0.125 mM. The final volume was adjusted to 20 µl with PCR buffer (TaKaRa Ex Taq kit: Takara Bio). The reaction mixture was subjected to multiplex PCR under the condition of: 94° C. for 3 minutes, 30 cycles of [94° C. for 30 seconds, 55° C. for 30 seconds, and 72° C. for 30 seconds], and 72° C. for 3 minutes (GeneAmp PCR System 9700; Applied Biosystems). The result is shown in FIG. 14 (right). Amplified CDT fragments specific to C. jejuni (about 500 bp), C. coli (about 300 bp), and C. fetus (about 400 bp) were found, allowing the discrimination of C. jejuni (lanes 10 to 12), C. coli (lanes 13 and 14), and C. fetus (lanes 15 and 16).

```
Specific primer CjCSPU1
[SEQ ID NO: 74: TTTAGCCTTTGCAACTCCTA]

Specific primer CjCSPR2
[SEQ ID NO: 75: AAGGGGTAGCAGCTGTTAA]

Specific primer CcCSPU1
[SEQ ID NO: 76: TAGGGGATATGCACGCAAAAG]

Specific primer CcCSPR1
[SEQ ID NO: 77: GCTTAATACAGTTACGATAG]

Specific primer CfCSPU2
[SEQ ID NO: 78: AAGCATAAGTTTTGCAAACG]

Specific primer CfCSPR1
[SEQ ID NO: 79: GTTTGGATTTTCAAATGTTCC]
```

Example 19

Detection of cdtC Gene by Multiplex PCR Using Specific Primers

Multiplex PCR was performed on other various clinical strains of Campylobacter bacteria using the specific primers obtained in the Examples and the experimental condition in Example 14. The result is shown in FIG. 16. As in the case of Example 14, amplified CdtC fragments specific to C. jejuni (about 500 bp), C. coli (about 300 bp), and C. fetus (about 400 bp) were found, allowing the discrimination of each species.

INDUSTRIAL APPLICABILITY

The primers of the present invention are applicable not only to epidemiologic studies and researches on Campylobacter bacteria and diagnosis of campylobacteriosis but also to the rapid examination of foods contaminated with Campylobacter bacteria, validation of food processing processes, and rapid identification of the causative bacteria at the time of food poisoning outbreak, and therefore useful in preventing expansion of infection.

SEQUENCE LISTING

<160> NUMBER OF SEQ ID NOS: 79

<210> SEQ ID NO 1
<211> LENGTH: 2211
<212> TYPE: DNA
<213> ORGANISM: Campylobacter coli
<220> FEATURE:
<221> NAME/KEY: CDS
<222> LOCATION: (1)..(777)
<220> FEATURE:
<221> NAME/KEY: CDS
<222> LOCATION: (802)..(1605)
<220> FEATURE:
<221> NAME/KEY: CDS
<222> LOCATION: (1615)..(2187)

<400> SEQUENCE: 1

```
atg caa aaa ata aaa tta agc cta atg ttt ttg att gta aca atc att        48
Met Gln Lys Ile Lys Leu Ser Leu Met Phe Leu Ile Val Thr Ile Ile
1               5                   10                  15 ttt tta gct tgt tct tca aaa gaa caa caa atc aat cct tta gga aga        96
Phe Leu Ala Cys Ser Ser Lys Glu Gln Gln Ile Asn Pro Leu Gly Arg
            20                  25                  30 tct tac ggt aaa ttt aac gat aac gat cct tta aaa ctt ggt tca aaa      144
Ser Tyr Gly Lys Phe Asn Asp Asn Asp Pro Leu Lys Leu Gly Ser Lys
        35                  40                  45 cct aca ccc cct gtc aaa caa aaa aca cca agc ttg gta gaa ggt aaa      192
Pro Thr Pro Pro Val Lys Gln Lys Thr Pro Ser Leu Val Glu Gly Lys
    50                  55                  60 aaa ttt ccc gcc ata cca ctt gtc cca cct gta atc act cct aat acc      240
Lys Phe Pro Ala Ile Pro Leu Val Pro Pro Val Ile Thr Pro Asn Thr
65                  70                  75                  80 ttt aaa gga gat aat gcc gtc aaa ggc cca ttg cca agg cta aaa tct      288
Phe Lys Gly Asp Asn Ala Val Lys Gly Pro Leu Pro Arg Leu Lys Ser
                85                  90                  95 cca aac gaa ttt gct tca aat gct tta tac gaa aac aca ggt atg gta      336
Pro Asn Glu Phe Ala Ser Asn Ala Leu Tyr Glu Asn Thr Gly Met Val
            100                 105                 110 agt gat ttt gtc act att atg aat cct aat gga gca tct tta aca atc      384
Ser Asp Phe Val Thr Ile Met Asn Pro Asn Gly Ala Ser Leu Thr Ile
        115                 120                 125 tgg gct tta aat cct ggc aat tgg ata tgg gga tat agt tta ttt gct      432
Trp Ala Leu Asn Pro Gly Asn Trp Ile Trp Gly Tyr Ser Leu Phe Ala
    130                 135                 140 agt aga cct ttt gga gat gca aga gct tgg cag ctt att gaa ttt cca      480
Ser Arg Pro Phe Gly Asp Ala Arg Ala Trp Gln Leu Ile Glu Phe Pro
145                 150                 155                 160 aac aat aca gta atg att aaa aat gca aaa aca ttt act tgc tta aac      528
Asn Asn Thr Val Met Ile Lys Asn Ala Lys Thr Phe Thr Cys Leu Asn
                165                 170                 175 gcc tat aga aat ggc atc gtt cat tat cct tgt gat caa aca aat ttt      576
Ala Tyr Arg Asn Gly Ile Val His Tyr Pro Cys Asp Gln Thr Asn Phe
            180                 185                 190 gcg cag ttt tgg aga ctt tat ccg atg act aat gga gct tat caa att      624
Ala Gln Phe Trp Arg Leu Tyr Pro Met Thr Asn Gly Ala Tyr Gln Ile
        195                 200                 205 caa aat ttt gcc acc caa caa tgt ata caa aca cct gtt tca aat gta      672
Gln Asn Phe Ala Thr Gln Gln Cys Ile Gln Thr Pro Val Ser Asn Val
    210                 215                 220 atg gaa gaa ttt aat ttg agc ttt tat aat att tat tta acc gat tgt      720
Met Glu Glu Phe Asn Leu Ser Phe Tyr Asn Ile Tyr Leu Thr Asp Cys
```

-continued

```
                225                 230                 235                 240 ttg aaa gaa aaa gaa aag aat ttg gat aga cag tgg tat ata ggc gct            768
Leu Lys Glu Lys Glu Lys Asn Leu Asp Arg Gln Trp Tyr Ile Gly Ala
                245                 250                 255 cct att taa tttttttcgct atgaaaggaa gata atg aaa aaa ata gta ttt           819
Pro Ile                                    Met Lys Lys Ile Val Phe
                                               260 ttg att tta agt ttt aat gta tta ttt gcc gct tta gaa aat tac aac            867
Leu Ile Leu Ser Phe Asn Val Leu Phe Ala Ala Leu Glu Asn Tyr Asn
265                 270                 275                 280 acc gga act tgg aat ttg caa ggc tca tca gct gca act gaa agc aaa            915
Thr Gly Thr Trp Asn Leu Gln Gly Ser Ser Ala Ala Thr Glu Ser Lys
                285                 290                 295 tgg aat gtt agt ata aga caa ctc ata acc ggt gca aat cct atg gat            963
Trp Asn Val Ser Ile Arg Gln Leu Ile Thr Gly Ala Asn Pro Met Asp
                300                 305                 310 gtt tta gct gtt caa gaa gcg ggg gtt tta cct agt aca gct atg atg           1011
Val Leu Ala Val Gln Glu Ala Gly Val Leu Pro Ser Thr Ala Met Met
                315                 320                 325 act cct aga cag gta caa ccc gtg ggc gtg ggt att cct ata cat gaa           1059
Thr Pro Arg Gln Val Gln Pro Val Gly Val Gly Ile Pro Ile His Glu
                330                 335                 340 tac ata tgg aat tta ggc tct gta tca aga cct agc tct gtt tat ata           1107
Tyr Ile Trp Asn Leu Gly Ser Val Ser Arg Pro Ser Ser Val Tyr Ile
345                 350                 355                 360 tat tat tct aga gtg gat gta gga gca aat cgt gtg aat tta gct atc           1155
Tyr Tyr Ser Arg Val Asp Val Gly Ala Asn Arg Val Asn Leu Ala Ile
                365                 370                 375 gtt agc aga gtg caa gcg gat gaa gtt ttt gtt tta ccc cct cca aca           1203
Val Ser Arg Val Gln Ala Asp Glu Val Phe Val Leu Pro Pro Pro Thr
                380                 385                 390 gtt gct tca aga cct att ata ggc ata cgc ata ggc aat gat gct ttt           1251
Val Ala Ser Arg Pro Ile Ile Gly Ile Arg Ile Gly Asn Asp Ala Phe
                395                 400                 405 ttc aat ata cac gct cta gca agt ggg gga aat gac gca gga gcc att           1299
Phe Asn Ile His Ala Leu Ala Ser Gly Gly Asn Asp Ala Gly Ala Ile
410                 415                 420 gtc gct gct gtg gat atg ttt ttt aga aat aga cct gat att aat tgg           1347
Val Ala Ala Val Asp Met Phe Phe Arg Asn Arg Pro Asp Ile Asn Trp
425                 430                 435                 440 atg att tta ggc gat ttt aat aga gaa tca ggc gcc tta gta acc ttg           1395
Met Ile Leu Gly Asp Phe Asn Arg Glu Ser Gly Ala Leu Val Thr Leu
                445                 450                 455 cta gat cct gac tta aga gca cgc act cgc gta gtt gtt ccg cct tct           1443
Leu Asp Pro Asp Leu Arg Ala Arg Thr Arg Val Val Val Pro Pro Ser
                460                 465                 470 tct acg caa aca agt gga aga acg att gat tat gct atc act gga aat           1491
Ser Thr Gln Thr Ser Gly Arg Thr Ile Asp Tyr Ala Ile Thr Gly Asn
                475                 480                 485 tcc aac act gca gct tta tac aac cca cca ccg ata gtt gcg att tta           1539
Ser Asn Thr Ala Ala Leu Tyr Asn Pro Pro Pro Ile Val Ala Ile Leu
                490                 495                 500 gct tta gaa gga tta aga acc ttt ttg gct tca gat cat ttt cct gta           1587
Ala Leu Glu Gly Leu Arg Thr Phe Leu Ala Ser Asp His Phe Pro Val
505                 510                 515                 520 aat ttt aga aga cct tag gagcttaat atg aaa aaa ttt ttt att tta ttt         1638
Asn Phe Arg Arg Pro           Met Lys Lys Phe Phe Ile Leu Phe
                525                               530 ttt gcc ctt tgg agc ttt ttg aaa gca gag cct agc ttg gat gaa tta           1686
```

```
Phe Ala Leu Leu Ser Phe Leu Lys Ala Glu Pro Ser Leu Asp Glu Leu
    535                 540                 545 gca gac ttt act cct atg ttt gct ata aga tct tta gaa aca gga att      1734
Ala Asp Phe Thr Pro Met Phe Ala Ile Arg Ser Leu Glu Thr Gly Ile
550                 555                 560                 565 tct tta agt cct ttt aga aaa act tca aaa agg tta gaa gat caa aat      1782
Ser Leu Ser Pro Phe Arg Lys Thr Ser Lys Arg Leu Glu Asp Gln Asn
                570                 575                 580 tgg ttt tta aaa gag att gta gca aat gat gag cta aaa gct agg gat      1830
Trp Phe Leu Lys Glu Ile Val Ala Asn Asp Glu Leu Lys Ala Arg Asp
585                 590                 595 atg cac gca aaa gat ttg cct ttt ggc tat gtt cag ttt ata agc cct      1878
Met His Ala Lys Asp Leu Pro Phe Gly Tyr Val Gln Phe Ile Ser Pro
            600                 605                 610 agg ggc gat gat ata tgc cta gct gtt tta agt gaa aaa agt ttt ggc      1926
Arg Gly Asp Asp Ile Cys Leu Ala Val Leu Ser Glu Lys Ser Phe Gly
        615                 620                 625 acc aaa tct tgc aaa caa gat ttg caa gat gga aca atg cag act att      1974
Thr Lys Ser Cys Lys Gln Asp Leu Gln Asp Gly Thr Met Gln Thr Ile
630                 635                 640                 645 ttt tct atc ata cca atg aca aat ggt tct ata caa att aga tct tta      2022
Phe Ser Ile Ile Pro Met Thr Asn Gly Ser Ile Gln Ile Arg Ser Leu
                650                 655                 660 acc aat ggt ggc aat caa tgc atg agc act ttt cct gac tct agt atc      2070
Thr Asn Gly Gly Asn Gln Cys Met Ser Thr Phe Pro Asp Ser Ser Ile
            665                 670                 675 gcc ata gaa aat cgc ttt ggt tta gga gaa tgc ctt ttg gat cgt tct      2118
Ala Ile Glu Asn Arg Phe Gly Leu Gly Glu Cys Leu Leu Asp Arg Ser
        680                 685                 690 atc gta act gta tta agc aaa ctt ttc ttt ttc tcc cct gct ata atc      2166
Ile Val Thr Val Leu Ser Lys Leu Phe Phe Phe Ser Pro Ala Ile Ile
695                 700                 705 gaa gca agc gca att tac taa cacttttcta acaaaaccaa gctt              2211
Glu Ala Ser Ala Ile Tyr
710                 715

<210> SEQ ID NO 2
<211> LENGTH: 258
<212> TYPE: PRT
<213> ORGANISM: Campylobacter coli

<400> SEQUENCE: 2

Met Gln Lys Ile Lys Leu Ser Leu Met Phe Leu Ile Val Thr Ile Ile
1               5                   10                  15

Phe Leu Ala Cys Ser Ser Lys Glu Gln Gln Ile Asn Pro Leu Gly Arg
            20                  25                  30

Ser Tyr Gly Lys Phe Asn Asp Asn Asp Pro Leu Lys Leu Gly Ser Lys
        35                  40                  45

Pro Thr Pro Pro Val Lys Gln Lys Thr Pro Ser Leu Val Glu Gly Lys
    50                  55                  60

Lys Phe Pro Ala Ile Pro Leu Val Pro Pro Val Ile Thr Pro Asn Thr
65                  70                  75                  80

Phe Lys Gly Asp Asn Ala Val Lys Gly Pro Leu Pro Arg Leu Lys Ser
                85                  90                  95

Pro Asn Glu Phe Ala Ser Asn Ala Leu Tyr Glu Asn Thr Gly Met Val
            100                 105                 110

Ser Asp Phe Val Thr Ile Met Asn Pro Asn Gly Ala Ser Leu Thr Ile
        115                 120                 125
```

```
Trp Ala Leu Asn Pro Gly Asn Trp Ile Trp Gly Tyr Ser Leu Phe Ala
        130                 135                 140

Ser Arg Pro Phe Gly Asp Ala Arg Ala Trp Gln Leu Ile Glu Phe Pro
145                 150                 155                 160

Asn Asn Thr Val Met Ile Lys Asn Ala Lys Thr Phe Thr Cys Leu Asn
                165                 170                 175

Ala Tyr Arg Asn Gly Ile Val His Tyr Pro Cys Asp Gln Thr Asn Phe
            180                 185                 190

Ala Gln Phe Trp Arg Leu Tyr Pro Met Thr Asn Gly Ala Tyr Gln Ile
        195                 200                 205

Gln Asn Phe Ala Thr Gln Gln Cys Ile Gln Thr Pro Val Ser Asn Val
    210                 215                 220

Met Glu Glu Phe Asn Leu Ser Phe Tyr Asn Ile Tyr Leu Thr Asp Cys
225                 230                 235                 240

Leu Lys Glu Lys Glu Lys Asn Leu Asp Arg Gln Trp Tyr Ile Gly Ala
                245                 250                 255

Pro Ile

<210> SEQ ID NO 3
<211> LENGTH: 267
<212> TYPE: PRT
<213> ORGANISM: Campylobacter coli

<400> SEQUENCE: 3

Met Lys Lys Ile Val Phe Leu Ile Leu Ser Phe Asn Val Leu Phe Ala
1               5                   10                  15

Ala Leu Glu Asn Tyr Asn Thr Gly Thr Trp Asn Leu Gln Gly Ser Ser
            20                  25                  30

Ala Ala Thr Glu Ser Lys Trp Asn Val Ser Ile Arg Gln Leu Ile Thr
        35                  40                  45

Gly Ala Asn Pro Met Asp Val Leu Ala Val Gln Glu Ala Gly Val Leu
    50                  55                  60

Pro Ser Thr Ala Met Met Thr Pro Arg Gln Val Gln Pro Val Gly Val
65                  70                  75                  80

Gly Ile Pro Ile His Glu Tyr Ile Trp Asn Leu Gly Ser Val Ser Arg
                85                  90                  95

Pro Ser Ser Val Tyr Ile Tyr Tyr Ser Arg Val Asp Val Gly Ala Asn
            100                 105                 110

Arg Val Asn Leu Ala Ile Val Ser Arg Val Gln Ala Asp Glu Val Phe
        115                 120                 125

Val Leu Pro Pro Pro Thr Val Ala Ser Arg Pro Ile Ile Gly Ile Arg
    130                 135                 140

Ile Gly Asn Asp Ala Phe Phe Asn Ile His Ala Leu Ala Ser Gly Gly
145                 150                 155                 160

Asn Asp Ala Gly Ala Ile Val Ala Val Asp Met Phe Phe Arg Asn
                165                 170                 175

Arg Pro Asp Ile Asn Trp Met Ile Leu Gly Asp Phe Asn Arg Glu Ser
            180                 185                 190

Gly Ala Leu Val Thr Leu Leu Asp Pro Asp Leu Arg Ala Arg Thr Arg
        195                 200                 205

Val Val Val Pro Pro Ser Ser Thr Gln Thr Ser Gly Arg Thr Ile Asp
    210                 215                 220

Tyr Ala Ile Thr Gly Asn Ser Asn Thr Ala Ala Leu Tyr Asn Pro Pro
225                 230                 235                 240
```

```
Pro Ile Val Ala Ile Leu Ala Leu Glu Gly Leu Arg Thr Phe Leu Ala
                245                 250                 255

Ser Asp His Phe Pro Val Asn Phe Arg Arg Pro
            260                 265

<210> SEQ ID NO 4
<211> LENGTH: 190
<212> TYPE: PRT
<213> ORGANISM: Campylobacter coli

<400> SEQUENCE: 4

Met Lys Lys Phe Phe Ile Leu Phe Phe Ala Leu Leu Ser Phe Leu Lys
1               5                   10                  15

Ala Glu Pro Ser Leu Asp Glu Leu Ala Asp Phe Thr Pro Met Phe Ala
            20                  25                  30

Ile Arg Ser Leu Glu Thr Gly Ile Ser Leu Ser Pro Phe Arg Lys Thr
        35                  40                  45

Ser Lys Arg Leu Glu Asp Gln Asn Trp Phe Leu Lys Glu Ile Val Ala
    50                  55                  60

Asn Asp Glu Leu Lys Ala Arg Asp Met His Ala Lys Asp Leu Pro Phe
65                  70                  75                  80

Gly Tyr Val Gln Phe Ile Ser Pro Arg Gly Asp Asp Ile Cys Leu Ala
                85                  90                  95

Val Leu Ser Glu Lys Ser Phe Gly Thr Lys Ser Cys Lys Gln Asp Leu
            100                 105                 110

Gln Asp Gly Thr Met Gln Thr Ile Phe Ser Ile Ile Pro Met Thr Asn
        115                 120                 125

Gly Ser Ile Gln Ile Arg Ser Leu Thr Asn Gly Gly Asn Gln Cys Met
    130                 135                 140

Ser Thr Phe Pro Asp Ser Ser Ile Ala Ile Glu Asn Arg Phe Gly Leu
145                 150                 155                 160

Gly Glu Cys Leu Leu Asp Arg Ser Ile Val Thr Val Leu Ser Lys Leu
                165                 170                 175

Phe Phe Phe Ser Pro Ala Ile Ile Glu Ala Ser Ala Ile Tyr
            180                 185                 190

<210> SEQ ID NO 5
<211> LENGTH: 20
<212> TYPE: DNA
<213> ORGANISM: Artificial
<220> FEATURE:
<223> OTHER INFORMATION: an artificially synthesized primer sequence
<220> FEATURE:
<221> NAME/KEY: misc_feature
<222> LOCATION: (3)..(3)
<223> OTHER INFORMATION: n = a, c, g, or t
<220> FEATURE:
<221> NAME/KEY: misc_feature
<222> LOCATION: (6)..(6)
<223> OTHER INFORMATION: n = c or t
<220> FEATURE:
<221> NAME/KEY: misc_feature
<222> LOCATION: (12)..(12)
<223> OTHER INFORMATION: n = a, c or t
<220> FEATURE:
<221> NAME/KEY: misc_feature
<222> LOCATION: (18)..(18)
<223> OTHER INFORMATION: n =a, c, g or t

<400> SEQUENCE: 5
ggnaantgga tntggggnta                                                   20
```

```
<210> SEQ ID NO 6
<211> LENGTH: 21
<212> TYPE: DNA
<213> ORGANISM: Artificial
<220> FEATURE:
<223> OTHER INFORMATION: an artificially synthesized primer sequence
<220> FEATURE:
<221> NAME/KEY: misc_feature
<222> LOCATION: (1)..(1)
<223> OTHER INFORMATION: "n" = a, g or t
<220> FEATURE:
<221> NAME/KEY: misc_feature
<222> LOCATION: (4)..(4)
<223> OTHER INFORMATION: "n" = c or t
<220> FEATURE:
<221> NAME/KEY: misc_feature
<222> LOCATION: (7)..(7)
<223> OTHER INFORMATION: "n" = a, c, g or t
<220> FEATURE:
<221> NAME/KEY: misc_feature
<222> LOCATION: (10)..(10)
<223> OTHER INFORMATION: "n" = a, g or t
<220> FEATURE:
<221> NAME/KEY: misc_feature
<222> LOCATION: (13)..(13)
<223> OTHER INFORMATION: "n" = a, c, g or t
<220> FEATURE:
<221> NAME/KEY: misc_feature
<222> LOCATION: (16)..(16)
<223> OTHER INFORMATION: "n" = a, g or t
<220> FEATURE:
<221> NAME/KEY: misc_feature
<222> LOCATION: (19)..(19)
<223> OTHER INFORMATION: "n" = a, c, g or t

<400> SEQUENCE: 6
naantgnacn tanccnaang g                                             21

<210> SEQ ID NO 7
<211> LENGTH: 20
<212> TYPE: DNA
<213> ORGANISM: Artificial
<220> FEATURE:
<223> OTHER INFORMATION: an artificially synthesized primer sequence
<220> FEATURE:
<221> NAME/KEY: misc_feature
<222> LOCATION: (6)..(6)
<223> OTHER INFORMATION: "n" = c or t

<400> SEQUENCE: 7
gataangatc ctttaaaact                                               20

<210> SEQ ID NO 8
<211> LENGTH: 21
<212> TYPE: DNA
<213> ORGANISM: Artificial
<220> FEATURE:
<223> OTHER INFORMATION: an artificially synthesized primer sequence
<220> FEATURE:
<221> NAME/KEY: misc_feature
<222> LOCATION: (1)..(1)
<223> OTHER INFORMATION: "n" = a or t
<220> FEATURE:
<221> NAME/KEY: misc_feature
<222> LOCATION: (2)..(2)
<223> OTHER INFORMATION: "n" = a or t
<220> FEATURE:
<221> NAME/KEY: misc_feature
<222> LOCATION: (11)..(11)
<223> OTHER INFORMATION: "n" = a or t
<220> FEATURE:
<221> NAME/KEY: misc_feature
<222> LOCATION: (16)..(16)
<223> OTHER INFORMATION: "n" = c or g
```

-continued

```
<400> SEQUENCE: 8
nnccaaagcg nttttntatg g                                          21

<210> SEQ ID NO 9
<211> LENGTH: 18
<212> TYPE: DNA
<213> ORGANISM: Artificial
<220> FEATURE:
<223> OTHER INFORMATION: an artificially synthesized primer sequence

<400> SEQUENCE: 9
acttggaatt tgcaaggc                                              18

<210> SEQ ID NO 10
<211> LENGTH: 21
<212> TYPE: DNA
<213> ORGANISM: Artificial
<220> FEATURE:
<223> OTHER INFORMATION: an artificially synthesized primer sequence
<220> FEATURE:
<221> NAME/KEY: misc_feature
<222> LOCATION: (13)..(13)
<223> OTHER INFORMATION: "n" = a, c or t

<400> SEQUENCE: 10
tctaaaattt acnggaaaat g                                          21

<210> SEQ ID NO 11
<211> LENGTH: 19
<212> TYPE: DNA
<213> ORGANISM: Artificial
<220> FEATURE:
<223> OTHER INFORMATION: an artificially synthesized primer sequence

<400> SEQUENCE: 11
tactccgcct tttaccgca                                             19

<210> SEQ ID NO 12
<211> LENGTH: 18
<212> TYPE: DNA
<213> ORGANISM: Artificial
<220> FEATURE:
<223> OTHER INFORMATION: an artificially synthesized primer sequence

<400> SEQUENCE: 12
gagtataggt ttgttgtc                                              18

<210> SEQ ID NO 13
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 13
tttaatgtat tatttgccgc                                            20

<210> SEQ ID NO 14
<211> LENGTH: 18
<212> TYPE: DNA
<213> ORGANISM: Artificial
<220> FEATURE:
<223> OTHER INFORMATION: an artificially synthesized primer sequence

<400> SEQUENCE: 14
tcattgccta tgcgtatg                                              18
```

<210> SEQ ID NO 15
<211> LENGTH: 18
<212> TYPE: DNA
<213> ORGANISM: Artificial
<220> FEATURE:
<223> OTHER INFORMATION: an artificially synthesized primer sequence

<400> SEQUENCE: 15
cgcaagttgg aagactat                                                 18

<210> SEQ ID NO 16
<211> LENGTH: 18
<212> TYPE: DNA
<213> ORGANISM: Artificial
<220> FEATURE:
<223> OTHER INFORMATION: an artificially synthesized primer sequence

<400> SEQUENCE: 16
tttattatcg ccggagca                                                 18

<210> SEQ ID NO 17
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 17
attatatgtt tatttttatc                                               20

<210> SEQ ID NO 18
<211> LENGTH: 18
<212> TYPE: DNA
<213> ORGANISM: Artificial
<220> FEATURE:
<223> OTHER INFORMATION: an artificially synthesized primer sequence

<400> SEQUENCE: 18
ccacagaaag caaatgga                                                 18

<210> SEQ ID NO 19
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 19
agccactcca acaggacgcc                                               20

<210> SEQ ID NO 20
<211> LENGTH: 24
<212> TYPE: DNA
<213> ORGANISM: Artificial
<220> FEATURE:
<223> OTHER INFORMATION: an artificially synthesized primer sequence

<400> SEQUENCE: 20
tgatgaatat gagtggaatt tagg                                          24

<210> SEQ ID NO 21
<211> LENGTH: 19
<212> TYPE: DNA
<213> ORGANISM: Artificial
<220> FEATURE:

<223> OTHER INFORMATION: an artificially synthesized primer sequence

<400> SEQUENCE: 21
ttcaagaatg caagctgaa						19

<210> SEQ ID NO 22
<211> LENGTH: 16
<212> TYPE: DNA
<213> ORGANISM: Artificial
<220> FEATURE:
<223> OTHER INFORMATION: an artificially synthesized primer sequence

<400> SEQUENCE: 22
cagctgtaga tgcaca						16

<210> SEQ ID NO 23
<211> LENGTH: 22
<212> TYPE: DNA
<213> ORGANISM: Artificial
<220> FEATURE:
<223> OTHER INFORMATION: an artificially synthesized primer sequence

<400> SEQUENCE: 23
tgatccttct actataacaa gt						22

<210> SEQ ID NO 24
<211> LENGTH: 18
<212> TYPE: DNA
<213> ORGANISM: Artificial
<220> FEATURE:
<223> OTHER INFORMATION: an artificially synthesized primer sequence

<400> SEQUENCE: 24
gacaacaaac ctatactc						18

<210> SEQ ID NO 25
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 25
gcaagtttaa gatctcatat						20

<210> SEQ ID NO 26
<211> LENGTH: 23
<212> TYPE: DNA
<213> ORGANISM: Artificial
<220> FEATURE:
<223> OTHER INFORMATION: an artificially synthesized primer sequence

<400> SEQUENCE: 26 cccccttagat atcttaatga tac						23

<210> SEQ ID NO 27
<211> LENGTH: 19
<212> TYPE: DNA
<213> ORGANISM: Artificial
<220> FEATURE:
<223> OTHER INFORMATION: an artificially synthesized primer sequence

<400> SEQUENCE: 27
tgcaacaagg tggaacacc						19

```
<210> SEQ ID NO 28
<211> LENGTH: 19
<212> TYPE: DNA
<213> ORGANISM: Artificial
<220> FEATURE:
<223> OTHER INFORMATION: an artificially synthesized primer sequence

<400> SEQUENCE: 28
caacccacca ccgatagtt                                                  19

<210> SEQ ID NO 29
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 29
agccactcca acaggacgcc                                                 20

<210> SEQ ID NO 30
<211> LENGTH: 21
<212> TYPE: DNA
<213> ORGANISM: Artificial
<220> FEATURE:
<223> OTHER INFORMATION: an artificially synthesized primer sequence

<400> SEQUENCE: 30
ctgtatcaag acctagctct g                                               21

<210> SEQ ID NO 31
<211> LENGTH: 18
<212> TYPE: DNA
<213> ORGANISM: Artificial
<220> FEATURE:
<223> OTHER INFORMATION: an artificially synthesized primer sequence

<400> SEQUENCE: 31
catacgcata ggcaatga                                                   18

<210> SEQ ID NO 32
<211> LENGTH: 22
<212> TYPE: DNA
<213> ORGANISM: Artificial
<220> FEATURE:
<223> OTHER INFORMATION: an artificially synthesized primer sequence

<400> SEQUENCE: 32
cgcaggagcc attgtcgctg ct                                              22

<210> SEQ ID NO 33
<211> LENGTH: 21
<212> TYPE: DNA
<213> ORGANISM: Artificial
<220> FEATURE:
<223> OTHER INFORMATION: an artificially synthesized primer sequence

<400> SEQUENCE: 33
tgacttaaga gcacgcactc g                                               21

<210> SEQ ID NO 34
<211> LENGTH: 19
<212> TYPE: DNA
<213> ORGANISM: Artificial
<220> FEATURE:
<223> OTHER INFORMATION: an artificially synthesized primer sequence
```

```
<400> SEQUENCE: 34
ggattaagaa ccttttttgg                                                    19

<210> SEQ ID NO 35
<211> LENGTH: 22
<212> TYPE: DNA
<213> ORGANISM: Artificial
<220> FEATURE:
<223> OTHER INFORMATION: an artificially synthesized primer sequence

<400> SEQUENCE: 35
aagaccttag gagcttaata tg                                                 22

<210> SEQ ID NO 36
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 36
cgtagttgtt ccgccttctt                                                    20

<210> SEQ ID NO 37
<211> LENGTH: 23
<212> TYPE: DNA
<213> ORGANISM: Artificial
<220> FEATURE:
<223> OTHER INFORMATION: an artificially synthesized primer sequence

<400> SEQUENCE: 37
gcgtcagagt aacgttttta aca                                                23

<210> SEQ ID NO 38
<211> LENGTH: 23
<212> TYPE: DNA
<213> ORGANISM: Artificial
<220> FEATURE:
<223> OTHER INFORMATION: an artificially synthesized primer sequence

<400> SEQUENCE: 38
ttatatttat agcaacttta ggc                                                23

<210> SEQ ID NO 39
<211> LENGTH: 23
<212> TYPE: DNA
<213> ORGANISM: Artificial
<220> FEATURE:
<223> OTHER INFORMATION: an artificially synthesized primer sequence

<400> SEQUENCE: 39
aaatttacct caaaccgctc ttc                                                23

<210> SEQ ID NO 40
<211> LENGTH: 23
<212> TYPE: DNA
<213> ORGANISM: Artificial
<220> FEATURE:
<223> OTHER INFORMATION: an artificially synthesized primer sequence

<400> SEQUENCE: 40
aagcataaat caaggcgacg atc                                                23

<210> SEQ ID NO 41
<211> LENGTH: 20
```

```
<212> TYPE: DNA
<213> ORGANISM: Artificial
<220> FEATURE:
<223> OTHER INFORMATION: an artificially synthesized primer sequence

<400> SEQUENCE: 41
gtatatctag accgttccaa                                                    20

<210> SEQ ID NO 42
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 42
aaatcatcat cttgccgcct                                                    20

<210> SEQ ID NO 43
<211> LENGTH: 22
<212> TYPE: DNA
<213> ORGANISM: Artificial
<220> FEATURE:
<223> OTHER INFORMATION: an artificially synthesized primer sequence

<400> SEQUENCE: 43
ggaactcttg gattagaaac tc                                                 22

<210> SEQ ID NO 44
<211> LENGTH: 23
<212> TYPE: DNA
<213> ORGANISM: Artificial
<220> FEATURE:
<223> OTHER INFORMATION: an artificially synthesized primer sequence

<400> SEQUENCE: 44
gcgtcagagt aacgttttta aca                                                23

<210> SEQ ID NO 45
<211> LENGTH: 21
<212> TYPE: DNA
<213> ORGANISM: Artificial
<220> FEATURE:
<223> OTHER INFORMATION: an artificially synthesized primer sequence

<400> SEQUENCE: 45
agccggcgat cttgtccgaa c                                                  21

<210> SEQ ID NO 46
<211> LENGTH: 21
<212> TYPE: DNA
<213> ORGANISM: Artificial
<220> FEATURE:
<223> OTHER INFORMATION: an artificially synthesized primer sequence

<400> SEQUENCE: 46
gcaaacctgc ggactcacct a                                                  21

<210> SEQ ID NO 47
<211> LENGTH: 18
<212> TYPE: DNA
<213> ORGANISM: Artificial
<220> FEATURE:
<223> OTHER INFORMATION: an artificially synthesized primer sequence

<400> SEQUENCE: 47
```

-continued

| | |
|---|---|
| ccacagaaag caaatgga | 18 |

<210> SEQ ID NO 48
<211> LENGTH: 26
<212> TYPE: DNA
<213> ORGANISM: Artificial
<220> FEATURE:
<223> OTHER INFORMATION: an artificially synthesized primer sequence

<400> SEQUENCE: 48

| | |
|---|---|
| ctaatcgtgt aaatttagct atagtt | 26 |

<210> SEQ ID NO 49
<211> LENGTH: 23
<212> TYPE: DNA
<213> ORGANISM: Artificial
<220> FEATURE:
<223> OTHER INFORMATION: an artificially synthesized primer sequence

<400> SEQUENCE: 49

| | |
|---|---|
| tttttcaata tccatgcttt agc | 23 |

<210> SEQ ID NO 50
<211> LENGTH: 23
<212> TYPE: DNA
<213> ORGANISM: Artificial
<220> FEATURE:
<223> OTHER INFORMATION: an artificially synthesized primer sequence

<400> SEQUENCE: 50

| | |
|---|---|
| tggatgatag cagggatttt taa | 23 |

<210> SEQ ID NO 51
<211> LENGTH: 2180
<212> TYPE: DNA
<213> ORGANISM: Campylobacter fetus
<220> FEATURE:
<221> NAME/KEY: CDS
<222> LOCATION: (1)..(702)
<220> FEATURE:
<221> NAME/KEY: CDS
<222> LOCATION: (778)..(1629)
<220> FEATURE:
<221> NAME/KEY: CDS
<222> LOCATION: (1632)..(2177)

<400> SEQUENCE: 51

| | | |
|---|---|---|
| atg act aaa att att ttc aag cat att aaa aat agt ctt att tta cta<br>Met Thr Lys Ile Ile Phe Lys His Ile Lys Asn Ser Leu Ile Leu Leu<br>1               5                   10                  15 | | 48 |
| ttt tgt atc gct ctt ttt agt gct tgc tca tca aaa acg aca aat gta<br>Phe Cys Ile Ala Leu Phe Ser Ala Cys Ser Ser Lys Thr Thr Asn Val<br>            20                  25                  30 | | 96 |
| agc act caa aaa ata aat cca tta gga agc att ttt ggc aaa acg gat<br>Ser Thr Gln Lys Ile Asn Pro Leu Gly Ser Ile Phe Gly Lys Thr Asp<br>        35                  40                  45 | | 144 |
| gat cca gat cca cta aat tta ggc gat ttt cca act ctt cta aca tca<br>Asp Pro Asp Pro Leu Asn Leu Gly Asp Phe Pro Thr Leu Leu Thr Ser<br>    50                  55                  60 | | 192 |
| aat ttt aca aat cct atg ccg act aga acg cca tcg cca ctt aaa aaa<br>Asn Phe Thr Asn Pro Met Pro Thr Arg Thr Pro Ser Pro Leu Lys Lys<br>65                  70                  75                  80 | | 240 |
| gtg gat ttg cct gta atg aac tca tta aca cat ggt ccg atg ttt tca<br>Val Asp Leu Pro Val Met Asn Ser Leu Thr His Gly Pro Met Phe Ser<br>                85                  90                  95 | | 288 |

-continued

| | |
|---|---|
| agt gct ttt agt aaa ccg gac ttg aat ttc aaa caa cct act atc agt<br>Ser Ala Phe Ser Lys Pro Asp Leu Asn Phe Lys Gln Pro Thr Ile Ser<br>               100                    105                   110 | 336 |
| cta caa ggt atc ccg cct gat cta ttt gat aga aca agc gat ttt atg<br>Leu Gln Gly Ile Pro Pro Asp Leu Phe Asp Arg Thr Ser Asp Phe Met<br>               115                    120                   125 | 384 |
| gtg ata atg ggt gca aac ggc gtt gtg atc act att tgg tac aca tct<br>Val Ile Met Gly Ala Asn Gly Val Val Ile Thr Ile Trp Tyr Thr Ser<br>130                    135                    140 | 432 |
| cct gga aac tgg tta tgg ggc tac tcg ctc tat gaa agc ggc aat tta<br>Pro Gly Asn Trp Leu Trp Gly Tyr Ser Leu Tyr Glu Ser Gly Asn Leu<br>145                    150                    155                   160 | 480 |
| gga gga tat cgt gtt tgg cgt cta att tta cta cca aat aat gaa gtc<br>Gly Gly Tyr Arg Val Trp Arg Leu Ile Leu Leu Pro Asn Asn Glu Val<br>               165                    170                   175 | 528 |
| atg ata gta aat ttc aac act cgc acg act tgc ata aat act tat aaa<br>Met Ile Val Asn Phe Asn Thr Arg Thr Thr Cys Ile Asn Thr Tyr Lys<br>180                    185                    190 | 576 |
| aac gga gta att cac tca cct tgc aat aaa gat aat cct ttt cag aaa<br>Asn Gly Val Ile His Ser Pro Cys Asn Lys Asp Asn Pro Phe Gln Lys<br>               195                    200                   205 | 624 |
| ttt acg ttt cgt cca atg aca aac gga gcc gta caa att tat aac aaa<br>Phe Thr Phe Arg Pro Met Thr Asn Gly Ala Val Gln Ile Tyr Asn Lys<br>210                    215                    220 | 672 |
| gct act aat tgc gtg ctt gca aac gcc tgt taataatcta ttcggttttg<br>Ala Thr Asn Cys Val Leu Ala Asn Ala Cys<br>225                    230 | 722 |
| acgttttggg ggcgataaat cttacgacaa aatgcactga tactatcgat caaca atg<br>                                                                                                                                                                     Met<br>                                                                                                                                                                           235 | 780 |
| gta ttt gct ccc gcc gcc gca agt tgg aag act att tta tta gga gta<br>Val Phe Ala Pro Ala Ala Ala Ser Trp Lys Thr Ile Leu Leu Gly Val<br>                             240                    245                    250 | 828 |
| aaa atg cga aat gtt att atg att ata ttt ata gca act tta ggc ttt<br>Lys Met Arg Asn Val Ile Met Ile Ile Phe Ile Ala Thr Leu Gly Phe<br>                           255                              260                    265 | 876 |
| gca aaa cca gaa gat tat aaa att gct act tgg aat ttg caa ggc agt<br>Ala Lys Pro Glu Asp Tyr Lys Ile Ala Thr Trp Asn Leu Gln Gly Ser<br>                           270                              275                    280 | 924 |
| tcg gct ata acc gaa agc aaa tgg aat ata agc gta cgt caa ata att<br>Ser Ala Ile Thr Glu Ser Lys Trp Asn Ile Ser Val Arg Gln Ile Ile<br>285                    290                    295 | 972 |
| agc ggt gaa aat cca gca gat ata tta gcc gtt caa gaa gca gga aat<br>Ser Gly Glu Asn Pro Ala Asp Ile Leu Ala Val Gln Glu Ala Gly Asn<br>300                    305                    310                    315 | 1020 |
| tta cct caa acc gct ctt cct aca ggt aga agc ata aat caa ggc ggc<br>Leu Pro Gln Thr Ala Leu Pro Thr Gly Arg Ser Ile Asn Gln Gly Gly<br>                           320                              325                    330 | 1068 |
| acg atc gta act gag cat tta tgg cag cta ggc agt ata tct aga ccg<br>Thr Ile Val Thr Glu His Leu Trp Gln Leu Gly Ser Ile Ser Arg Pro<br>                           335                              340                    345 | 1116 |
| ttc caa gtc tat ata tat tat gct caa atc gac aca ggg gca aat aga<br>Phe Gln Val Tyr Ile Tyr Tyr Ala Gln Ile Asp Thr Gly Ala Asn Arg<br>               350                    355                    360 | 1164 |
| gta aat tta gca atc gtt tca cgc ata aaa gct gat gaa atc atc atc<br>Val Asn Leu Ala Ile Val Ser Arg Ile Lys Ala Asp Glu Ile Ile Ile<br>365                    370                    375 | 1212 |
| ttg ccg cct cct acg gta gct tct cgt ccg ctc ata ggt ata aga ata<br>Leu Pro Pro Pro Thr Val Ala Ser Arg Pro Leu Ile Gly Ile Arg Ile<br>380                    385                    390                    395 | 1260 |

-continued

```
gga aac gac gta ttt ttc aac ata cac gct cta gca aat ggc gga gtc    1308
Gly Asn Asp Val Phe Phe Asn Ile His Ala Leu Ala Asn Gly Gly Val
                400                 405                 410 gat gct ccg gcg ata ata aat tca ata ttt gac aga ttt aga aat atg    1356
Asp Ala Pro Ala Ile Ile Asn Ser Ile Phe Asp Arg Phe Arg Asn Met
            415                 420                 425 cca aat atc act tgg atg att tta ggc gat ttt aac cgc tca cct gag    1404
Pro Asn Ile Thr Trp Met Ile Leu Gly Asp Phe Asn Arg Ser Pro Glu
        430                 435                 440 agt tta aga gga act ctt gga tta gaa act cgc gtc aga gta acg ttt    1452
Ser Leu Arg Gly Thr Leu Gly Leu Glu Thr Arg Val Arg Val Thr Phe
    445                 450                 455 tta aca cct ccg gcg cct act caa aga agc ggc gga acg ctt gac tgg    1500
Leu Thr Pro Pro Ala Pro Thr Gln Arg Ser Gly Gly Thr Leu Asp Trp
460                 465                 470                 475 gct ata gtt gga aac tca gcc ggc gat ctt gtc cga act acg ctt gta    1548
Ala Ile Val Gly Asn Ser Ala Gly Asp Leu Val Arg Thr Thr Leu Val
                480                 485                 490 gca gta ttg atg cta gca aac ctg cgg act cac cta gtt tcg gac cat    1596
Ala Val Leu Met Leu Ala Asn Leu Arg Thr His Leu Val Ser Asp His
            495                 500                 505 ttt ccg gta aat ttt aga aaa ttt gga gat aac ta atg aaa gct tta     1643
Phe Pro Val Asn Phe Arg Lys Phe Gly Asp Asn     Met Lys Ala Leu
        510                 515                     520 gca ata ata ttt tta ttt gta agc ata agt ttt gca aac gaa aac ata    1691
Ala Ile Ile Phe Leu Phe Val Ser Ile Ser Phe Ala Asn Glu Asn Ile
    525                 530                 535 acc gac gct ttt caa ata cgc aat gca aac acc gga att cct ata aat    1739
Thr Asp Ala Phe Gln Ile Arg Asn Ala Asn Thr Gly Ile Pro Ile Asn
540                 545                 550 ata aag cga ttt tca ggg cag ttt aat tac caa aac tgg ttt tta aat    1787
Ile Lys Arg Phe Ser Gly Gln Phe Asn Tyr Gln Asn Trp Phe Leu Asn
555                 560                 565                 570 gat tta gga gta gat cct aag ata aaa aaa gta gat aaa ttt tca aat    1835
Asp Leu Gly Val Asp Pro Lys Ile Lys Lys Val Asp Lys Phe Ser Asn
                575                 580                 585 tct ttt cct ttt gga tac gtg caa ttt caa gta gca gcc gac gta aaa    1883
Ser Phe Pro Phe Gly Tyr Val Gln Phe Gln Val Ala Ala Asp Val Lys
            590                 595                 600 atg tgc ctt cag atc gct cct agc gga ttt tta gca cta aaa aac tgc    1931
Met Cys Leu Gln Ile Ala Pro Ser Gly Phe Leu Ala Leu Lys Asn Cys
        605                 610                 615 aag caa gac tac gat agc gga gag ttt gag act att ttt cag atc atc    1979
Lys Gln Asp Tyr Asp Ser Gly Glu Phe Glu Thr Ile Phe Gln Ile Ile
    620                 625                 630 cct aca agt agt gga gct atg cag cta cga tca cta gtt cta aaa aca    2027
Pro Thr Ser Ser Gly Ala Met Gln Leu Arg Ser Leu Val Leu Lys Thr
635                 640                 645                 650 aac gag tgc tta gga aca ttt gaa aat cca aac gtg ccg atc gaa gat    2075
Asn Glu Cys Leu Gly Thr Phe Glu Asn Pro Asn Val Pro Ile Glu Asp
                655                 660                 665 aga gta gga cta gta cgc tgc gtt tta gaa ttt ttt gtc gac ata gag    2123
Arg Val Gly Leu Val Arg Cys Val Leu Glu Phe Phe Val Asp Ile Glu
            670                 675                 680 cct aaa caa ctt ttt gta ttt tca ccg ccg ctt agt gaa gct aag gta    2171
Pro Lys Gln Leu Phe Val Phe Ser Pro Pro Leu Ser Glu Ala Lys Val
        685                 690                 695 att aga taa                                                        2180
Ile Arg
```

700

<210> SEQ ID NO 52
<211> LENGTH: 234
<212> TYPE: PRT
<213> ORGANISM: Campylobacter fetus

<400> SEQUENCE: 52

Met Thr Lys Ile Ile Phe Lys His Ile Lys Asn Ser Leu Ile Leu Leu
1               5                   10                  15

Phe Cys Ile Ala Leu Phe Ser Ala Cys Ser Ser Lys Thr Thr Asn Val
            20                  25                  30

Ser Thr Gln Lys Ile Asn Pro Leu Gly Ser Ile Phe Gly Lys Thr Asp
        35                  40                  45

Asp Pro Asp Pro Leu Asn Leu Gly Asp Phe Pro Thr Leu Leu Thr Ser
    50                  55                  60

Asn Phe Thr Asn Pro Met Pro Thr Arg Thr Pro Ser Pro Leu Lys Lys
65                  70                  75                  80

Val Asp Leu Pro Val Met Asn Ser Leu Thr His Gly Pro Met Phe Ser
                85                  90                  95

Ser Ala Phe Ser Lys Pro Asp Leu Asn Phe Lys Gln Pro Thr Ile Ser
            100                 105                 110

Leu Gln Gly Ile Pro Pro Asp Leu Phe Asp Arg Thr Ser Asp Phe Met
        115                 120                 125

Val Ile Met Gly Ala Asn Gly Val Val Ile Thr Ile Trp Tyr Thr Ser
    130                 135                 140

Pro Gly Asn Trp Leu Trp Gly Tyr Ser Leu Tyr Glu Ser Gly Asn Leu
145                 150                 155                 160

Gly Gly Tyr Arg Val Trp Arg Leu Ile Leu Leu Pro Asn Asn Glu Val
                165                 170                 175

Met Ile Val Asn Phe Asn Thr Arg Thr Thr Cys Ile Asn Thr Tyr Lys
            180                 185                 190

Asn Gly Val Ile His Ser Pro Cys Asn Lys Asp Asn Pro Phe Gln Lys
        195                 200                 205

Phe Thr Phe Arg Pro Met Thr Asn Gly Ala Val Gln Ile Tyr Asn Lys
    210                 215                 220

Ala Thr Asn Cys Val Leu Ala Asn Ala Cys
225                 230

<210> SEQ ID NO 53
<211> LENGTH: 284
<212> TYPE: PRT
<213> ORGANISM: Campylobacter fetus

<400> SEQUENCE: 53

Met Val Phe Ala Pro Ala Ala Ser Trp Lys Thr Ile Leu Leu Gly
1               5                   10                  15

Val Lys Met Arg Asn Val Ile Met Ile Ile Phe Ile Ala Thr Leu Gly
            20                  25                  30

Phe Ala Lys Pro Glu Asp Tyr Lys Ile Ala Thr Trp Asn Leu Gln Gly
        35                  40                  45

Ser Ser Ala Ile Thr Glu Ser Lys Trp Asn Ile Ser Val Arg Gln Ile
    50                  55                  60

Ile Ser Gly Glu Asn Pro Ala Asp Ile Leu Ala Val Gln Glu Ala Gly
65                  70                  75                  80

Asn Leu Pro Gln Thr Ala Leu Pro Thr Gly Arg Ser Ile Asn Gln Gly

-continued

```
                    85                  90                  95
Gly Thr Ile Val Thr Glu His Leu Trp Gln Leu Gly Ser Ile Ser Arg
            100                 105                 110

Pro Phe Gln Val Tyr Ile Tyr Ala Gln Ile Asp Thr Gly Ala Asn
        115                 120                 125

Arg Val Asn Leu Ala Ile Val Ser Arg Ile Lys Ala Asp Glu Ile Ile
        130                 135                 140

Ile Leu Pro Pro Pro Thr Val Ala Ser Arg Pro Leu Ile Gly Ile Arg
145                 150                 155                 160

Ile Gly Asn Asp Val Phe Phe Asn Ile His Ala Leu Ala Asn Gly Gly
                165                 170                 175

Val Asp Ala Pro Ala Ile Ile Asn Ser Ile Phe Asp Arg Phe Arg Asn
            180                 185                 190

Met Pro Asn Ile Thr Trp Met Ile Leu Gly Asp Phe Asn Arg Ser Pro
        195                 200                 205

Glu Ser Leu Arg Gly Thr Leu Gly Leu Glu Thr Arg Val Arg Val Thr
    210                 215                 220

Phe Leu Thr Pro Pro Ala Pro Thr Gln Arg Ser Gly Gly Thr Leu Asp
225                 230                 235                 240

Trp Ala Ile Val Gly Asn Ser Ala Gly Asp Leu Val Arg Thr Thr Leu
                245                 250                 255

Val Ala Val Leu Met Leu Ala Asn Leu Arg Thr His Leu Val Ser Asp
            260                 265                 270

His Phe Pro Val Asn Phe Arg Lys Phe Gly Asp Asn
        275                 280

<210> SEQ ID NO 54
<211> LENGTH: 182
<212> TYPE: PRT
<213> ORGANISM: Campylobacter fetus

<400> SEQUENCE: 54

Met Lys Ala Leu Ala Ile Ile Phe Leu Phe Val Ser Ile Ser Phe Ala
1               5                   10                  15

Asn Glu Asn Ile Thr Asp Ala Phe Gln Ile Arg Asn Ala Asn Thr Gly
            20                  25                  30

Ile Pro Ile Asn Ile Lys Arg Phe Ser Gly Gln Phe Asn Tyr Gln Asn
        35                  40                  45

Trp Phe Leu Asn Asp Leu Gly Val Asp Pro Lys Ile Lys Lys Val Asp
    50                  55                  60

Lys Phe Ser Asn Ser Phe Pro Phe Gly Tyr Val Gln Phe Gln Val Ala
65                  70                  75                  80

Ala Asp Val Lys Met Cys Leu Gln Ile Ala Pro Ser Gly Phe Leu Ala
                85                  90                  95

Leu Lys Asn Cys Lys Gln Asp Tyr Asp Ser Gly Glu Phe Glu Thr Ile
            100                 105                 110

Phe Gln Ile Ile Pro Thr Ser Ser Gly Ala Met Gln Leu Arg Ser Leu
        115                 120                 125

Val Leu Lys Thr Asn Glu Cys Leu Gly Thr Phe Glu Asn Pro Asn Val
    130                 135                 140

Pro Ile Glu Asp Arg Val Gly Leu Val Arg Cys Val Leu Glu Phe Phe
145                 150                 155                 160

Val Asp Ile Glu Pro Lys Gln Leu Phe Val Phe Ser Pro Pro Leu Ser
                165                 170                 175
```

Glu Ala Lys Val Ile Arg
            180

<210> SEQ ID NO 55
<211> LENGTH: 29
<212> TYPE: DNA
<213> ORGANISM: Artificial
<220> FEATURE:
<223> OTHER INFORMATION: an artificially synthesized primer sequence
<220> FEATURE:
<221> NAME/KEY: misc_feature
<222> LOCATION: (21)..(29)
<223> OTHER INFORMATION: "n" indicates a, t, g, or ,c

<400> SEQUENCE: 55
gcttgtagca gtattgatgc nnnnnnnnn                                  29

<210> SEQ ID NO 56
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 56
gcttgtagca gtattgatgc                                            20

<210> SEQ ID NO 57
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 57
ctagtttcgg accatttttcc                                           20

<210> SEQ ID NO 58
<211> LENGTH: 29
<212> TYPE: DNA
<213> ORGANISM: Artificial
<220> FEATURE:
<223> OTHER INFORMATION: an artificially synthesized primer sequence
<220> FEATURE:
<221> NAME/KEY: misc_feature
<222> LOCATION: (21)..(29)
<223> OTHER INFORMATION: "n" indicates a, t, g, or ,c

<400> SEQUENCE: 58
atacgcaatg caaacaccgg nnnnnnnnn                                  29

<210> SEQ ID NO 59
<211> LENGTH: 19
<212> TYPE: DNA
<213> ORGANISM: Artificial
<220> FEATURE:
<223> OTHER INFORMATION: an artificially synthesized primer sequence

<400> SEQUENCE: 59
atacgcaatg aaacaccgg                                             19

<210> SEQ ID NO 60
<211> LENGTH: 21
<212> TYPE: DNA
<213> ORGANISM: Artificial
<220> FEATURE:
<223> OTHER INFORMATION: an artificially synthesized primer sequence

```
<400> SEQUENCE: 60
taaaagcgat tttcagggca g                                        21

<210> SEQ ID NO 61
<211> LENGTH: 29
<212> TYPE: DNA
<213> ORGANISM: Artificial
<220> FEATURE:
<223> OTHER INFORMATION: an artificially synthesized primer sequence
<220> FEATURE:
<221> NAME/KEY: misc_feature
<222> LOCATION: (21)..(29)
<223> OTHER INFORMATION: "n" indicates a, t, g, or ,c

<400> SEQUENCE: 61
tgtcgacata gagcctaaac nnnnnnnnn                                29

<210> SEQ ID NO 62
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 62
tgtcgacata gagcctaaac                                          20

<210> SEQ ID NO 63
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 63
attttcaccg ccgcttagtg                                          20

<210> SEQ ID NO 64
<211> LENGTH: 34
<212> TYPE: DNA
<213> ORGANISM: Artificial
<220> FEATURE:
<223> OTHER INFORMATION: an artificially synthesized primer sequence

<400> SEQUENCE: 64
gaaactgata cactaggata cgatccattc caaa                          34

<210> SEQ ID NO 65
<211> LENGTH: 28
<212> TYPE: DNA
<213> ORGANISM: Artificial
<220> FEATURE:
<223> OTHER INFORMATION: an artificially synthesized primer sequence

<400> SEQUENCE: 65
gaataatcag gtcgctttgc taatgaca                                 28

<210> SEQ ID NO 66
<211> LENGTH: 33
<212> TYPE: DNA
<213> ORGANISM: Artificial
<220> FEATURE:
<223> OTHER INFORMATION: an artificially synthesized primer sequence

<400> SEQUENCE: 66
agcatgtctc atagatatgt actcaaaact tgg                           33
```

-continued

<210> SEQ ID NO 67
<211> LENGTH: 32
<212> TYPE: DNA
<213> ORGANISM: Artificial
<220> FEATURE:
<223> OTHER INFORMATION: an artificially synthesized primer sequence

<400> SEQUENCE: 67
agcctaagta tccataacgt cgtattcttt gc                                     32

<210> SEQ ID NO 68
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 68
aggacttgaa cctactttc                                                    20

<210> SEQ ID NO 69
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 69
aggtggagta gttaaaaacc                                                   20

<210> SEQ ID NO 70
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 70
attgccaagg ctaaaatctc                                                   20

<210> SEQ ID NO 71
<211> LENGTH: 18
<212> TYPE: DNA
<213> ORGANISM: Artificial
<220> FEATURE:
<223> OTHER INFORMATION: an artificially synthesized primer sequence

<400> SEQUENCE: 71
gataaagtct aaaactgc                                                     18

<210> SEQ ID NO 72
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 72
aacgacaaat gtaagcactc                                                   20

<210> SEQ ID NO 73
<211> LENGTH: 20
<212> TYPE: DNA
<213> ORGANISM: Artificial
<220> FEATURE:

```
<223> OTHER INFORMATION: an artificially synthesized primer sequence

<400> SEQUENCE: 73
tatttatgca agtcgtgcga                                                20

<210> SEQ ID NO 74
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 74
tttagccttt gcaactccta                                                20

<210> SEQ ID NO 75
<211> LENGTH: 19
<212> TYPE: DNA
<213> ORGANISM: Artificial
<220> FEATURE:
<223> OTHER INFORMATION: an artificially synthesized primer sequence

<400> SEQUENCE: 75
aaggggtagc agctgttaa                                                 19

<210> SEQ ID NO 76
<211> LENGTH: 21
<212> TYPE: DNA
<213> ORGANISM: Artificial
<220> FEATURE:
<223> OTHER INFORMATION: an artificially synthesized primer sequence

<400> SEQUENCE: 76 tagggatat gcacgcaaaa g                                               21

<210> SEQ ID NO 77
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 77
gcttaataca gttacgatag                                                20

<210> SEQ ID NO 78
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 78
aagcataagt tttgcaaacg                                                20

<210> SEQ ID NO 79
<211> LENGTH: 21
<212> TYPE: DNA
<213> ORGANISM: Artificial
<220> FEATURE:
<223> OTHER INFORMATION: an artificially synthesized primer sequence

<400> SEQUENCE: 79
gtttggattt tcaaatgttc c                                              21
```

The invention claimed is:

1. An isolated polynucleotide encoding a cytolethal distending toxin, which is any one of:
   (a) a polynucleotide encoding a polypeptide comprising the amino acid sequence of SEQ ID NO: 2;
   (b) a polynucleotide comprising the nucleotide sequence of position 1 to 777 in the nucleotide sequence of SEQ ID NO: 1;
   (c) a polynucleotide encoding a polypeptide comprising an amino acid sequence with a substitution, deletion, addition, and/or insertion of one to 30 amino acids in the amino acid sequence of SEQ ID NO:2;
   (d) a polynucleotide that hybridizes under a stringent condition of 1×SSC, 0.1% SDS, and 37° C. to DNA comprising the nucleotide sequence of position 1 to 777 in the nucleotide sequence of SEQ ID NO: 1.

2. A vector comprising the polynucleotide of claim 1.

3. A host cell containing the polynucleotide of claim 1 or the vector of claim 2.

4. A method for producing a cytolethal distending toxin, which comprises the step of culturing the host cell of claim 3 and collecting the produced polypeptide from the host cell or the culture supernatant.

* * * * *